(12) United States Patent
Uchida et al.

(10) Patent No.: US 9,248,164 B2
(45) Date of Patent: Feb. 2, 2016

(54) GROWTH FACTOR ANCHORING TYPE BONE GRAFT MATERIAL, METHOD FOR PRODUCING GROWTH FACTOR ANCHORING TYPE BONE GRAFT MATERIAL, KIT FOR PRODUCING GROWTH FACTOR ANCHORING TYPE BONE GRAFT MATERIAL, AND METHOD FOR FORMING BONE

(75) Inventors: Kentaro Uchida, Sagamihara (JP); Koji Naruse, Sagamihara (JP); Masashi Takaso, Sagamihara (JP); Takehiko Mima, Sagamihara (JP); Osamu Matsushita, Sagamihara (JP); Takashi Haraguchi, Sagamihara (JP); Nozomu Nishi, Kagawa (JP)

(73) Assignees: SCHOOL JURIDICAL PERSON KITASATO INSTITUTE, Tokyo (JP); NATIONAL UNIVERSITY CORPORATION KAGAWA UNIVERSITY, Takamatsu-Shi, Kagawa (JP)

( * ) Notice: Subject to any disclaimer, the term of this patent is extended or adjusted under 35 U.S.C. 154(b) by 29 days.

(21) Appl. No.: 14/117,599

(22) PCT Filed: Mar. 26, 2012

(86) PCT No.: PCT/JP2012/057829
§ 371 (c)(1),
(2), (4) Date: Jan. 6, 2014

(87) PCT Pub. No.: WO2012/157339
PCT Pub. Date: Nov. 22, 2012

(65) Prior Publication Data
US 2014/0335146 A1 Nov. 13, 2014

(30) Foreign Application Priority Data
May 13, 2011 (JP) ................................. 2011-108650

(51) Int. Cl.
| A61K 38/18 | (2006.01) |
| A61K 9/70 | (2006.01) |
| A61K 47/42 | (2006.01) |
| A61L 27/54 | (2006.01) |
| A61K 38/48 | (2006.01) |
| A61L 27/36 | (2006.01) |
| C07K 14/33 | (2006.01) |
| C07K 14/485 | (2006.01) |
| C12N 9/52 | (2006.01) |

(52) U.S. Cl.
CPC ......... *A61K 38/1825* (2013.01); *A61K 38/1808* (2013.01); *A61K 38/4886* (2013.01); *A61L 27/3608* (2013.01); *A61L 27/54* (2013.01); *C07K 14/33* (2013.01); *C07K 14/485* (2013.01); *C12N 9/52* (2013.01); *A61L 2300/252* (2013.01); *A61L 2300/414* (2013.01); *A61L 2430/02* (2013.01); *C07K 2319/00* (2013.01); *C07K 2319/003* (2013.01); *C07K 2319/70* (2013.01)

(58) Field of Classification Search
None
See application file for complete search history.

(56) References Cited

U.S. PATENT DOCUMENTS

| 4,950,483 | A | 8/1990 | Ksander et al. | |
| 6,146,420 | A * | 11/2000 | McKay | 623/17.16 |
| 2007/0128245 | A1 | 6/2007 | Rosenberg et al. | |
| 2007/0160681 | A1 | 7/2007 | Park et al. | |
| 2007/0248575 | A1 | 10/2007 | Connor et al. | |
| 2009/0036893 | A1 * | 2/2009 | Kartalian et al. | 606/60 |
| 2010/0129341 | A1 | 5/2010 | Sakon et al. | |
| 2010/0196489 | A1 | 8/2010 | Thorne | |
| 2011/0281351 | A1 | 11/2011 | Adachi et al. | |
| 2012/0130435 | A1 | 5/2012 | Hart et al. | |

FOREIGN PATENT DOCUMENTS

| JP | 4-500954 | | 2/1992 |
| JP | 2002-58485 | A | 2/2002 |
| JP | 2003-525696 | A | 9/2003 |
| JP | 2007/530099 | A | 11/2007 |
| JP | 2009-519052 | A | 5/2009 |
| JP | 2009-534125 | A | 9/2009 |
| JP | 2010-508912 | A | 3/2010 |
| JP | 2010-512967 | A | 4/2010 |
| JP | 2010-523671 | A | 7/2010 |
| WO | WO 01/66044 | A2 | 9/2001 |
| WO | WO 2005/089826 | A1 | 9/2005 |
| WO | WO 2008/124166 | A2 * | 10/2008 |
| WO | WO 2010/087397 | A1 | 8/2010 |
| WO | WO 2011/142425 | A1 | 11/2011 |

OTHER PUBLICATIONS

Chen et al., 2007, Biomaterials 28:1027-1035.*
Chen et al , "Homogeneous osteogenesis and bone regeneration by demineralized bone matrix loading with collagen-targeting bone morphogenetic protein-2", ScienceDirect, Biomaterials, vol. 28 (2007) pp. 1027-1035.
Japanese Office Action issued in Japanese Application No. 2013-515034 on Dec. 17, 2013, with English translation.
Extended European Search Report for European Application No. 12785014.7, dated Oct. 20, 2014.
Wang et al., "Basic Fibroblast Growth Factor Enhances Bone-Graft Incorporation: Dose and Time Dependence in Rats," Journal of Orthopaedic Research, vol. 14, No. 2, Mar. 1996, pp. 316-323, XP000922662.

(Continued)

*Primary Examiner* — Elizabeth C Kemmerer
(74) *Attorney, Agent, or Firm* — Birch, Stewart, Kolasch & Birch, LLP

(57) ABSTRACT

Provided is a growth factor anchoring type bone graft material, wherein a bone graft substrate exposing at least a collagen fiber is bound to a collagen-binding-site-containing growth factor which contains a growth factor receptor agonist peptide and a collagen-binding peptide. The same can be produced by mixing a bone graft substrate and a collagen-binding-site-containing growth factor which contains a growth factor receptor agonist peptide and a collagen-binding peptide, and is also superior in osteogenic ability.

2 Claims, 6 Drawing Sheets

(56) References Cited

OTHER PUBLICATIONS

Imen et al., "Construction of multifunctional proteins for tissue engineering: Epidermal growth factor with collagen binding and cell adhesive activities," Journal of Biotechnology, 2009, vol. 139, pp. 19-25.

International Search Report Issued in PCT/JP2012/057829, mailed on May 1, 2012.

Nishi et al., "Collagen-binding growth factors: Production and characterization of functional fusion proteins having a collagen-binding domain," Proc. Natl. Acad. Sci. USA, Medical Sciences, Jun. 1998, vol. 95, pp. 7018-7023.

Shi et al., "Regeneration of full-thickness abdominal wall defects in rats using collagen scaffolds loaded with collagen-binding basic fibroblast growth factor," Biomaterials, Jan. 2011, vol. 32, pp. 753-759.

Visser et al., "The effect of an rhBMP-2 abosrbable collagen sponge-targeted system on bone formation in vivo," Biomaterials, 2009, vol. 30, pp. 2032-2037.

* cited by examiner

GROWTH FACTOR ANCHORING TYPE BONE GRAFT MATERIAL, METHOD FOR PRODUCING GROWTH FACTOR ANCHORING TYPE BONE GRAFT MATERIAL, KIT FOR PRODUCING GROWTH FACTOR ANCHORING TYPE BONE GRAFT MATERIAL, AND METHOD FOR FORMING BONE

TECHNICAL FIELD

The present invention relates to a bone graft material bound a bone graft substrate exposing at least a collagen fiber to a growth factor, more particularly, relates to a growth factor anchoring type bone graft material wherein a bone graft substrate is bound to a collagen-binding-site-containing growth factor which comprises a growth factor receptor agonist peptide and a collagen-binding peptide, a method for producing the growth factor anchoring type bone graft material, a kit for production of a growth factor anchoring type bone graft material, and a method for forming a bone.

BACKGROUND ART

When an artificial joint has been implanted for treating articular rheumatism or arthrosis deformans and caused loosening between the artificial joint and bone tissues after long period service, it should be replaced by a new one through artificial joint revision surgery. On an artificial joint revision surgery, bone grafting with an autologous bone derived from the patient, or the like, is carried out in order to supplement a part of lost bone. Bone grafting has a feature that a bone protein contained in grafted bone promotes resorption of the grafted bone and conversion to an autologous tissue, therefore it has an advantage that reconstruction of a joint function becomes possible even though reconstruction with a prosthesis is impossible. Further, bone is a tissue superior in regenerative capacity, it may be regenerated into a nearly original form by proper reintegration and fixation in case of a fracture.

However, autologous bone grafting is a method which own bone is cut out from a certain part of a patient as a block, the obtained bone is transplanted to deficient part as a block, or after crushing to a granular or powder form. The method is an advantage of high safety because own bone is utilized although, pains are severe at the bone collecting part in the case of a large bone defect region, the recovery period after the bone grafting surgery becomes longer, and sometimes it is very difficult to find a donor supplying a bone for bone grafting. To avoid such drawbacks, allogeneic bone grafting using a donor-derived bone instead of an autologous bone is conducted, and further, various bone graft materials have been also developed.

For example, there is a composition used for promoting bone formation in arthrodesis which includes a platelet-derived growth factor solution, a biocompatible matrix containing polysaccharides, and a scaffold material such as calcium phosphate (Patent Literature 1). In the example thereof, 1.0 mg/mL of platelet-derived growth factor is dropped to calcium phosphate in the average diameter of 1000 to 2000 µm for preparing a composition, and the composition is coated on a bone to be fused in a joint. As the result, the composition exhibits bone bridging and joint adhesion equivalent to autologous bone grafting.

Further, there is a bone graft material on which surface a cell adhesion inducing peptide having an RGD amino acid sequence, or a tissue growth factor-derived peptide is fixed (Patent Literature 2). The bone graft material adhering on the surface a tissue growth factor capable of obtaining a tissue regeneration effect and a peptide having active site of an extracellular matrix protein exhibits allegedly a stable and sustainable pharmacological effect, even though the concentration of the peptides is low. In the example thereof surfaces of a bovine bone-derived bone mineral particle are treated with 3-aminopropyltriethoxysilane to form an amine residue, the particles are bound with a crosslinking agent of 1,4-bis-maleimidebutane added thereto, then reacted with a cell adhesion inducing peptide to fix the peptide, and prepare a bone graft material. The material exhibits allegedly superior regenerative power compared to a bone graft material without the fixed peptide.

There is also a bone graft fragment composition prepared by drying a fragment of a cell-free tissue substrate together with a fragment of a demineralize bone material (Patent Literature 3). A cell-free tissue substrate such as collagen obtained from an epithelial cell has capability for supporting cell recognition and cell association, as well as cell spreading, cell proliferation, and cell differentiation, a demineralize bone material has physiological characteristics of natural bone important for a success of bone grafting. When the obtained bone graft fragment composition is coated on a transplantation or implantation part after hydration, new bone formation can be allegedly induced in or on a surface of an osseous tissue, or in or on a surface of a non-osseous tissue of a recipient by stimulating a bone formation stem cell.

Meanwhile, there is also a composition containing a fusion protein fused a PTH/PTHrP receptor agonist with a collagen-binding polypeptide fragment drived from a collagenase (Patent Literature 4). A parathyroid hormone (PTH) is used for an anabolic therapy of osteoporosis, an administration once a day is required. The composition can form a stable bind with collagen through a collagen-binding polypeptide fragment, and stay at an administration site for a long time period resisting body fluid circulation to enjoy longer half-life than PTH. Then, it can exert allegedly the same or higher effectiveness compared to PTH administration. In the example, it is administered intraperitoneally and increase of the bone density is observed.

Further, a fusion protein which a basic fibroblast growth factor (bFGF) instead of a PTH/PTHrP receptor agonist is bound to a collagen-binding polypeptide fragment, has been also known (Non Patent Literature 1).

Further, based on knowledge that it is useful to use a bone promoting factor in a treatment of a fracture, there is a bone formation promoting fusion protein prepared by binding a polypeptide having a collagen-binding domain derived from fibronectin with a bone formation promoting protein (Patent Literature 5). As examples of the bone formation promoting protein are named a growth factor belonging to a BMP (Bone Morphogenetic Proteins) subfamily, bFGF, and a thyroid hormone. In the example the polypeptide is prepared by using mRNA extracted from human kidney cells as a template thereof, bound with BMP2 or BMP7 as the bone formation promoting protein to prepare the bone formation promoting fusion protein. When the fusion protein was suspended with an osteoblast to be a mouse calvarium-derived established cell, administration of the bone formation promoting fusion protein caused allegedly concentration-dependent enhancement of alkali phosphatase activity on an osteoblast compared to administration of the above polypeptide.

Further, there is a composition for a treatment of a bone defect composed of a forming particle having at least 4 curved projections composed of calcium sulfate or the like and a material for a suspension (Patent Literature 6). A plurality of the projection of the forming particle can interlock each other to stabilize filling into a defect site, a binder capable of forming a gel of a collagen derivative or the like, or a bone morphogenic protein (BMP) can use as the suspension.

Further, there is a self-curing porous calcium phosphate composition which contains calcium phosphate, a blowing agent, and a biocompatible flocculant, and is mixed with a physiologically acceptable liquid, can releases a gas component by hydration of the blowing agent in the composition, gives at least 5% of porosity to the composition, and after curing the calcium phosphate composition exhibits a compressive strength of 1 MPa or more (Patent Literature 7). As the biocompatible flocculant collagen is disclosed and it is described that the composition may contain further a collagen exposure-treated substrate. The invention has a feature that a porous calcium phosphate composition is formed by a blowing agent, and in the example thereof a collagen exposure-treated substrate, sodium hydrogen carbonate and calcium phosphate as a blowing agent, and carboxymethyl cellulose as a flocculant were mixed to prepare a self-curing paste. By filling the self-curing paste in a defect formed at a rabbit distal femoral condyle, nearly complete healing was allegedly observed.

Additionally, there is a bone growth composition containing a particulate fibrous collagen component, and a calcium phosphate component, as well as a substance selected from the group consisting of a purified bone growth factor, a recombinant bone growth factor, a bone-marrow component, and demineralized bone and autologous bone (Patent Literature 8). The collagen component is cross-linked collagen or porous granular or other insoluble collagen. In the example, a calcium phosphate gel dispersion is kneaded with complex collagen, and after a cross-linking step by freeze-drying and thermal dewatering shaped into the particulate, pasted by adding blood, then transplanted to scattered bone. A defect site could be allegedly fixed firmly with the paste.

CITED LITERATURE

Patent Literatures

Patent Literature 1: Japanese National Publication of International Patent Application No. 2010-508912.
Patent Literature 2: Japanese National Publication of International Patent Application No. 2007-530099.
Patent Literature 3: Japanese National Publication of International Patent Application No. 2009-534125.
Patent Literature 4: Japanese National Publication of International Patent Application No. 2010-523671.
Patent Literature 5: Unexamined Japanese Patent Application Kokai Publication No. 2002-58485.
Patent Literature 6: Japanese National Publication of International Patent Application No. 2003-525696.
Patent Literature 7: Japanese National Publication of International Patent Application No. 2009-519052.
Patent Literature 8: Japanese National Publication of International Patent Application No. 2010-512967.

Non Patent Literature

Non Patent Literature 1: "Collagen-binding growth factors: Production and characterization of functional fusion proteins having a collagen-binding domain", Nozomu Nishi, et al., Proc. Natl. Acad. Sci., USA, Vol. 95, pp 7018-7023, June 1998, Medical Sciences.

SUMMARY OF INVENTION

Technical Problem

Bone grafting is exercised on an artificial joint revision surgery, a treatment of fracture, and a bone defect due to malignant osteosarcoma, but in some cases, even though graft bone originated from autologous bone or allogeneic bone is used, a graft bone applied to a bone occurs faulty union or delayed union to the site of application to the bone reportedly. Such faulty union or delayed union means prolongation of a treatment period and becomes an economical, physical, and mental burden on the patient. In view of the situation that fractures occur frequently among aged persons in the recent aging society, soonest bone union is desired in order to initiate rehabilitation as soon as possible.

However, the bone graft material of Patent Literature 1, although calcium phosphate or the like used as a scaffold material is advantageous in terms of easy availability, bone growth or early union surpassing autologous bone is difficult. In the case of the bone graft material of Patent Literature 2, a cell adhesion inducing peptide or a tissue growth factor-derived peptide is fixed on a bone surface, the same can remain at an administration part at a high retention rate, and exhibit superior bone regenerative power. It, however, requires a cross-linking treatment for fixing the peptide on the bone surface, which makes the production difficult. Meanwhile, Patent Literature 3 requires use of a demineralized bone material, and for demineralization extraction with 0.6 N hydrochloric acid for 3 to 24 hours is necessary, namely the treatment time becomes longer. Further, although it is advantageous that the bone graft material of Patent Literature 3 or Patent Literature 4 uses an active ingredient relevant to bone growth, such a component is easy to leave from the administrated part due to body fluid circulation, and a high retention rate may not be maintained at the administrated part.

Further, by the method according to Patent Literature 5, a collagen-binding domain is limited to what derived from fibronectin. Although bFGF is disclosed as a bone formation promoting protein, its actual effect is unexplained. Patent Literature 6 is characterized by using a forming particle having a predetermined shape, and despite a description that BMP may be added, an actual evaluation has not been conducted. Even if the component is added, it is presumed that the component will easily leave from the administrated part due to body fluid circulation and is not able to establish a high retention rate. Further, in the case of Patent Literature 7, there is a description that collagen may be mixed as a biocompatible flocculant to formed porous calcium phosphate, however an actual evaluation has not been conducted. Further, since the porous calcium phosphate and the collagen are not fixed together by a covalent bond, the same will easily leave an administrated part due to body fluid circulation, and a sustainable effect is presumed to be hardly attainable. Further, in the case of Patent Literature 8, cross-linked collagen shaped a particulate form is used, however preparation is not easy, and despite a disclosure that a bone growth factor can be added, an actual evaluation has not been conducted. Further, even if a bone growth factor is mixed with the cross-linked collagen, the bone growth factor easily leaves an administration part due to body fluid circulation, and presumably an effect is hardly attainable for a long period.

Regarding artificial joint revision surgery, there are many cases e.g. replacement of a half of femur which can be hardly reconstructed with autologous bone or artificial bone not having an anatomical shape. In such a case there is no other method than transplant of an allogeneic bone maintaining an anatomical shape and having mechanical strengths. Similarly, for a treatment of an intractable fracture, a plate of cortical bone having mechanical strengths is utilized. If a huge allogeneic bone with an anatomical shape is transplanted, it may cause more easily a faulty union or a delayed union at administrated part, compared to a collagen-exposing bone material or crushed bone not having mechanical strengths or an anatomical shape.

In view of the above situation, an object of the present invention is to provide a bone graft material that can maintain the retention rate of a bone growth factor at an administration part, while securing an anatomical shape and mechanical strengths of a bone, and expectedly attain early bone union.

Another object of the present invention is to provide a bone graft material having mechanical strengths and being superior in osteogenic ability, a method for producing a bone graft material, a kit for producing a bone graft material, and a method for forming a bone using the bone graft material.

Solution to Problem

The present inventors have found that a superior osteogenic ability can be expected by binding a fusion protein which a growth factor is bound to a collagen-binding peptide to a bone, that the fusion protein can easily bind to the bone graft substrate exposing at least a collagen fiber by mixing it with the bone graft substrate without a cross-linking reaction or the like, and further that the obtained growth factor anchoring type bone graft material can exert the osteogenic ability at an administratied part for a long time period and consequently early bone union can be expected, thereby established the present invention.

Namely, the present invention provides a growth factor anchoring type bone graft material, wherein a bone graft substrate exposing at least a collagen fiber is bound to a collagen-binding-site-containing growth factor which comprises a growth factor receptor agonist peptide and a collagen-binding peptide (hereinafter also referred to as "CB-GF").

Further, the present invention provides the growth factor anchoring type bone graft material, wherein the collagen-binding-site-containing growth factor comprises the growth factor receptor agonist peptide, the collagen-binding peptide, and a linker.

Further, the present invention provides the growth factor anchoring type bone graft material, wherein the bone graft substrate is a collagen-exposing bone material or a high-density collagen material.

Further, it provides the growth factor anchoring type bone graft material, wherein the growth factor receptor agonist peptide is a basic fibroblast growth factor.

Further, the present invention provides a method for producing a growth factor anchoring type bone graft material, wherein the bone graft substrate and the CB-GF are mixed.

Further, it provides the method for producing a growth factor anchoring type bone graft material, wherein the bone graft substrate is a collagen-exposing bone material prepared by treating a bone with an acid and removing an inorganic mineral component dissolved by the acid.

Further, the present invention provides a kit for production of a growth factor anchoring type bone graft material, comprising a solution comprising the CB-GF and a bone graft substrate.

Further, the present invention provides a kit for production of a growth factor anchoring type bone graft material, comprising a solution comprising the CB-GF and a collagen-exposing bone material preparation solution.

Further, it provides a method for forming a bone, wherein the growth factor anchoring type bone graft material is transplanted to a bone defect region and/or a non-union region.

Further, the present invention provides the method for forming a bone, wherein the growth factor anchoring type bone graft material is prepared by preparing a collagen-exposing bone material by crushing a bone and treating the same with an acid for 1 to 60 min, and binding the CB-GF to the collagen-exposing bone material.

Advantageous Effects of Invention

A growth factor anchoring type bone graft material of the present invention which a growth factor receptor agonist peptide is bound to a bone graft substrate exposing at least collagen fiber through a collagen-binding peptide of the bone graft substrate, is entirely derived from biogenic substances, and has excellent affinity for an organism and safety.

The growth factor anchoring type bone graft material of to the present invention can be produced easily by simply mixing a bone graft substrate exposing at least a collagen fiber with a CB-GF prepared in advance to be bound together.

Since the growth factor anchoring type bone graft material of the present invention can utilize the bone forming activities of both the bone graft substrate exposing at least a collagen fiber and a growth factor, a good union effect can be exerted even for a case in which union is difficult at the application site of the bone.

Since the kit for production of a growth factor anchoring type bone graft material of the present invention can prepare a collagen-exposing bone material in a short time, it can be used easily at the time of autologous bone grafting.

BRIEF DESCRIPTION OF DRAWINGS

FIG. 1A shows the evaluation results concerning the binding capability between a bone material derived from an epiphysis as a source material prior to a collagen-exposing treatment, and the EGF-PKD-CBD fusion protein; FIG. 1B is a diagram showing the results concerning the binding capability between the bone material after a collagen-exposing treatment and the EGF-PKD-CBD fusion protein;

FIG. 2A shows the evaluation results concerning the binding capability between a bone material derived from a diaphysis prior to a collagen-exposing treatment, and an EGF-PKD-CBD fusion protein; FIG. 2B is a diagram showing the results concerning the binding capability between the bone material from a diaphysis after a collagen-exposing treatment and the EGF-PKD-CBD fusion protein;

FIG. 3A shows the evaluation results concerning the binding capability between a bone material derived from an epiphysis as a source material prior to a collagen-exposing treatment, and a bFGF-PKD-CBD fusion protein; FIG. 3B is a diagram showing the results concerning the binding capability between the bone material after a collagen-exposing treatment and the bFGF-PKD-CBD fusion protein;

FIG. 4A shows the evaluation results concerning the binding capability between a bone material derived from a diaphysis prior to a collagen-exposing treatment, and a bFGF-PKD-CBD fusion protein; FIG. 4B is a diagram showing the results concerning the binding capability between the bone material from a diaphysis after a collagen-exposing treatment and the bFGF-PKD-CBD fusion protein;

FIG. 5A shows the results of a group of bone graft substrates binding a bFGF-PKD-CBD fusion protein; FIG. 5B shows the results of a group of a crushed bone derived from an epiphysis;

DESCRIPTION OF EMBODIMENTS

Figure 1:
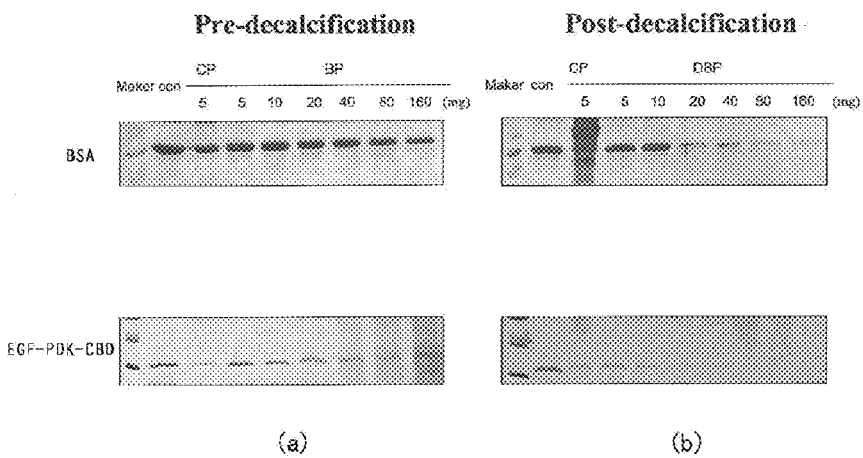
FIG. 1 is a diagram showing the results concerning binding capability between a bone graft substrate and an EGF-PKD-CBD fusion protein which is a CB-GF having an EGF as a growth factor receptor agonist peptide.
Figure 2:
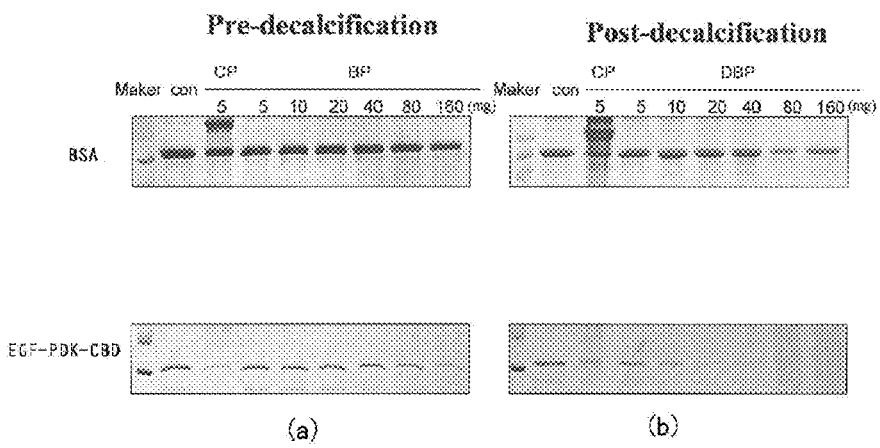
FIG. 2 is a diagram showing the results concerning binding capability between a bone material using a diaphysis instead of an epiphysis in FIG. 1 and an EGF-PKD-CBD fusion protein.

The first aspect of the present invention is a growth factor anchoring type bone graft material characterized in that a bone graft substrate exposing at least a collagen fiber is bound to a CB-GF.

(1) Growth Factor Anchoring Type Bone Graft Material

A bone is constituted with network-formed collagen fibers and hydroxyapatite deposited thereon, and most part of organic substances of a bone is collagen. In a collagen molecule 3 polypeptide chains are bound in a helical fashion, and a large number of the molecules associate in vivo to form insoluble fibers. A collagen exposure-treated matrix (demineralized bone matrix=DBM) prepared by treating a bone with an acidic solution or a chelating reagent to remove nearly completely inorganic substances contains active substances. The substances differentiate undifferentiated mesenchymal cells existing in subcutaneous tissues and muscles to osteoblasts to promote bone formation. The DBM is used as a bone graft material, natural mechanical strengths of a bone, however, have been lost because the same has been demineralized nearly completely. A "growth factor anchoring bone graft material" of the present invention is to use a bone graft substrate exposing at least a collagen fiber. For example, a bone graft substrate which at least a part of inorganic substances is removed from a bone to expose collagen fibers on the bone surface can be used. Such a bone graft substrate to which a CB-GF is bound retains highly its anatomical shape and excels in dynamically, because a large amount of mineral remains in the substrate. In such a bone graft substrate, collagen fibers exist therein without degradation, and the CB-GF can be bound thereto simply by mixing with the bone graft substrate, and therefore production is easy.

The growth factor anchoring type bone graft material of the present invention can be expected synergistic bone forming activity by a growth factor, in addition to the osteogenic ability owned inherently by the bone graft substrate exposing at least a collagen fiber. Furthermore, since the growth factor is bound to the bone graft substrate, it can stay long at a grafted site and promote sustained bone formation. Additionally an autologous bone is used as a source material of the bone graft substrate, it is advantageous in that an immunological rejection reaction can be avoided.

Although there is no particular restriction on the amount of the CB-GF to be bound to the bone graft substrate for the growth factor anchoring bone graft material of the present invention, with respect to 1 mg (dry weight) of a bone graft substrate a CB-GF is bound preferably in an amount of 0.01 to 1 nmol, preferably 0.1 to 1 nmol, and more preferably 0.5 to 1 nmol. Even if the CB-GF is bound beyond 1 nmol, the increasing rate of bone formation is not improved any more; and if it is below 0.01 nmol, the effect of the bound CB-GF may occasionally not be attainable sufficiently.

With respect to a growth factor anchoring bone graft material of the present invention, it is possible that a bone is subjected to a collagen-exposing treatment to prepared the bone graft substrate at the time to use, binding thereto a CB-GF, thereafter it is used as a bone graft material; or alternatively a growth factor anchoring bone graft material prepared in advance by binding a CB-GF to a bone graft substrate and dried for preservation can be used by suspending it in a buffer solution when needed. When a collagen-binding peptide included in the growth factor anchoring bone graft material binds to a collagen fiber by means of its stereostructure, it is preferable to suspend it in a buffer solution that can secure the stereostructure. Examples of such a buffer solution include a phosphate buffer solution of pH 7.4 and a Tris buffer solution.

The growth factor anchoring bone graft material of the present invention can be administered locally for the purpose of increasing bone density, increasing bone mineral density, or increasing new bone similarly to a conventional bone graft material such as an autologous bone graft material. For example, by an administration through a transplant or the like to a bone defect region or a non-union region suffered after tumor curettage or artificial joint revision surgery, bone formation can be promoted. It can be used favorably especially for cases requiring a bone graft material maintaining an anatomical shape and mechanical strengths, such as artificial joint revision surgery, and intractable fracture treatment.

(2) CB-GF

With respect to a CB-GF to be used in the present invention, there is no particular restriction on its structure or production method, insofar as it includes a growth factor receptor agonist peptide (hereinafter also referred to as "GF site") and a collagen-binding peptide (hereinafter also referred to as "CB site"), and both of the peptides may be bound chemically, or it may be a fusion protein including a GF site and a CB site. In this case, the CB site may be binding directly or through a linker composed of a polypeptide fragment with the GF site. Additionaly, 2 polypeptides of the GF site and the CB site may be cross-linked by a reagent including disuccinimidyl glutarate or glutaraldehyde through an amino group. Further, a polypeptide is derivatized by succinimidyl-4-hydrazinonicotinate acetone hydrazone, and the other polypeptide is derivatized by succinimidyl-4-formyl benzoate, and then two derivatized polypeptides may be mixed for cross-linking through an amino group. According to the present invention, the two may be linked by a crosslinking agent other than polypeptides or other compounds to bind the GF site and the CB site.

(i) Collagen-binding peptide

A "collagen-binding peptide" constituting the CB-GF to be used in the present invention is a functional site to bind a growth factor receptor agonist peptide to the bone graft substrate. Although a growth factor exerts bone forming activity as described above, it cannot be expected sustained bone forming activity because a low local residual ratio by systemic administration such as an intravenous injection. In the present invention, a bone graft substrate exposing at least a collagen fiber is used as a bone graft material, the CB-GF including a GF site and a CB site prepared in advance is mixed with the bone graft substrate to bind a growth factor receptor agonist to the bone graft substrate.

As a method for binding a GF site to a bone graft substrate, a method for binding a bone graft substrate such as a collagen-exposing bone material to a specific component by a chemical cross-linking reaction has been known, for example, as shown in Patent Literature 2. However, by the method, an operation of the reaction is troublesome, and a crosslinking agent may occasionally remain in the collagen-exposing bone material. On the other hand, by the present invention using the CB-GF, the GF site can be bound to the collagen-exposing bone material through a CB site in the CB-GF, without using a crosslinking agent or other chemical components. The growth factor anchoring type bone graft material of the present invention can be prepared easily, and is superior in safety since a crosslinking agent is not used. Further, it is superior in retention of the mechanical strengths and the anatomical shape of the collagen-exposing bone material.

Figure 12:
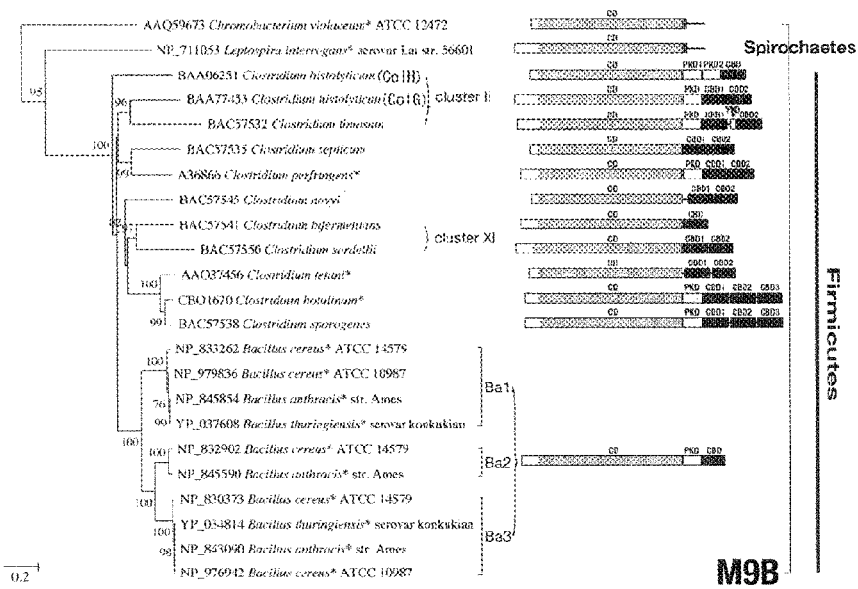
FIG. 12 is a figure illustrating types of bacterial collagenases having a collagen-binding peptide (CBD) and the CBDs.

In the present invention, a "CB site" may include widely what can bind at least a part of collagen fibers. Examples of a polypeptide bindable to a collagen fiber include a collagenase-derived collagen binding site. Examples of a structural gene for the collagenase-derived collagen binding site include a DNA fragment including a base sequence of base Nos. 3001 to 3366 of a gene (GenBank Accession Number D29981) of *Clostridium histolyticum* collagenase (hereinafter occasionally referred to as "ColH") as set forth in SEQ ID NO: 1. The DNA fragment codes for an amino acid sequence specified by GenBank Accession Number BAA06251. Referring to FIG. 12, a catalytic site represented by CD and a collagen binding site represented by CBD are included and the base sequence of base Nos. 3001 to 3366 corresponds to a CBD. Similarly, *Clostridium histolyticum* collagenase (hereinafter occasionally referred to as "ColG") specified by GenBank Accession Number BAA77453, *Clostridium limosum* collagenase specified by ditto BAC57532, *Clostridium septicum* collagenase specified by ditto BAC57535, *Clostridium perfringens* collagenase specified by ditto A36866, *Clostridium novyi* collagenase specified by ditto BAC57545, *Clostridium bifermentans* collagenase specified by ditto BAC57541, *Clostridium sordellii* collagenase specified by ditto BAC57550, *Clostridium tetani* collagenase specified by ditto AAO37456, *Clostridium botulinum* collagenase specified by ditto CBO1620, *Clostridium sporogenes* collagenase specified by ditto BAC57538, *Bacillus cereus* collagenase specified by ditto NP_833262, *Bacillus cereus* collagenase specified by ditto NP_979836, *Bacillus cereus* collagenase specified by ditto NP_833262, *Bacillus cereus* collagenase specified by ditto NP_979836, *Bacillus anthracis* collagenase specified by ditto NP_845854, *Bacillus thuringiensis* collagenase specified by ditto YP_037608, *Bacillus cereus* collagenase specified by ditto NP_832902, *Bacillus anthracis* collagenase specified by ditto NP_845590, *Bacillus cereus* collagenase specified by ditto NP_830373, *Bacillus thuringiensis* collagenase specified by ditto YP_034814, *Bacillus anthracis* collagenase specified by ditto NP_843090, *Bacillus cereus* collagenase specified by ditto NP_976942, and other collagen-binding peptides derived from a bacterial collagenase may be used similarly.

Meanwhile, a "CB site" to be used in the present invention is required to bind to a collagen fiber of the bone graft substrate exposing at least a collagen fiber to the extent that the growth factor can be retained there, and therefore it is not necessary to contain the entire amino acid sequence of a collagenase-derived collagen binding site. For example, the collagen-binding peptide having 90% homology with the base sequence constituting a CBD in the amino acid sequence may be favorably used. There is no particular restriction on a binding method, and, for example, it may be bound with an affinity for a part of collagen fibers exposing out of a surface of the collagen-exposing bone material.

(ii) Growth factor receptor agonist peptide

A GF site constituting a CB-GF to be used in the present invention is a site for exerting a function of a growth factor or the like by binding to a bone graft substrate. Examples of a growth factor include an epithelial growth factor (EGF), a fibroblast growth factor (FGF), and a platelet-derived growth factor (PDGF), and a growth factor receptor agonists exerting such actions widely may be used. Further growth factors such as TGF-β, IGF-1, and BMP do not exert a heterotopic bone inducing activity but exert a bone forming activity, they can promote healing of fracture when applied to a fractured part.

As a structural gene for such a growth factor receptor agonist, especially use of a basic fibroblast growth factor is preferable. Examples of such a basic fibroblast growth factor include a DNA fragment composed of a base sequence of base Nos. 468 to 932 of the *Homo sapiens* fibroblast growth factor 2 (basic) gene (NCBI Reference Sequence Accession Number NM_002006.4) as set forth in SEQ ID NO: 2. As a structural gene for an epithelial growth factor, there is also cDNA (SEQ ID NO: 3) of preproEGF (GenBank Accession Number U04842) of *Rattus norvegicus*. The amino acid sequence of preproEGF encoded by the DNA is set forth in SEQ ID NO: 4.

As a GF site a basic fibroblast growth factor (bFGF) may be used favorably in the present invention. Since a basic fibroblast growth factor is superior in osteogenic ability, if the CB-GF bound to a basic fibroblast growth factor as a constituent growth factor (hereinafter referred to as "CB-bFGF") is bound to the bone graft substrate the uniting ability between a recipient bed bone and a grafted bone is superior. A CB-GF bound to an epithelial growth factor (EGF) in place of a basic fibroblast growth factor is referred to as CB-EGF.

(iii) Linker

A CB-GF may be used what is bound to the CB site and the GF site through a linker. By insertion of a linker the CB site and the GF site can be isolated by a predetermined gap width, thus each site can independently fully exert each function. As the result, by insertion of the linker the CB-GF can be bound stronger to collagen fibers than the CB-GF without the linker.

Examples of such a linker include a peptide fragment which does not have a specific three-dimensional structure and is composed of amino acids, such as serine, threonine, proline, asparaginic acid, glutamic acid, and lysine. Further, as such a linker an amino acid sequence derived from the ColH may be used favorably. More specifically, a polycystic kidney disease I domain (hereinafter referred to as "PKD") of the ColH may be used favorably. Additionally, a PKD derived from another bacterial collagenase may be also used favorably as the linker. This is because the collagen binding ability of the CBD is reinforced by coexistence of the PKD. Such a linker derived a bacterial collagenase is depicted in FIG. 12 as PKD. Incidentally, such a linker should preferably be resistant to a peptide hydrolase or the like contained in a human circulatory liquid, the local residual performance of the GF site is enhanced and bone formation can be persistently promoted.

(3) Bone Graft Substrate

A "bone graft substrate" to be used in the present invention is the bone graft substrate exposing at least a collagen fiber. Examples of the bone graft substrate include a collagen-exposing bone material and a high-density collagen material.

(i) Collagen-exposing bone material

As the collagen-exposing bone material, for example, the collagen-exposing bone material such as crushed bone which is removed at least a part of an inorganic mineral component from the bone may be used favorably. It is not limited to a so-called complete decalcified bone, namely a bone from which all the contained inorganic mineral component is removed. Thereby mechanical strengths of a bone can be secured and the anatomical shape of the same can be retained. By removing a part of the inorganic mineral component, collagen fibers contained in a bone are exposed to a bone surface, and the CB-GF can be bound through the collagen-binding peptide.

A "bone" to be used of the present invention may be any of autologous bone, allogeneic bone, and heterologous bone. Heterologous bone other than human may be from any of primates, such as monkey, baboon, and chimpanzee, swine, cattle, horse, goat, sheep, dog, cat, rabbit, guinea pig, mongolian gerbil, hamster, rat, and mouse. A "collagen-exposing bone material" contains in addition to collagen richly a growth factor, and various peptides and small proteins, maintaining the osteogenic ability. In the present invention, by using a collagen-exposing bone material a growth factor contained in the bone material can be efficiently bound, and the anatomical shape, the mechanical strengths, and the bone inducing potency of a bone can be utilized effectively.

The collagen-exposing bone material to be used in the present invention can be prepared by immersing a bone in an acid solution to expose collagen fibers. Prior to the acid treatment a treatment for removing soft tissues, or a treatment with an organic solvent such as alcohol for removing bone marrow, blood, and lipid, may be conducted.

A bone collected in a block form may be used after shaping into a form corresponding to a bone defect region, or crushing also. When a bone is crushed, the shape may be irregular, and the size may be not uniform. A treatment step for crushing a bone substrate to an appropriate particle size is not limited to before the collagen-exposing treatment, and it may be conducted simultaneously with the collagen-exposing treatment, or conducted after the collagen-exposing treatment. The crushing treatment can be carried out usually with a commonly used a crusher or a mixer, and in either of a wet state and a dry state of a bone substrate. As for the particle size, for example, the largest diameter may be in a range of 50 to 5000 μm, preferably 50 to 1000 μm, and more preferably 50 to 2000 μm.

As for the collagen-exposing bone material to be used in the present invention, a bone which is removed at least a part of an inorganic mineral component so as to expose collagen fibers out of a bone surface may be favorably used. Collagen fibers are required to be exposed from bone tissues to the extent that a CB-GF can bind thereto. A content of calcium can be used as an indicator for removal of an inorganic mineral component. The relative calcium content compared to the value before a collagen-exposing treatment should be reduced up to 95 to 10%, preferably 95 to 40%, more preferably 95 to 60%, and especially preferably 95 to 80%. By mixing a CB-GF thereafter, it can be bound to the collagen-exposing bone material. Conventionally, as a bone graft substrate a complete decalcified bone which a calcium component has been removed to the extent possible is used in general. In the present invention an inorganic mineral component is, however, required to be removed only in the above range, the collagen-exposing treatment time can be shortened.

Such a collagen-exposing treatment on a bone can be performed by dissolving an inorganic mineral component with hydrochloric acid, acetic acid, nitric acid, sulfuric acid, formic acid, or the like. The concentration or treatment conditions may be appropriately selected according to an acid used. For example, in the case 0.6 N hydrochloric acid is used, the temperature is from 0 to 10° C., and the time is from 30 sec to 18 hours, preferably from 60 sec to 6 hours, more preferably from 60 sec to 1 hour, and especially preferably from 60 sec to 2 min. Conventionally, a collagen-exposing treatment was performed by extraction with 0.6 N hydrochloric acid for 3 to 24 hours, the target of the acid extraction was to reduce the calcium content below 5%, as described in Patent Literature 3. However, by the growth factor anchoring type bone graft material of the present invention, it is enough to bind the CB-GF to collagen fibers contained in crushed bone, and further to be killed viable cells to the extent that the antigenecity is removed. By a review of collagen-exposing treatment, it is found that, when a bone is crushed in the largest diameter of 50 to 5000 μm, then treated with 0.6 N hydrochloric acid within the above range, the CB-GF is efficiently bound, the mechanical strengths are kept, and viable cells are killed to reduce antigenicity even if an allogeneic bone is used. The collagen-exposing bone material to be used in the present invention can be used by removing an inorganic mineral component contained in the acid solution after the acid treatment. As a method for removing the inorganic mineral component, the supernatant is removed and washed with water or a phosphate buffer solution, or it may be washed with a chelating reagent.

The collagen-exposing bone material to be used in the present invention may be prepared by using an autologous bone. When allogeneic bone grafting is carried out, the collagen-exposing bone material may be prepared by using a donor bone, according to the above, and preserved in a buffer solution or preserved dry.

(ii) High density collagen material

In the present invention a high-density collagen material may be used as the bone graft substrate. Since a collagen-exposing treatment with an acid for producing a collagen-exposing bone material is not required, the growth factor anchoring type bone graft material can be prepared in a short time.

The density of collagen fibers in the high-density collagen material is from 100 to 800 mg/cm$^3$, preferably from and 300 to 800 mg/cm$^3$, more preferably from 400 to 800 mg/cm$^3$. The mechanical strengths can be superior in the range. The high-density collagen material may be in a sheet form, a columnar form, a spherical form, a polyhedral form, or in another irregular form. Among them the high-density collagen material in a sheet form can be used favorably for e.g. coating a bone surface. There is no particular restriction on a collagen fiber composing the high-density collagen material, and it may be any of collagen types I to XI. Preferably, it is type I. The high-density collagen material is preferably constituted with atelocollagen which a part or all of a telopeptide is removed from a collagen. The high-density collagen material can be prepared by freeze-drying or otherwise drying a solution containing collagen fibers, being pressurizing to the above density and into a sheet form. A commercial product may be also used.

(4) Method for Producing Growth Factor Anchoring Type Bone Graft Material

Since both of the GF site and the CB site constituting the CB-GF to be used in the present invention are peptides, they can be prepared as a fusion protein. When the CB-GF includes a basic fibroblast growth factor (bFGF) as a growth factor receptor agonist, and PKD-CBD derived from ColH as a linker and a CB site, the CB-GF is herein referred to as "bFGF-PKD-CBD". A method for producing a bFGF-PKD-CBD is disclosed in Non Patent Literature 1, the bFGF-PKD-CBD can be produced by the method. By using a basic fibroblast growth factor (bFGF) as a GF site, and a CBD derived from ColG as a CB site, a bFGF-CBD can be also produced by fusing the two. By using a gene sequence for an epithelial cell growth factor (EGF) instead of a gene sequence for a bFGF, a CB-EGF can be produced similarly as above. Further by using a gene sequence coding for another growth factor receptor agonist, a CB-GF which the growth factor receptor agonist binds to the CB can be produced. As described above, the CB site and the GF site may be cross-linked by a crosslinking agent.

In the present invention the growth factor anchoring type bone graft material maybe produced by mixing the EGF-PKD-CBD, or other CB-GF with the above bone graft substrate. Generally, by adding predetermined amounts of the bone graft substrate and the CB-GF into a phosphate buffer solution, stirring the mixture for 60 sec to 60 min, preferably 5 to 30 min, and more preferably 15 to 30 min at a temperature of 0 to 10° C., or leaving it standing, the CB-GF can be bound to the bone graft substrate.

The growth factor anchoring type bone graft material of the present invention can be easily prepared and used provided that the bone graft substrate is prepared at a conventional autologous bone grafting, then the CB-GF prepared in advance is added immediately the substrate to prepare the growth factor anchoring type bone graft material. In the case of allogeneic bone grafting, the bone graft substrate which is prepared by the above method in advance or preserved in a buffer solution may be used. Furthermore a growth factor anchoring type bone graft material which is prepared by immersing a dried bone graft substrate in a buffer solution and adding the CB-GF thereto may be used as a grafting bone material.

(5) Kit for Production of a Growth Factor Anchoring Type Bone Graft Material As a kit for production of a growth factor anchoring type bone graft material of the present invention, there are a kit (I) composed of a CB-GF solution and the bone graft substrate, and a kit (II) composed of a CB-GF solution and a collagen-exposing bone material preparation solution.

(i) Kit (I)

A kit (I) is composed of a CB-GF solution and the bone graft substrate. Examples of a bone graft substrate include a donor bone which is removed at least a part of an inorganic mineral component to expose collagen fibers and then preserved in a buffer solution, the same preserved in a dry state, and the high-density collagen material.

The CB-GF solution in the kit (I) is a solution dissolving the CB-GF in a buffer solution in a range of 0.5 to 2.0 mg/mL. Examples of a buffer solution include a phosphate buffer solution of pH 7.0 to 8.0, Tris buffer solution, and a physiological saline solution. Since the bone graft substrate is included in the kit, the growth factor anchoring type bone graft material can be easily prepared by adding the CB-GF solution to the bone graft substrate before transplanting.

(ii) Kit (II)

A kit (II) is composed of a collagen-exposing bone material preparation solution in place of a bone graft substrate, and a CB-GF solution. For example, at an autologous bone grafting, the collagen-exposing bone material can be easily prepared by immersing an autologous bone in the collagen-exposing bone material preparation solution followed by washing. By adding the CB-GF solution to the obtained collagen-exposing bone material followed by mixing, the growth factor anchoring type bone graft material can be prepared. An acid solution such as 0.6 N hydrochloric acid solution, and acetic acid, as well as an acid solution to which a chelating reagent is added, may be used as a collagen-exposing bone material preparation solution. A kit (II) may be used favorably for conducting an autologous bone grafting.

(6) Method for Forming Bone

The growth factor anchoring type bone graft material of the present invention is a bone graft material which the CB-GF including the GF site such as FGF, TGF-$\beta$, IGF-1, and PDGF, and the CB site is bound to the bone graft substrate. The osteogenic ability based on the bone graft substrate and the osteogenic effect based on the growth factor can be expected. For a treatment of a bone defect region suffered after tumor curettage or artificial joint revision surgery or a treatment of a non-union (pseudoarthrosis), crushed autologous bone as a graft bone or crushed allogeneic bone as a graft bone has been heretofore used. By using the growth factor anchoring type bone graft material instead of a conventional graft bone, a growth factor can stay for a long period at the grafted site and promote bone formation persistently, thereby forming a bone earlier than in the past.

Specifically, by transplanting the growth factor anchoring type bone graft material to a bone defect region or a non-union region suffered after tumor curettage or artificial joint revision surgery, bone formation can be promoted.

For example, at the time of an autologous bone grafting operation, a graft bone is obtained, crushed in the range of the largest diameter 50 to 5000 µm, and stirred in 0.6 N hydrochloric acid for 1 min to perform a collagen-exposing treatment. Then the obtained collagen-exposing bone material is washed with water, rinsed with a phosphate buffer solution (pH 7.0 to 8.0), added the CB-GF thereto and mixed for approx. 1 to 30 min, thereby preparing a growth factor anchoring type autologous bone graft material. By grafting the same to a bone defect region or a non-union region suffered after tumor curettage or artificial joint revision surgery, an autologous bone grafting can be carried out. Contrary to a conventional autologous bone, the growth factor anchoring type bone graft material of the present invention includes the CB-GF. Therefore excellent bone formation based on the CB-GF can be expected. On an occasion of a fracture or the like early ambulation owing to premature fusion at an affected part becomes possible, so that rehabilitation can be started early. In the case of an allogeneic bone grafting, it is possible to prepare a growth factor anchoring type allogeneic bone graft material before the surgery. Therefore, an allogeneic bone grafting can be carried out effectively within a short operation time and with minimal invasion.

A collagen-exposing bone material preparation solution in the kit (II) can be used for the preparation of the collagen-exposing bone material, and a CB-GF solution in the kit (II) may be used as the CB-GF.

EXAMPLES

Next, the present invention will be specifically described below referring to Examples, provided that the present invention be not restricted in any way by the Examples.

Production Example 1

Production of EGF-PKD-CBD Fusion Protein (1) A region of base Nos. 3001 to 3366 in DNA (SEQ ID NO: 1) of ColH is a gene fragment coding for a collagen binding domain (CBD). A region of base Nos. 2719 to 3000 in the DNA (SEQ ID NO: 1) is a gene fragment coding for a PKD domain (PKD) of a bacterial collagenase, and can be used for a linker. Therefore, a region of base Nos. 2719 to 3391 in the DNA (SEQ ID NO: 1) including the sites was cut off and inserted it into a SmaI site in a pGEX-4T-2 plasmid in the usual manner.

(2) A DNA (SEQ ID NO: 5) consisting of a base sequence of base Nos. 3308 to 3448 in cDNA SEQ ID NO: 3 of pre-proEGF of *Rattus norvegicus* (GenBank Accession Number U04842) was amplified by a PCR method so as to have a BamHI site at the 5'end and one nucleotide (G residue) for alignment of a reading frame of a fusion protein and an EcoRI site at the 3'end. The fragment was inserted into the BamHI-EcoRI site of the expression vector according to the item (1) by an usual manner. The obtained expression plasmid possesses a reading frame (SEQ ID NO: 7) coding for a GST-EGF-PKD-CBD fusion protein (SEQ ID NO: 6).

(3) The obtained expression plasmid (2) above was introduced in *Escherichia coli* (BL21 Codon Plus RIL) by an electroporation method.

The *Escherichia coli* was precultured overnight in 50 mL of a 2×YT-G culture medium containing 50 µg/mL of ampicillin and 30 µg/mL of chloramphenicol. To 500 mL of the culture medium 10 mL of the obtained precultured liquid was added and shake-cultured at 37° C. until the turbidity (O. D. 600) of the bacterial suspension became approx. 0.7. To the obtained bacterial suspension, 5 mL of a 0.1 M-aqueous solution of isopropyl-β-D-thiogalactopyranoside (IPTG) was added, and cultured at 37° C. for 2 hours. Then, 5 mL of phenylmethylsulfonyl fluoride (PMSF) solution containing 0.1 M isopropanol was added, and the culture solution was centrifuged at 6,000×g, and 4° C. for 10 min to collect a transformant. Bacterial cells were suspended in 7.5 mL of a phosphate buffered physiological saline solution (PBS) containing 1 mM PMSF, and the cells were destructed by a French press. A 20%-Triton X-100 solution equivalent to 1/19 volume of the suspension was added and stirred at 4° C. for 30 min. The lysate was centrifuged at 15,000×g, and 4° C. for 30 min to obtain a supernatant, and the resulting supernatant was then centrifuged again under the same condition. The supernatant was defined as a cleared lysate solution. To glutathione-sepharose beads (2 mL), the cleared lysate solution was added and stirred at 4° C. for 1 hour to bind a GST-EGF-PKD-CBD fusion protein to the beads. After washing the beads with 12 mL of PBS five times, the beads were suspended in a small amount of PBS and loaded onto a column. The fusion protein was eluted with 50 mM Tris-HCl (pH 8.0) and 10 mM glutathione solution. Five units of thrombin per mg of the fusion protein were added and the mixture was subjected to a reaction at 25° C. for 10 hours to cleave a GST tag. After that, dialysis against 300 mL of PBS at 4° C. for 12 hours was repeated four times. The dialyzed cleavage product was added to a column filled with fresh glutathione-sepharose beads (2 mL) washed with PBS and directly eluted. As a result, the GST tag was removed and EGF-PKD-CBD fusion protein (SEQ ID NO: 6; 225 to 491) without the GST tag was obtained.

Production Example 2

Production of bFGF-PKD-CBD Fusion Protein

Firstly, a DNA fragment (PKD-CBD gene) including a base sequence of base Nos. 2719 to 3391 of the ColH gene set forth in SEQ ID NO: 1 was inserted in an SmaI site of a pGEX-4T-2 plasmid (by GE Healthcare, Japan) in the usual manner. Meanwhile, a DNA fragment (bFGF gene) consisting of a base sequence of base Nos. 468 to 932 in the *Homo sapiens* fibroblast growth factor 2 (basic) gene (NCBI Reference Sequence Accession Number NM_002006.4) set forth in SEQ ID NO: 2 was amplified by a PCR method so as to have a BamHI site at the 5'end and one nucleotide (G residue) and an EcoRI site at the 3'end. The amplified DNA fragment (bFGF gene) was inserted into the BamHI-EcoRI site plasmid inserted the DNA fragment (PKD-CBD gene) in the usual manner, thereby preparing an expression plasmid. The obtained expression plasmid possesses a reading frame (SEQ ID NO: 9) coding GST-bFGF-PKD-CBD fusion protein (SEQ ID NO: 8). The amino acid sequence of the bFGF-PKD-CBD fusion protein is set forth in SEQ ID NO: 10, and the base sequence coding for the bFGF-PKD-CBD fusion protein is set forth in SEQ ID NO: 11. In the amino acid sequence according to SEQ ID NO: 10, the N-terminal 2 amino acid residues Gly-Ser are a part of a recognition site of a GST tag cleavage enzyme (thrombin protease). The expression plasmid was introduced in *Escherichia coli* (BL21 Codon Plus RIL, by Stratagene) by an electroporation method to produce a transformant.

The transformant was precultured overnight in 50 mL of a 2×YT-G culture medium containing 50 µg/mL of ampicillin and 30 µg/mL of chloramphenicol. Ten mL of the obtained preculture solution was added to 500 mL of the culture medium and was shake-cultured at 37° C. until the turbidity (O. D. 600) of the bacterial suspension reached approx. 0.7. To the obtained bacterial suspension 5 mL of a 0.1 M isopropyl-β-D-thiogalactopyranoside (IPTG) aqueous solution was added and the mixture was cultured at 37° C. for 2 hours. After adding 5 mL of an isopropanol solution containing 0.1 M phenylmethylsulfonyl fluoride (PMSF), the bacterial suspension was centrifuged at 6000×g and 4° C. for 10 min to collect the transformant. The transformant was suspended in 7.5 mL of 50 mM Tris-HCl (pH 7.5), 0.5M NaCl and 1 mM PMSF, and the cells were destructed by a French press. To 19 volume of the suspension, 1 volume of a 20% Triton (registered trademark) X-100 was added and stirred at 4° C. for 30 min. The obtained bacterial suspension was centrifuged at 15,000×g and 4° C. for 30 min and the supernatant was recovered. The obtained supernatant was further centrifuged at 15,000×g and 4° C. for 30 min and the supernatant was recovered. The supernatant was defined as a clarified lysate. The clarified lysate was added to 2 mL of glutathione-sepharose beads and stirred at 4° C. for 1 hour. After washing the beads 5 times with 12 mL of 50 mM Tris-HCl (pH 7.5) and 0.5M NaCl, the beads were suspended in small amount of 50 mM Tris-HCl (pH 7.5) and 0.5M NaCl, and filled in a column. Then the GST-bFGF-PKD-CBD fusion protein was eluted therefrom with an elution liquid (50 mM Tris-HCl (pH 8.0), 0.5M NaCl and 10 mM glutathione). Thrombin in an amount of 5 units per 1 mg of the fusion protein was added and allowed to react at 25° C. for 10 hours. The obtained reaction solution was added to 1 mL of heparin-sepharose beads and stirred at 4° C. for 3 hours allowing the bFGF-PKD-CBD fusion protein to bind to the beads. After discarding the supernatant gently, the beads were washed 3 times with 12 mL of 50 mM Tris-HCl (pH 7.5) with 0.5 M NaCl. The beads were filled in a column and the protein was eluted with 10 mL of 50 mM Tris-HCl (pH 7.5) with the salt gradient of NaCl from 0.5 to 2M, to obtain the bFGF-PKD-CBD fusion protein (SEQ ID NO: 10).

Production Example 3

Production of bFGF-CBD Fusion Protein

A DNA fragment including a base sequence of base Nos. 4011 to 4358 of the ColG gene set forth in SEQ ID NO: 12 was amplified by a PCR method so as to have an SmaI site at the 5'end, and an XhoI site at the 3'end. The fragment was inserted between an SmaI site and an XhoI site of a pGEX-4T-2 plasmid in the usual manner. Meanwhile, a DNA fragment (bFGF gene) consisting of a base sequence of base Nos. 468 to 932 of the *Homo sapiens* fibroblast growth factor 2 (basic) gene (NCBI Reference Sequence Accession Number NM_002006.4) set forth in SEQ ID NO: 2 was amplified by a PCR method so as to have a BglII site at the 5'end, and a nucleotide (base G) and an EcoRI site at the 3'end. The amplified DNA fragment (bFGF gene) was inserted in the usual manner in a BamHI-EcoRI site of the plasmid into which the DNA fragment (CBD gene) was inserted to prepare an expression plasmid. The expression plasmid possesses a reading frame coding for the GST-bFGF-CBD fusion protein (SEQ ID NO: 13). The amino acid sequence of the bFGF-CBD fusion protein is an amino acid sequence corresponding to base Nos. 720 to 1503 of the base sequence set forth in SEQ ID NO: 13. In the amino acid sequence, the N-terminal 2 amino acid residues Gly-Ser are a part of a recognition site of a GST tag cleavage enzyme (thrombin protease). The expression plasmid was introduced in *Escherichia coli* (BL21 Codon Plus RIL, by Stratagene) by an electroporation method to produce a transformant.

A bFGF-CBD fusion protein was produced identically with the production example 2, except that this transformant was used.

Example 1

A femur was obtained from a 2 months old male Wistar rat and subjected to defatting freeze-drying.

The bone tissue was divided to epiphysis and diaphysis, and each of them was crushed to an average particle size of 50 to 300 μm. To 40 mg of each crushed bone 1 mL of 0.6 N hydrochloric acid was added and the mixture was stirred at a temperature of 4° C. for 18 hours. Then the mixture was washed twice with a pH 7.4-phosphate buffer solution to prepare a collagen-exposing bone material of epiphysis or diaphysis.

To the crushed bone (bone material before collagen-exposing treatment) of epiphysis 5 mg, 10 mg, 20 mg, 40 mg, 80 mg, and 160 mg, 0.2 mL each of a phosphate buffer solution and 1.16 nmol of the EGF-PKD-CBD fusion protein obtained in the production example 1 were added and mixed for 30 min. After mixing, a supernatant was collected and the amount of the fusion protein contained in the supernatant was examined by SDS-PAGE. The results are shown in FIG. 1A. In FIG. 1A are shown from left molecular weight marker (Marker), stock solution of the EGF-PKD-CBD fusion protein obtained in the production example 2 (con), collagen (CP) 5 mg, crushed bone (BP) 5 mg, crushed bone (BP) 10 mg, crushed bone (BP) 20 mg, crushed bone (BP) 40 mg, crushed bone (BP) 80 mg, and crushed bone (BP) 160 mg.

While to each of 5 mg, 10 mg, 20 mg, 40 mg, 80 mg and 160 mg (weight before collagen-exposing treatment) of the collagen-exposing bone material (DBP) from epiphysis, instead of the crushed bone of epiphysis (bone material before collagen-exposing treatment), 0.2 mL of a phosphate buffer solution and 1.16 nmol of the EGF-PKD-CBD fusion protein obtained in the production example 1 were added and mixed for 30 min. After mixing, a supernatant was collected and the amount of the fusion protein contained in the supernatant was examined by SDS-PAGE. For comparison instead of the EGF-PKD-CBD fusion protein 1.16 nmol of bovine albumin was added and the same procedures were carried out. The results are shown in FIG. 1B. In FIG. 1 to FIG. 4, groups using the crushed bone are referred to as Pre-decalcification (BP) and groups using the collagen-exposing bone material are referred to as Post-decalcification (DBP).

Further, using a crushed bone of diaphysis instead of the crushed bone of epiphysis, and using a collagen-exposing bone material of diaphysis instead of the collagen-exposing bone material of epiphysis, the same procedures were carried out, and the binding activities of the EGF-PKD-CBD fusion protein were evaluated. The results are shown in FIG. 2A and FIG. 2B respectively.

Comparing FIG. 1A and FIG. 1B, in FIG. 1A the amount of the fusion protein in the supernatant is constant irrespective of the amount of the crushed bone, in FIG. 1B the amount of the fusion protein in the supernatant is decreased in proportion to increase in the amount of the collagen-exposing bone material. Since the EGF-PKD-CBD fusion protein not bound to the collagen-exposing bone material is present in the supernatant, it is presumed that as the amount of collagen-exposing bone material was increased, more EGF-PKD-CBD fusion protein was bound to the collagen-exposing bone material. Meanwhile, in the case of epiphysis, even with respect to bovine albumin the residual amount in a supernatant is decreased depending on the amount of the collagen-exposing bone material similarly to the EGF-PKD-CBD fusion protein, to indicate that the binding capability of a protein is increased by the collagen-exposing treatment.

Further, comparing FIG. 1B and FIG. 2B with respect to the binding amount of the EGF-PKD-CBD fusion protein to the collagen-exposing bone material, the binding amounts to the collagen-exposing bone material derived from epiphysis and to the collagen-exposing bone material derived from diaphysis were nearly the same. On the other hand, as obvious from the comparison of FIG. 1B and FIG. 2B, the amount of BSA in the supernatant was larger for diaphysis. This means that the binding amount of albumin depends on a bone part. It is presumed that of the present invention, the EGF-PKD-CBD fusion protein could be anchored to a crushed bone irrespective of a used bone part.

Example 2

The same procedures were carried out as in Example 1, except that the bFGF-PKD-CBD fusion protein obtained in the production example 2 was used instead of the EGF-PKD-CBD fusion protein, and the binding activities of the bFGF-PKD-CBD fusion protein to the crushed bone and the collagen-exposing bone material derived from epiphysis, and the crushed bone and the collagen-exposing bone material derived from diaphysis respectively were examined. The results of the binding activities of the bFGF-PKD-CBD fusion protein to the crushed bone and the collagen-exposing bone material derived from epiphysis are shown in FIG. 3A and FIG. 3B, and the results of the binding activities of the bFGF-PKD-CBD fusion protein to the crushed bone and the collagen-exposing bone material derived from diaphysis are shown in FIG. 4A and FIG. 4B.

Comparing FIG. 3A and FIG. 3B, the amounts of the fusion protein in the supernatant were decreased with increase in the amount of the crushed bone and also of the collagen-exposing bone material. However, for the collagen-exposing bone material the dependence on the amount of bone was higher than for the crushed bone to indicate that the binding capacity of the bFGF-PKD-CBD fusion protein was improved by a collagen-exposing treatment.

Figure 3:
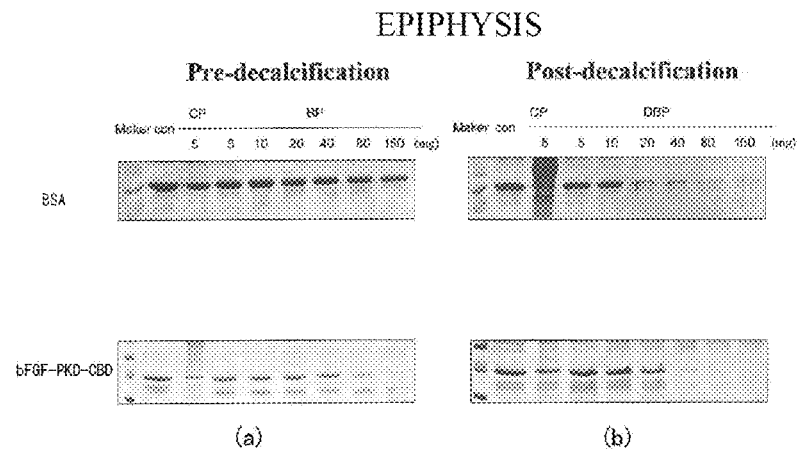
FIG. 3 is a diagram showing the results concerning binding capability between a bone graft substrate and a bFGF-PKD-CBD fusion protein which is a CB-GF having a bFGF as a growth factor receptor agonist peptide in Example 2.
Figure 4:
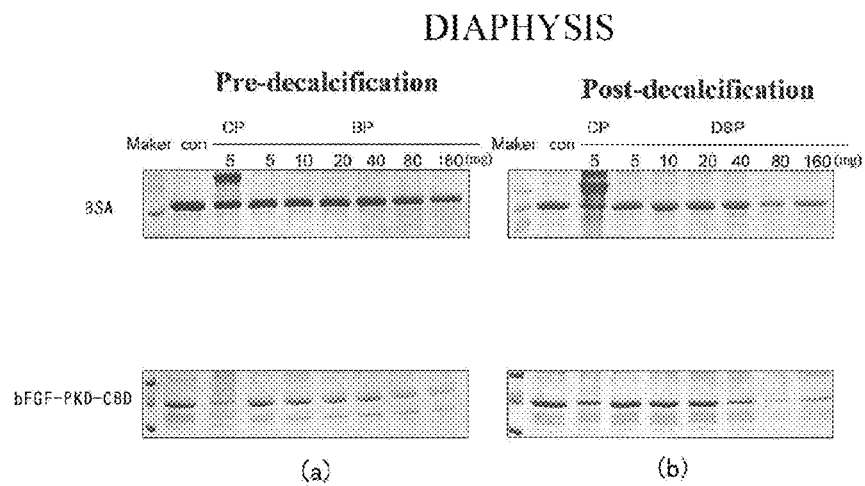
FIG. 4 is a diagram showing the results concerning binding capability between a bone graft substrate using a diaphysis instead of an epiphysis in FIG. 3 and a bFGF-PKD-CBD fusion protein.

Further, by comparing FIG. 3 and FIG. 4, with respect to the collagen-exposing bone material derived from diaphysis by addition of 80 mg, the bFGF-PKD-CBD fusion protein in the supernatant was nearly disappeared, while with respect to the collagen-exposing bone material derived from epiphysis by addition of 40 mg the same in the supernatant was nearly disappeared, to indicate that the binding capability of the bFGF-PKD-CBD fusion protein was higher for a collagen-exposing bone material derived from epiphysis than for a collagen-exposing bone material derived from diaphysis. It was also indicated that of the present invention a CB-GF can be anchored to the collagen-exposing bone material irrespective of a used bone part and a used CB-GF type.

Example 3

Six 2 months old male Wistar rats were divided to 2 groups of 3 each. Both of the groups were anesthetized with Nembutal on the anterior femoral, and a collagen-exposing bone material (growth factor anchoring type bone graft material), in which 20 mg of the bFGF-PKD-CBD fusion protein bind prepared in the production example 2 was bound to 20 mg (weight before collagen-exposing treatment) of a collagen-exposing bone material prepared identically with Example 1 was transplanted on the anterior femoral periosteum of one group, and 20 mg of a crushed bone of epiphysis prepared in Example 1 was transplanted on the anterior femoral periosteum of the other group.

Bone formation was observed with time by taking a soft X ray photograph every week. The results of the transplant of the collagen-exposing bone material with the bound bFGF-PKD-CBD fusion protein are shown in FIG. 5A, and the results of the transplant of the crushed bone of epiphysis are shown in FIG. 5B.

Figure 5:
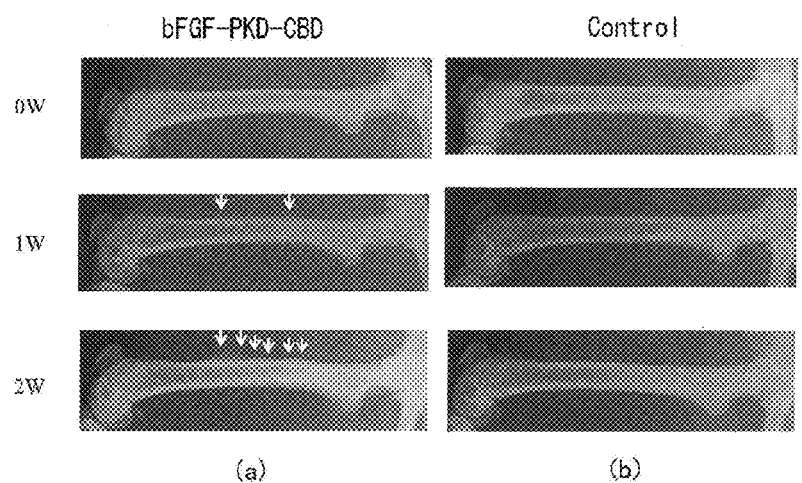
FIG. 5 is a diagram showing the results of Example 3.
Figure 6:
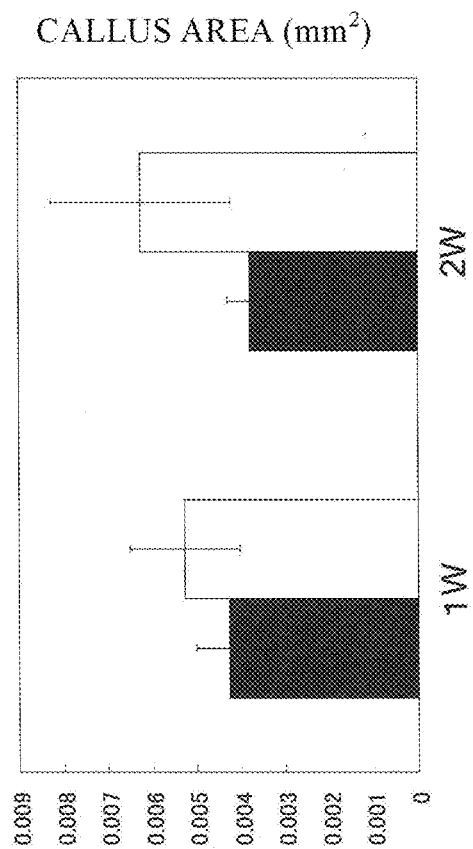
FIG. 6 is a diagram showing the area of callus in Example 3.

As shown in FIG. 5A, when a growth factor anchoring type bone graft material was transplanted on the anterior femoral periosteum, after approx. 1 week from the transplant a bone tissue was observed (arrow) in the vicinity of the growth factor anchoring type bone graft material, and after approx. 2 weeks a bone tissue with certain thickness was observed in a wider range. On the contrary, in the control group transplanted with a crushed bone, even 2 weeks after the transplant, no bone tissue could be observed in the vicinity of the crushed bone. Meanwhile, the area of a new bone tissue (callus) is shown in FIG. 6. The black bar is for the control group, and the white bar is for the group bound to the bFGF-PKD-CBD fusion protein.

It has become clear that a growth factor anchoring type bone graft material of the present invention can form a bone tissue faster than a conventional allogeneic bone grafting.

Example 4

From a 2 months old male Wistar rat a femur was obtained and subjected to defatting freeze-drying.

The diaphysis of the bone tissue was crushed to an average particle size of 50 to 300 μm. The crushed bone was divided to 3 groups of 40 mg each (weight before collagen-exposing treatment), and the group 1 was for a not collagen exposure-treated crushed bone (BP), and group 2 and group 3 were for a collagen exposure-treated crushed bone (DBP). To the collagen exposure-treated crushed bone (DBP) groups, 1 mL of 0.6 N hydrochloric acid was added and stirred at a temperature of 4° C. for 1 min or 18 hours. The mixture was then washed twice with a pH 7.4 phosphate buffer solution and used as a bone graft substrate of diaphysis.

Figure 7:
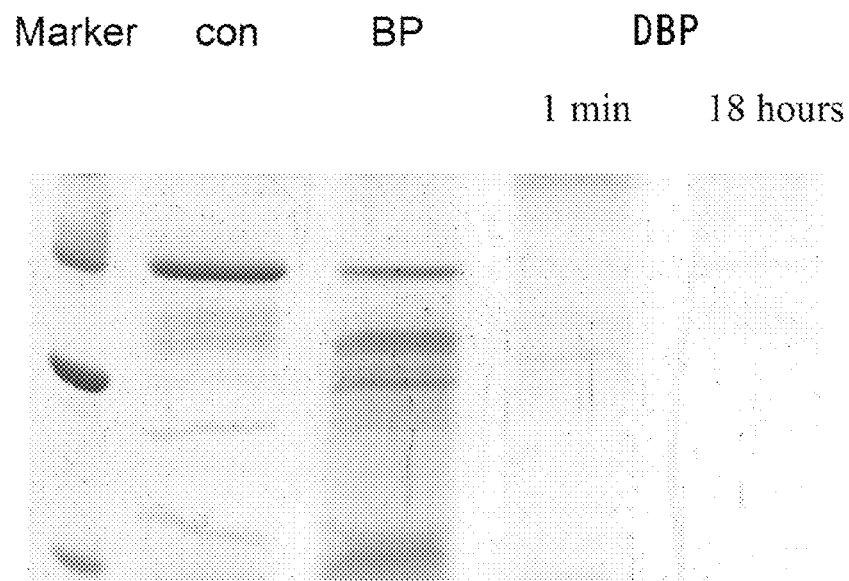
FIG. 7 is a diagram showing the results of Example 4.

Next, to each of 40 mg of the crushed bone (BP) of diaphysis, the group of the 1 min-collagen-exposing treatment, and the group of the 18 hour-collagen-exposing treatment, 0.2 mL of a phosphate buffer solution and 1.16 nmol of the bFGF-PKD-CBD fusion protein obtained in the production example 2 were added and blended for 30 min. After the blending a supernatant was collected and the amount of the fusion protein in the supernatant was examined by SDS-PAGE. The results are shown in FIG. 7. The calcium content of the group of the 1 min-collagen-exposing treatment was 90 mass-%, and the calcium content of the group of the 18 hour-collagen-exposing treatment was 10 mass-%.

In FIG. 7 are shown from left molecular weight marker (Marker), stock solution (con), crushed bone (BP), crushed bone with 1 min-collagen-exposing treatment (DBP), and crushed bonewith 18 hour-collagen-exposing treatment (DBP).

As shown in FIG. 7, for the crushed bone (BP) a fusion protein is observed in the supernatant, on the contrary for both of the crushed bonewith 1 min-collagen-exposing treatment (DBP), and crushed bonewith 18 hour-collagen-exposing treatment (DBP), no fusion protein is observed in supernatants to indicate that a CB-GF can be bound to the bone graft substrate even after a short time collagen-exposing treatment.

Example 5

Sixty four 10 weeks old male Wistar rats were divided to 4 groups of 16 each. A growth factor anchoring type bone graft material was prepared by reacting 20 mg (weight before collagen-exposing treatment) of a demineralize bone material of diaphysis prepared as in Example 1, with 1.16 nmol of a bFGF, 0.29 nmol of a bFGF-PKD-CBD fusion protein, or 1.16 nmol of a bFGF-PKD-CBD fusion protein, and transplanted on the anterior periosteum of the femoral diaphysis.

After 1 week and 2 weeks from the transplant, the femora of 8 rats of each group were obtained and the new bone volume was measured using a micro-CT. Meanwhile, a phosphate buffer solution (PBS) and the collagen-exposing bone material were reacted and transplanted as the control. The results are shown on FIG. 8.

The white bar is for the control group, the grey bar is for the 1.16 nmol bFGF group, the black bar is for the 0.29 nmol bFGF-PKD-CBD fusion protein group, and the gradation column is for the 1.16 nmol bFGF-PKD-CBD fusion protein group. The "a" means significant difference to the control group, and the "b" means significant difference to the 1.16 nmol bFGF group.

Figure 8:
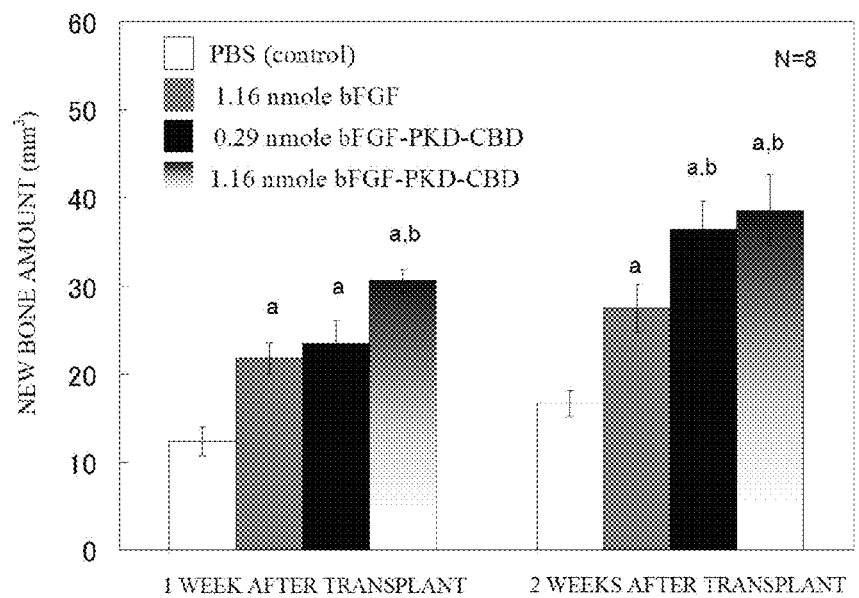
FIG. 8 is a diagram showing the new bone volume in Example 5.

FIG. 8 shows that the new bone amount of the 1.16 nmol bFGF-PKD-CBD fusion protein group after 1 week was significantly larger than the 1.16 nmol bFGF group. After 2 weeks, the amounts of a new bone of both the 0.29 nmol bFGF-PKD-CBD fusion protein group and the 1.16 nmol bFGF-PKD-CBD fusion protein group were significantly larger than the bFGF group. It has been shown that by using the collagen-exposing bone material and the bFGF-PKD-CBD fusion protein according to the present invention, bone formation can be promoted at a low dose for a long term.

Example 6

Thirty-two 10 week-old male Wistar rats were divided to 2 groups of 16 rats each. After reacting 20 mg (weight before collagen-exposing treatment) of the collagen-exposing bone material of diaphysis prepared identically with Example 1, with the bFGF-PKD-CBD, or the bFGF-CBD fusion protein obtained in the production example 3, the product was transplanted on the anterior periosteum of femoral diaphysis. The reaction amount was 0.58 nmol for both the groups.

Figure 9:
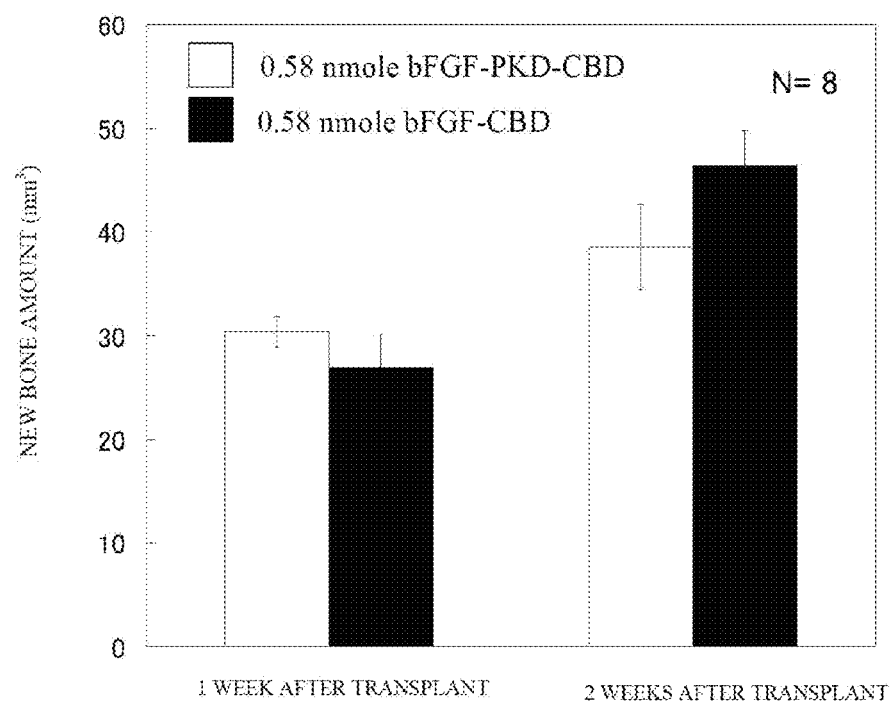
FIG. 9 is a diagram showing the new bone volume in Example 6.

After 1 week and 2 weeks from the transplant, the femora of 8 rats of each group were obtained and the new bone volume was measured using a micro-CT. The results are shown in FIG. 9. The new bone amount after 2 weeks from the transplant tends to be large in the bFGF-CBD fusion protein group. It has been shown that by changing the collagen binding domain the controlled release period or the bone formation amount can be controlled according to the present invention.

Example 7

Eighty 10 week-old male Wistar rats were divided to 4 groups of 20 rats each. A bone graft material formed by reacting a sheet-formed high-density collagen material (collagen fiber density of 640 mg/cm$^3$, 5 mm×5 mm×100 μm), with 0.58 nmol of bFGF, 0.58 nmol of bFGF-CBD fusion protein, or 0.58 nmol of bFGF-PKD-CBD fusion protein respectively was transplanted on the anterior periosteum of femoral diaphysis. A group transplanted with a reaction product of a phosphate buffer solution (PBS) and the high-density collagen material was defined as the control.

Figure 10:
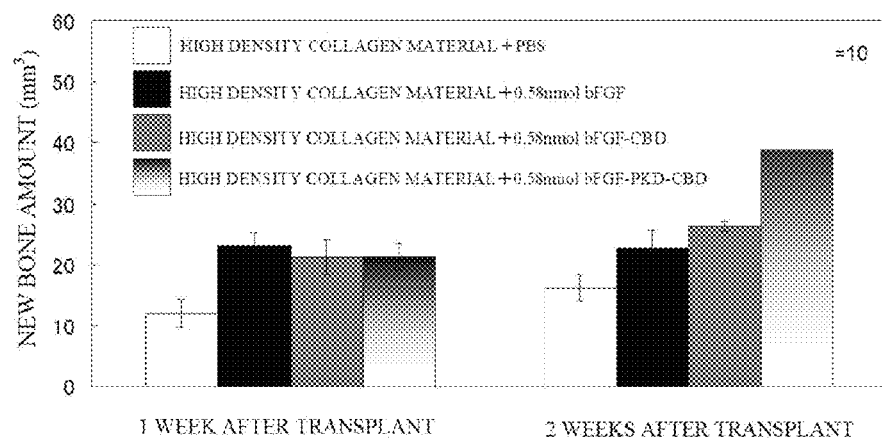
FIG. 10 is a diagram showing the new bone volume in Example 7.

After 1 week and 2 weeks from the transplant, the femora of 10 rats of each group were obtained and the new bone volume was measured using a micro-CT. The results are shown in FIG. 10. The amount of new bone after 1 week from the transplant were the same for the bFGF group, the bFGF-CBD (I) fusion protein, and the bFGF-PKD-CBD (II) fusion protein group, however after 2 weeks the same was significantly high for the bFGF-PKD-CBD (II) fusion protein. According to the present invention, it has been shown that by using the high-density collagen material having high strengths, a graft bone substitute material that can promote bone formation for a long time period can be provided.

Example 8

Six 10 week-old male C57BL/6J mice were divided to 2 groups. To simulate reconstruction of a wide range bone defect suffered after tumor curettage or injury, a 5 mm-bone defect was prepared at the murine femur diaphysis and then a bone was grafted thereto. After bone grafting a bone graft material obtained by reacting the bFGF-PKD-CBD fusion protein prepared as in Example 7 with a sheet-formed high-density collagen material (collagen fiber density of 640 mg/cm$^3$, 5 mm×5 mm×100 μm), was coated thereon. Meanwhile, a group coated with a reaction product of a phosphate buffer solution (PBS) and a sheet-formed high-density collagen material was defined as the control.

Figure 11:
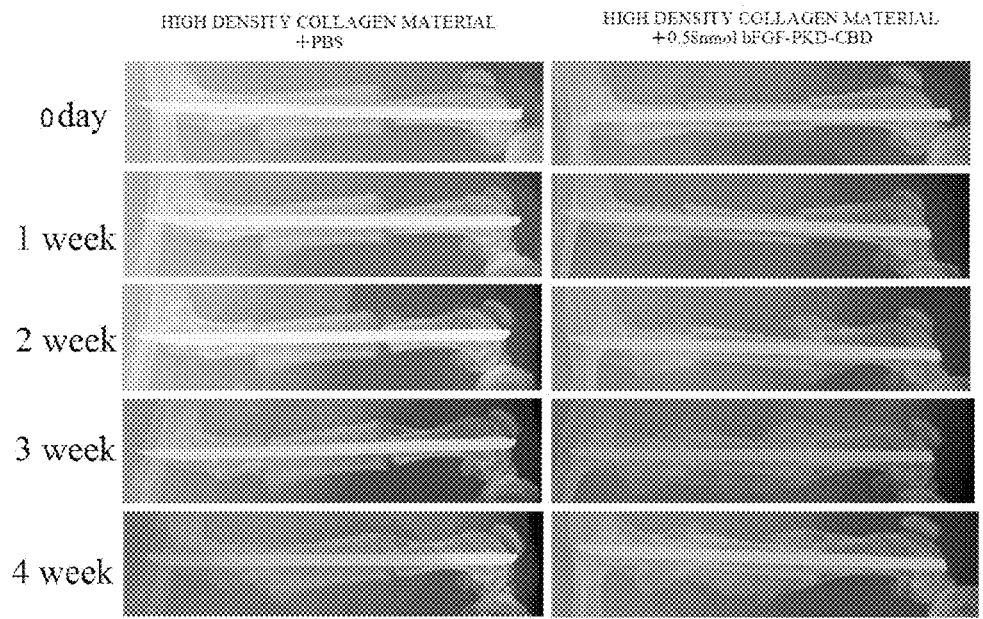
FIG. 11 is a diagram showing a time series change of soft X ray images in Example 8.

The results of temporal change of a mouse of each group are shown in FIG. 11. After 3 weeks from the grafting, vigorous new bone formation is recognizable around the grafted bone in the group coated with a bone graft material, and further that union of the grafted bone and a recipient bed bone was recognized. The above has demonstrated that the bone graft material is useful as a substitute material for an allogeneic cortical bone plate requiring high mechanical strengths.

The present invention is based on Japanese Patent Application No. 2011-108650 filed on 13 May 2011. The description, claims, and drawings of Japanese Patent Application No. 2011-108650 are incorporated herein by reference in its entirety.

INDUSTRIAL APPLICABILITY

A growth factor anchoring type bone graft material of the present invention can be produced easily, and used similarly as a conventional bone graft material. Further, since a growth factor is added, the same is superior in uniting ability of a grafted bone with a recipient bed bone, and therefore useful.

The invention claimed is:

1. A growth factor anchoring type bone graft material, wherein a bone graft substrate exposing at least a collagen fiber is bound to a collagen-binding-site-containing growth factor which comprises a growth factor receptor agonist peptide and a collagen-binding peptide,
wherein the bone graft substrate is a high-density collagen material in a sheet form with a collagen fiber density of 100 to 800 mg/cm$^3$, and the collagen-binding-site-containing growth factor is formed by ligating a basic fibroblast growth factor and the collagen-binding peptide through a polycystic kidney disease I domain of a collagenase.

2. A kit for production of a growth factor anchoring type bone graft material wherein a bone graft substrate exposing at least a collagen fiber is bound to a collagen-binding-site-containing growth factor which comprises a growth factor receptor agonist peptide and a collagen-binding peptide,
wherein the bone graft substrate is a high-density collagen material in a sheet form with a collagen fiber density of 100 to 800 mg/cm$^3$, and the collagen-binding-site-containing growth factor is formed by ligating a basic fibroblast growth factor and the collagen-binding peptide through a polycystic kidney disease I domain of a collagenase, which kit comprises: a solution comprising a collagen-binding-site-containing growth factor formed by ligating a basic fibroblast growth factor and the collagen-binding peptide through a polycystic kidney disease I domain of a collagenase;
and a bone graft substrate which is said high-density collagen material in a sheet form with the collagen fiber density of 100 to 800 mg/cm$^3$.

* * * * *

SEQUENCE LISTING

```
<160> NUMBER OF SEQ ID NOS: 13

<210> SEQ ID NO 1
<211> LENGTH: 3500
<212> TYPE: DNA
<213> ORGANISM: Clostridium histolyticum
<220> FEATURE:
<221> NAME/KEY: CDS
<222> LOCATION: (301)..(3363)

<400> SEQUENCE: 1
aactcctccc gttttaaata gaatctttat aaatttattt tatcctaata ttctcttata      60
tacttaatta aatattaata aaaaattaat gaacaggtat atcttaacaa aaattaaaca     120
aaaattaaac aaatatataa caaatattaa taaataatgt tgacactact aaaaaatggc     180
gttatacttt aataaaaggc ttatataatt cctcaataca aatattcaga taattatgaa     240
aagagcataa atgaaggaat tatgaatttt ttaaaaatta ttttaaatag ggggaagact     300 atg aaa agg aaa tgt tta tct aaa agg ctt atg tta gct ata aca atg     348
```

```
Met Lys Arg Lys Cys Leu Ser Lys Arg Leu Met Leu Ala Ile Thr Met
1               5                   10                  15 gct aca ata ttt aca gtg aac agt aca tta cca att tat gca gct gta      396
Ala Thr Ile Phe Thr Val Asn Ser Thr Leu Pro Ile Tyr Ala Ala Val
        20                  25                  30 gat aaa aat aat gca aca gca gct gta caa aat gaa agt aag agg tat      444
Asp Lys Asn Asn Ala Thr Ala Ala Val Gln Asn Glu Ser Lys Arg Tyr
            35                  40                  45 aca gta tca tat tta aag act tta aat tat tat gac tta gta gat ttg      492
Thr Val Ser Tyr Leu Lys Thr Leu Asn Tyr Tyr Asp Leu Val Asp Leu
    50                  55                  60 ctt gtt aag act gaa att gag aat tta cca gac ctt ttt cag tat agt      540
Leu Val Lys Thr Glu Ile Glu Asn Leu Pro Asp Leu Phe Gln Tyr Ser
65              70                  75                  80 tca gat gca aaa gag ttc tat gga aat aaa act cgt atg agc ttt atc      588
Ser Asp Ala Lys Glu Phe Tyr Gly Asn Lys Thr Arg Met Ser Phe Ile
            85                  90                  95 atg gat gaa att ggt aga agg gca cct cag tat aca gag ata gat cat      636
Met Asp Glu Ile Gly Arg Arg Ala Pro Gln Tyr Thr Glu Ile Asp His
                100                 105                 110 aaa ggt att cct act tta gta gaa gtt gta aga gct gga ttt tac tta      684
Lys Gly Ile Pro Thr Leu Val Glu Val Val Arg Ala Gly Phe Tyr Leu
            115                 120                 125 gga ttc cat aac aag gaa ttg aat gaa ata aac aag agg tct ttt aaa      732
Gly Phe His Asn Lys Glu Leu Asn Glu Ile Asn Lys Arg Ser Phe Lys
        130                 135                 140 gaa agg gta ata cct tct ata tta gca att caa aaa aat cct aat ttt      780
Glu Arg Val Ile Pro Ser Ile Leu Ala Ile Gln Lys Asn Pro Asn Phe
145                 150                 155                 160 aaa cta ggt act gaa gtt caa gat aaa ata gta tct gca aca gga ctt      828
Lys Leu Gly Thr Glu Val Gln Asp Lys Ile Val Ser Ala Thr Gly Leu
                165                 170                 175 tta gct ggt aat gaa aca gcg cct cca gaa gtt gta aat aat ttt aca      876
Leu Ala Gly Asn Glu Thr Ala Pro Pro Glu Val Val Asn Asn Phe Thr
            180                 185                 190 cca ata ctt caa gac tgt ata aag aat ata gac aga tac gct ctt gat      924
Pro Ile Leu Gln Asp Cys Ile Lys Asn Ile Asp Arg Tyr Ala Leu Asp
        195                 200                 205 gat tta aag tca aaa gca tta ttt aat gtt tta gct gca cct acc tat      972
Asp Leu Lys Ser Lys Ala Leu Phe Asn Val Leu Ala Ala Pro Thr Tyr
210                 215                 220 gat ata act gag tat tta aga gct act aaa gaa aaa cca gaa aac act     1020
Asp Ile Thr Glu Tyr Leu Arg Ala Thr Lys Glu Lys Pro Glu Asn Thr
225                 230                 235                 240 cct tgg tat ggt aaa ata gat ggg ttt ata aat gaa ctt aaa aag tta     1068
Pro Trp Tyr Gly Lys Ile Asp Gly Phe Ile Asn Glu Leu Lys Lys Leu
                245                 250                 255 gct ctt tat gga aaa ata aat gat aat aac tct tgg ata ata gat aac     1116
Ala Leu Tyr Gly Lys Ile Asn Asp Asn Asn Ser Trp Ile Ile Asp Asn
            260                 265                 270 ggt ata tat cat ata gca cct tta ggg aag tta cat agc aat aat aaa     1164
Gly Ile Tyr His Ile Ala Pro Leu Gly Lys Leu His Ser Asn Asn Lys
        275                 280                 285 ata gga ata gaa act tta aca gag gtt atg aaa gtt tat cct tat tta     1212
Ile Gly Ile Glu Thr Leu Thr Glu Val Met Lys Val Tyr Pro Tyr Leu
290                 295                 300 agt atg caa cat tta caa tca gca gat caa att aag cgt cat tat gat     1260
Ser Met Gln His Leu Gln Ser Ala Asp Gln Ile Lys Arg His Tyr Asp
305                 310                 315                 320
```

```
tca aaa gat gct gaa gga aac aaa ata cct tta gat aag ttt aaa aag      1308
Ser Lys Asp Ala Glu Gly Asn Lys Ile Pro Leu Asp Lys Phe Lys Lys
            325                 330                 335 gaa gga aaa gaa aaa tac tgt cca aaa act tat aca ttt gat gat gga      1356
Glu Gly Lys Glu Lys Tyr Cys Pro Lys Thr Tyr Thr Phe Asp Asp Gly
            340                 345                 350 aaa gta ata ata aaa gct ggt gct aga gta gaa gaa gaa aaa gtt aaa      1404
Lys Val Ile Ile Lys Ala Gly Ala Arg Val Glu Glu Glu Lys Val Lys
            355                 360                 365 aga cta tac tgg gca tca aag gaa gtt aac tct caa ttc ttt aga gta      1452
Arg Leu Tyr Trp Ala Ser Lys Glu Val Asn Ser Gln Phe Phe Arg Val
        370                 375                 380 tac gga ata gac aaa cca tta gaa gaa ggt aat cca gat gat ata tta      1500
Tyr Gly Ile Asp Lys Pro Leu Glu Glu Gly Asn Pro Asp Asp Ile Leu
385                 390                 395                 400 aca atg gtt atc tac aac agt ccc gaa gaa tat aaa ctc aat agt gtt      1548
Thr Met Val Ile Tyr Asn Ser Pro Glu Glu Tyr Lys Leu Asn Ser Val
                405                 410                 415 cta tac gga tat gat act aat aat ggt ggt atg tat ata gag cca gaa      1596
Leu Tyr Gly Tyr Asp Thr Asn Asn Gly Gly Met Tyr Ile Glu Pro Glu
                420                 425                 430 gga act ttc ttc acc tat gaa aga gaa gct caa gaa agc aca tac aca      1644
Gly Thr Phe Phe Thr Tyr Glu Arg Glu Ala Gln Glu Ser Thr Tyr Thr
            435                 440                 445 tta gaa gaa tta ttt aga cat gaa tat aca cat tat ttg caa gga aga      1692
Leu Glu Glu Leu Phe Arg His Glu Tyr Thr His Tyr Leu Gln Gly Arg
        450                 455                 460 tat gca gtt cca gga caa tgg gga aga aca aaa ctt tat gac aat gat      1740
Tyr Ala Val Pro Gly Gln Trp Gly Arg Thr Lys Leu Tyr Asp Asn Asp
465                 470                 475                 480 aga tta act tgg tat gaa gaa ggt gga gca gaa tta ttt gca ggt tct      1788
Arg Leu Thr Trp Tyr Glu Glu Gly Gly Ala Glu Leu Phe Ala Gly Ser
                485                 490                 495 act aga act tct gga ata tta cca aga aag agt ata gta tca aat att      1836
Thr Arg Thr Ser Gly Ile Leu Pro Arg Lys Ser Ile Val Ser Asn Ile
                500                 505                 510 cat aat aca aca aga aat aat aga tat aag ctt tca gac act gta cat      1884
His Asn Thr Thr Arg Asn Asn Arg Tyr Lys Leu Ser Asp Thr Val His
            515                 520                 525 tct aaa tat ggt gct agt ttt gaa ttc tat aat tat gca tgt atg ttt      1932
Ser Lys Tyr Gly Ala Ser Phe Glu Phe Tyr Asn Tyr Ala Cys Met Phe
530                 535                 540 atg gat tat atg tat aat aaa gat atg ggt ata tta aat aaa cta aat      1980
Met Asp Tyr Met Tyr Asn Lys Asp Met Gly Ile Leu Asn Lys Leu Asn
545                 550                 555                 560 gat ctt gca aaa aat aat gat gtt gat gga tat gat aat tat att aga      2028
Asp Leu Ala Lys Asn Asn Asp Val Asp Gly Tyr Asp Asn Tyr Ile Arg
                565                 570                 575 gat tta agt tct aat tat gct tta aat gat aaa tat caa gat cat atg      2076
Asp Leu Ser Ser Asn Tyr Ala Leu Asn Asp Lys Tyr Gln Asp His Met
                580                 585                 590 cag gag cgc ata gat aat tat gaa aat tta aca gtg cct ttt gta gct      2124
Gln Glu Arg Ile Asp Asn Tyr Glu Asn Leu Thr Val Pro Phe Val Ala
            595                 600                 605 gat gat tat tta gta agg cat gct tat aag aac cct aat gaa att tat      2172
Asp Asp Tyr Leu Val Arg His Ala Tyr Lys Asn Pro Asn Glu Ile Tyr
610                 615                 620 tct gaa ata tct gaa gta gca aaa tta aag gat gct aag agt gaa gtt      2220
Ser Glu Ile Ser Glu Val Ala Lys Leu Lys Asp Ala Lys Ser Glu Val
625                 630                 635                 640
```

| | | | | | | | | | | | | | | | | |
|---|---|---|---|---|---|---|---|---|---|---|---|---|---|---|---|---|
| aag | aaa | tca | caa | tat | ttt | agt | acc | ttt | act | ttg | aga | ggt | agt | tac | aca | 2268 |
| Lys | Lys | Ser | Gln | Tyr | Phe | Ser | Thr | Phe | Thr | Leu | Arg | Gly | Ser | Tyr | Thr | |
| | | | 645 | | | | 650 | | | | | 655 | | | | |
| ggt | gga | gca | tct | aag | ggg | aaa | tta | gaa | gat | caa | aaa | gca | atg | aat | aag | 2316 |
| Gly | Gly | Ala | Ser | Lys | Gly | Lys | Leu | Glu | Asp | Gln | Lys | Ala | Met | Asn | Lys | |
| | | | 660 | | | | 665 | | | | | 670 | | | | |
| ttt | ata | gat | gat | tca | ctt | aag | aaa | tta | gat | acg | tat | tct | tgg | agt | ggg | 2364 |
| Phe | Ile | Asp | Asp | Ser | Leu | Lys | Lys | Leu | Asp | Thr | Tyr | Ser | Trp | Ser | Gly | |
| | | 675 | | | | | 680 | | | | | 685 | | | | |
| tat | aaa | act | tta | act | gct | tat | ttc | act | aat | tat | aaa | gtt | gac | tct | tca | 2412 |
| Tyr | Lys | Thr | Leu | Thr | Ala | Tyr | Phe | Thr | Asn | Tyr | Lys | Val | Asp | Ser | Ser | |
| | 690 | | | | | 695 | | | | | 700 | | | | | |
| aat | aga | gtt | act | tat | gat | gta | gta | ttc | cac | gga | tat | tta | cca | aac | gaa | 2460 |
| Asn | Arg | Val | Thr | Tyr | Asp | Val | Val | Phe | His | Gly | Tyr | Leu | Pro | Asn | Glu | |
| 705 | | | | 710 | | | | 715 | | | | | 720 | | | |
| ggt | gat | tcc | aaa | aat | tca | tta | cct | tat | ggc | aag | atc | aat | gga | act | tac | 2508 |
| Gly | Asp | Ser | Lys | Asn | Ser | Leu | Pro | Tyr | Gly | Lys | Ile | Asn | Gly | Thr | Tyr | |
| | | | | 725 | | | | | 730 | | | | | 735 | | |
| aag | gga | aca | gag | aaa | gaa | aaa | atc | aaa | ttc | tct | agt | gaa | ggc | tct | ttc | 2556 |
| Lys | Gly | Thr | Glu | Lys | Glu | Lys | Ile | Lys | Phe | Ser | Ser | Glu | Gly | Ser | Phe | |
| | | | 740 | | | | | 745 | | | | | 750 | | | |
| gat | cca | gat | ggt | aaa | ata | gtt | tct | tat | gaa | tgg | gat | ttc | gga | gat | ggt | 2604 |
| Asp | Pro | Asp | Gly | Lys | Ile | Val | Ser | Tyr | Glu | Trp | Asp | Phe | Gly | Asp | Gly | |
| | | 755 | | | | | 760 | | | | | 765 | | | | |
| aat | aag | agt | aat | gag | gaa | aat | cca | gag | cat | tca | tat | gac | aag | gta | gga | 2652 |
| Asn | Lys | Ser | Asn | Glu | Glu | Asn | Pro | Glu | His | Ser | Tyr | Asp | Lys | Val | Gly | |
| | 770 | | | | | 775 | | | | | 780 | | | | | |
| act | tat | aca | gtg | aaa | tta | aaa | gtt | act | gat | gac | aag | gga | gaa | tct | tca | 2700 |
| Thr | Tyr | Thr | Val | Lys | Leu | Lys | Val | Thr | Asp | Asp | Lys | Gly | Glu | Ser | Ser | |
| 785 | | | | 790 | | | | 795 | | | | | 800 | | | |
| gta | tct | act | act | act | gca | gaa | ata | aag | gat | ctt | tca | gaa | aat | aaa | ctt | 2748 |
| Val | Ser | Thr | Thr | Thr | Ala | Glu | Ile | Lys | Asp | Leu | Ser | Glu | Asn | Lys | Leu | |
| | | | | 805 | | | | | 810 | | | | | 815 | | |
| cca | gtt | ata | tat | atg | cat | gta | cct | aaa | tcc | gga | gcc | tta | aat | caa | aaa | 2796 |
| Pro | Val | Ile | Tyr | Met | His | Val | Pro | Lys | Ser | Gly | Ala | Leu | Asn | Gln | Lys | |
| | | | 820 | | | | | 825 | | | | | 830 | | | |
| gtt | gtt | ttc | tat | gga | aaa | gga | aca | tat | gac | cca | gat | gga | tct | atc | gca | 2844 |
| Val | Val | Phe | Tyr | Gly | Lys | Gly | Thr | Tyr | Asp | Pro | Asp | Gly | Ser | Ile | Ala | |
| | | 835 | | | | | 840 | | | | | 845 | | | | |
| gga | tat | caa | tgg | gac | ttt | ggt | gat | gga | agt | gat | ttt | agc | agt | gaa | caa | 2892 |
| Gly | Tyr | Gln | Trp | Asp | Phe | Gly | Asp | Gly | Ser | Asp | Phe | Ser | Ser | Glu | Gln | |
| | 850 | | | | | 855 | | | | | 860 | | | | | |
| aac | cca | agc | cat | gta | tat | act | aaa | aaa | ggt | gaa | tat | act | gta | aca | tta | 2940 |
| Asn | Pro | Ser | His | Val | Tyr | Thr | Lys | Lys | Gly | Glu | Tyr | Thr | Val | Thr | Leu | |
| 865 | | | | 870 | | | | | 875 | | | | | 880 | | |
| aga | gta | atg | gat | agt | agt | gga | caa | atg | agt | gaa | aaa | act | atg | aag | att | 2988 |
| Arg | Val | Met | Asp | Ser | Ser | Gly | Gln | Met | Ser | Glu | Lys | Thr | Met | Lys | Ile | |
| | | | | 885 | | | | | 890 | | | | | 895 | | |
| aag | att | aca | gat | ccg | gta | tat | cca | ata | ggc | act | gaa | aaa | gaa | cca | aat | 3036 |
| Lys | Ile | Thr | Asp | Pro | Val | Tyr | Pro | Ile | Gly | Thr | Glu | Lys | Glu | Pro | Asn | |
| | | | 900 | | | | | 905 | | | | | 910 | | | |
| aac | agt | aaa | gaa | act | gca | agt | ggt | cca | ata | gta | cca | ggt | ata | cct | gtt | 3084 |
| Asn | Ser | Lys | Glu | Thr | Ala | Ser | Gly | Pro | Ile | Val | Pro | Gly | Ile | Pro | Val | |
| | | 915 | | | | | 920 | | | | | 925 | | | | |
| agt | gga | acc | ata | gaa | aat | aca | agt | gat | caa | gat | tat | ttc | tat | ttt | gat | 3132 |
| Ser | Gly | Thr | Ile | Glu | Asn | Thr | Ser | Asp | Gln | Asp | Tyr | Phe | Tyr | Phe | Asp | |
| | 930 | | | | | 935 | | | | | 940 | | | | | |
| gtt | ata | aca | cca | gga | gaa | gta | aaa | ata | gat | ata | aat | aaa | tta | ggg | tac | 3180 |
| Val | Ile | Thr | Pro | Gly | Glu | Val | Lys | Ile | Asp | Ile | Asn | Lys | Leu | Gly | Tyr | |

```
                                         -continued
945              950              955              960
gga gga gct act tgg gta gta tat gat gaa aat aat aat gca gta tct   3228
Gly Gly Ala Thr Trp Val Val Tyr Asp Glu Asn Asn Asn Ala Val Ser
                965              970              975 tat gcc act gat gat ggg caa aat tta agt gga aag ttt aag gca gat   3276
Tyr Ala Thr Asp Asp Gly Gln Asn Leu Ser Gly Lys Phe Lys Ala Asp
                980              985              990 aaa cca ggt aga tat tac atc cat ctt tac atg ttt aat ggt agt tat   3324
Lys Pro Gly Arg Tyr Tyr Ile His Leu Tyr Met Phe Asn Gly Ser Tyr
                995             1000             1005 atg cca tat aga att aat ata gaa ggt tca gta gga aga taatatttta   3373
Met Pro Tyr Arg Ile Asn Ile Glu Gly Ser Val Gly Arg
               1010             1015             1020 ttagttgagg taactccata taatagctta gctatttctt atggagttac tttttatatg   3433
taataaaatt ttgacttaaa ttatgatttt ttgctataat ggtttggaaa ttaatgattt   3493
ataattt                                                             3500

<210> SEQ ID NO 2
<211> LENGTH: 6774
<212> TYPE: DNA
<213> ORGANISM: Homo sapiens
<220> FEATURE:
<221> NAME/KEY: misc_feature
<223> OTHER INFORMATION: Homo sapiens fibroblast growth factor 2

<400> SEQUENCE: 2
cggccccaga aacccgagc gagtaggggg cggcgcgcag gagggaggag aactggggc      60 gcgggaggct ggtgggtgtg gggggtggag atgtagaaga tgtgacgccg cggcccggcg   120
ggtgccagat tagcggacgc ggtgcccgcg gttgcaacgg gatcccgggc gctgcagctt   180
gggaggcggc tctccccagg cggcgtccgc ggagacaccc atccgtgaac cccaggtccc   240
gggccgccgg ctcgccgcgc accagggggc ggcggacaga gagcggccg agcggctcga    300 ggctggggga ccgcgggcgc ggccgcgcgc tgccgggcgg gaggctgggg ggccggggcc   360
ggggccgtgc cccggagcgg gtcggaggcc ggggccgggg ccggggacg gcggctcccc    420 gcgcggctcc agcggctcgg ggatcccggc cgggccccgc aggaccatg gcagccggga    480 gcatcaccac gctgcccgcc ttgcccgagg atggcggcag cggcgccttc ccgcccggcc   540
acttcaagga ccccaagcgg ctgtactgca aaaacggggg cttcttcctg cgcatccacc   600
ccgacggccg agttgacggg gtccgggaga gagcgacccc tcacatcaag ctacaacttc   660
aagcagaaga gagaggagtt gtgtctatca aggagtgtg tgctaaccgt tacctggcta   720
tgaaggaaga tggaagatta ctggcttcta aatgtgttac ggatgagtgt tctttttttg   780
aacgattgga atctaataac tacaatactt accggtcaag gaaatacacc agttggtatg   840
tggcactgaa acgaactggg cagtataaac ttggatccaa acaggacct gggcagaaag    900 ctatacttt tcttccaatg tctgctaaga gctgatttta atggccacat ctaatctcat    960
ttcacatgaa agaagaagta tattttagaa atttgttaat gagagtaaaa gaaaataaat   1020
gtgtatagct cagtttggat aattggtcaa acaatttttt atccagtagt aaaatatgta   1080
accattgtcc cagtaaagaa aaataacaaa agttgtaaaa tgtatattct ccctttata    1140 ttgcatctgc tgttacccag tgaagcttac ctagagcaat gatcttttc acgcatttgc    1200 tttattcgaa aagaggcttt taaaatgtgc atgtttagaa acaaaatttc ttcatggaaa   1260
tcatatacat tagaaaatca cagtcagatg tttaatcaat ccaaaatgtc cactatttct   1320
```

```
tatgtcattc gttagtctac atgtttctaa acatataaat gtgaatttaa tcaattcctt    1380
tcatagttt  ataattctct ggcagttcct tatgatagag tttataaaac agtcctgtgt    1440
aaactgctgg aagttcttcc acagtcaggt caattttgtc aaacccttct ctgtacccat    1500
acagcagcag cctagcaact ctgctggtga tgggagttgt attttcagtc ttcgccaggt    1560
cattgagatc catccactca catcttaagc attcttcctg gcaaaatt  atggtgaatg    1620
aatatggctt taggcggcag atgatataca tatctgactt cccaaaagct ccaggatttg    1680
tgtgctgttg ccgaatactc aggacggacc tgaattctga ttttatacca gtctcttcaa    1740
aaacttctcg aaccgctgtg tctcctacgt aaaaaaagag atgtacaaat caataataat    1800
tacacttta  gaaactgtat catcaaagat tttcagttaa agtagcatta tgtaaaggct    1860
caaaacatta ccctaacaaa gtaaagtttt caatacaaat tctttgcctt gtggatatca    1920
agaaatccca aaatatttc  ttaccactgt aaattcaaga agcttttgaa atgctgaata    1980
tttctttggc tgctacttgg aggcttatct acctgtacat ttttgggtc  agctcttttt    2040
aacttcttgc tgctcttttt cccaaaaggt aaaaatatag attgaaaagt taaacatttt    2100
tgcatggctg cagttccttt gtttcttgag ataagattcc aaagaactta gattcatttc    2160
ttcaacaccg aaatgctgga ggtgtttgat cagttttcaa gaaacttgga atataaataa    2220
ttttataatt caacaaaggt tttcacattt tataaggttg attttcaat  taaatgcaaa    2280
tttgtgtggc aggattttta ttgccattaa catattttg  tggctgcttt ttctacacat    2340
ccagatggtc cctctaactg ggctttctct aattttgtga tgttctgtca ttgtctccca    2400
aagtatttag gagaagccct ttaaaaagct gccttcctct accactttgc tggaaagctt    2460
cacaattgtc acagacaaag atttttgttc caatactcgt tttgcctcta ttttcttgt     2520
ttgtcaaata gtaaatgata tttgcccttg cagtaattct actggtgaaa acatgcaaa     2580
gaagaggaag tcacagaaac atgtctcaat tcccatgtgc tgtgactgta gactgtctta    2640
ccatagactg tcttacccat cccctggata tgctcttgtt ttttccctct aatagctatg    2700
gaaagatgca tagaaagagt ataatgtttt aaaacataag gcattcgtct gccatttttc    2760
aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt    3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt tccttaata  agaaaagtaa ttttactct  gatgtgcaat    3180
acatttgtta ttaaatttat tatttaagat ggtagcacta gtcttaaatt gtataaaata    3240
tcccctaaca tgtttaaatg tccatttta  ttcattatgc tttgaaaaat aattatgggg    3300
aaatacatgt ttgttattaa atttattatt aagatagta  gcactagtct taaatttgat    3360
ataacatctc ctaacttgtt taaatgtcca ttttattct  ttatgtttga aaataaatta    3420
tggggatcct atttagctct tagtaccact aatcaaagt  tcggcatgta gctcatgatc    3480
tatgctgttt ctatgtcgtg aagcaccgg  atggggtag  tgagcaaatc tgccctgctc    3540
agcagtcacc atagcagctg actgaaaatc agcactgcct gagtagtttt gatcagttta    3600
acttgaatca ctaactgact gaaaattgaa tgggcaaata agtgctttg  tctccagagt    3660
atgcgggaga cccttccacc tcaagatgga tatttcttcc ccaaggattt caagatgaat    3720
```

-continued

```
tgaaattttt aatcaagata gtgtgcttta ttctgttgta tttttttatta ttttaatata    3780
ctgtaagcca aactgaaata acatttgctg ttttataggt ttgaagaaca taggaaaaac    3840
taagaggttt tgttttatt tttgctgatg aagagatatg tttaaatatg ttgtattgtt     3900
ttgtttagtt acaggacaat aatgaaatgg agtttatatt tgttatttct attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgattttt     4140
aagaaggcag tttgtcaatt ttaatcttgt ggatacctt atactcttag ggtattattt     4200
tatacaaaag ccttgaggat tgcattctat tttctatatg accctcttga tatttaaaaa    4260
acactatgga taacaattct tcatttacct agtattatga agaatgaag gagttcaaac     4320
aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt tcatttcta     4560
gctgctttca gggttttatg aattttcagg caaagcttta atttatacta agcttaggaa    4620
gtatggctaa tgccaacggc agttttttc ttcttaattc cacatgactg aggcatatat     4680
gatctctggg taggtgagtt gttgtgacaa ccacaagcac ttttttttt tttaaagaaa     4740
aaaaggtagt gaattttaa tcatctggac tttaagaagg attctggagt atacttaggc     4800
ctgaaattat atatatttgg cttggaaatg tgttttctt caattacatc tacaagtaag     4860
tacagctgaa attcagagga cccataagag ttcacatgaa aaaaatcaat ttatttgaaa    4920
aggcaagatg caggagagag gaagccttgc aaacctgcag actgctttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
acaccactac aaaatcatct tttatatcaa cagaagaata agcataaact aagcaaaagg    5160
tcaataagta cctgaaacca agattggcta gagatatatc ttaatgcaat ccattttctg    5220
atggattgtt acgagttggc tatataatgt atgtatggta ttttgatttg tgtaaaagtt    5280
ttaaaaatca agctttaagt acatggacat ttttaaataa aatatttaaa gacaatttag    5340
aaaattgcct taatatcatt gttggctaaa tagaataggg gacatgcata ttaaggaaaa    5400
ggtcatggag aaataatatt ggtatcaaac aaatacattg atttgtcatg atacacattg    5460
aatttgatcc aatagtttaa ggaataggta ggaaaatttg gtttctattt ttcgatttcc    5520
tgtaaatcag tgacataaat aattcttagc ttattttata tttccttgtc ttaaatactg    5580
agctcagtaa gttgtgttag gggattattt ctcagttgag actttcttat atgacatttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat tgttttctc atagtttaat    5820
tccaacaaca atattagtcg tatccaaaat aaccttaat gctaaacttt actgatgtat     5880
atccaaagct tctcattttc agacagatta atccagaagc agtcataaac agaagaatag    5940
gtggtatgtt cctaatgata ttatttctac taatggaata aactgtaata ttagaaatta    6000
tgctgctaat tatatcagct ctgaggtaat ttctgaaatg ttcagactca gtcggaacaa    6060
```

```
attggaaaat ttaaatttt attcttagct ataaagcaag aaagtaaaca cattaatttc   6120
ctcaacattt ttaagccaat taaaaatata aaagatacac accaatatct tcttcaggct   6180
ctgacaggcc tcctggaaac ttccacatat ttttcaactg cagtataaag tcagaaaata   6240
aagttaacat aactttcact aacacacaca tatgtagatt tcacaaaatc cacctataat   6300
tggtcaaagt ggttgagaat atattttta gtaattgcat gcaaaatttt tctagcttcc    6360 atccttctc cctcgtttct tctttttttg ggggagctgg taactgatga atcttttcc     6420 cacctttct cttcaggaaa tataagtggt tttgtttggt taacgtgata cattctgtat    6480
gaatgaaaca ttggagggaa acatctactg aatttctgta atttaaaata tttttgctgct  6540 agttaactat gaacagatag aagaatctta cagatgctgc tataaataag tagaaaatat   6600
aaatttcatc actaaaatat gctattttaa aatctatttc ctatattgta tttctaatca   6660
gatgtattac tcttattatt tctattgtat gtgttaatga ttttatgtaa aaatgtaatt   6720
gcttttcatg agtagtatga ataaaattga ttagtttgtg ttttcttgtc tccc         6774
```

<210> SEQ ID NO 3
<211> LENGTH: 4801
<212> TYPE: DNA
<213> ORGANISM: Rattus norvegicus
<220> FEATURE:
<221> NAME/KEY: CDS
<222> LOCATION: (389)..(3787)

<400> SEQUENCE: 3

```
caaaaggaga agccatcagg gaaggaatcc tatctgcata tttcgtcttt agccccatcc    60
ctcattcccg gtggggtttg aactttcca tcaattcttt ccctgtctca tttctctttg    120
agcctttgcc tagctgtgcc tgtcacagcg agaaatcagt caccctccgc cttccagcac   180
tcttaggctc tgagaaattt ggcatacggg tgtcaggtat taaaacagct aaataaaaga   240
tgccctgggg ctgaaggcca gcgtggctgg aagttctggg ggtcagaagc ctgactccgc   300
ctgctccaag ctctagcaat ttaagtcacc cgggggtttt ttgttttggt ttggtttggt   360
ttttcttgac cttagaacca ccgagacc atg ctg ttc tcg ctc acc ttc ctg     412
                                 Met Leu Phe Ser Leu Thr Phe Leu
                                   1               5 tcg gtg ttt tta aag att act gta ctc agt gtc aca gca cag cag acc    460
Ser Val Phe Leu Lys Ile Thr Val Leu Ser Val Thr Ala Gln Gln Thr
     10                  15                  20 agg aac tgt cag tca ggt cct ctc gag aga agc ggg act acc acg tat    508
Arg Asn Cys Gln Ser Gly Pro Leu Glu Arg Ser Gly Thr Thr Thr Tyr
 25                  30                  35                  40 gcc gcc gcc ggt cct ccc agg ttc ctg att ttc tta caa gga aac agc    556
Ala Ala Ala Gly Pro Pro Arg Phe Leu Ile Phe Leu Gln Gly Asn Ser
                     45                  50                  55 atc ttt cgg att aac aca gat gga aca aat cac cag caa ttg gtg gtg    604
Ile Phe Arg Ile Asn Thr Asp Gly Thr Asn His Gln Gln Leu Val Val
             60                  65                  70 gat gcc ggc gtc tca gtg gtc atg gat ttt cat tac aag gaa gag aga    652
Asp Ala Gly Val Ser Val Val Met Asp Phe His Tyr Lys Glu Glu Arg
         75                  80                  85 ctc tat tgg gtg gat tta gaa aga caa ctt ttg caa aga gtt ttc ttt    700
Leu Tyr Trp Val Asp Leu Glu Arg Gln Leu Leu Gln Arg Val Phe Phe
     90                  95                 100 aat ggg tca gga caa gag aca gtg tgc aag gtg gat aag aat gtg tct    748
Asn Gly Ser Gly Gln Glu Thr Val Cys Lys Val Asp Lys Asn Val Ser
105                 110                 115                 120
```

| | | |
|---|---|---|
| ggg ctg gcc ata aac tgg ata gat ggg gag att ctc cgg acg gac cga<br>Gly Leu Ala Ile Asn Trp Ile Asp Gly Glu Ile Leu Arg Thr Asp Arg<br>                     125                            130                     135 | | 796 |
| tgg aag gga gtc atc aca gta aca gat atg aac ggg aac aat tcc cgt<br>Trp Lys Gly Val Ile Thr Val Thr Asp Met Asn Gly Asn Asn Ser Arg<br>                     140                            145                     150 | | 844 |
| gtt ctt ctg agt tcc tta aaa cgt cct gca aat ata tta gtg gat cca<br>Val Leu Leu Ser Ser Leu Lys Arg Pro Ala Asn Ile Leu Val Asp Pro<br>            155                            160                            165 | | 892 |
| aca gag agg ttg ata ttt tgg tct tca gtg gtg act ggc aac ctt cac<br>Thr Glu Arg Leu Ile Phe Trp Ser Ser Val Val Thr Gly Asn Leu His<br>            170                            175                    180 | | 940 |
| aga gca gat ctc ggg ggt atg gat gta aaa aca ctg ctg gag gca cca<br>Arg Ala Asp Leu Gly Gly Met Asp Val Lys Thr Leu Leu Glu Ala Pro<br>185                            190                            195                    200 | | 988 |
| gag agg ata tca gtg ctg att ctg gat atc ctg gac aaa agg ctc ttc<br>Glu Arg Ile Ser Val Leu Ile Leu Asp Ile Leu Asp Lys Arg Leu Phe<br>                       205                            210                     215 | | 1036 |
| tgg gct cag gac ggt aga gaa gga agc cac ggt tac att cac tcc tgt<br>Trp Ala Gln Asp Gly Arg Glu Gly Ser His Gly Tyr Ile His Ser Cys<br>                     220                            225                    230 | | 1084 |
| gac tat aac ggt ggc tcc atc cat cat atc aga cat caa gca cgg cac<br>Asp Tyr Asn Gly Gly Ser Ile His His Ile Arg His Gln Ala Arg His<br>            235                            240                            245 | | 1132 |
| gat ttg ctt act atg gcc att ttc ggt gac aag atc tta tac tca gca<br>Asp Leu Leu Thr Met Ala Ile Phe Gly Asp Lys Ile Leu Tyr Ser Ala<br>            250                            255                    260 | | 1180 |
| ctg aaa gag aag gcg att tgg ata gcc gac aaa cac act ggg aag aat<br>Leu Lys Glu Lys Ala Ile Trp Ile Ala Asp Lys His Thr Gly Lys Asn<br>265                            270                            275                    280 | | 1228 |
| gtg gtt cga gtt aac ctc gat cca gcc tct gtg ccg cca aga gaa ctg<br>Val Val Arg Val Asn Leu Asp Pro Ala Ser Val Pro Pro Arg Glu Leu<br>                     285                            290                     295 | | 1276 |
| aga gtc gtg cac cta cat gca cag ccc ggg aca gag aac cgt gct cag<br>Arg Val Val His Leu His Ala Gln Pro Gly Thr Glu Asn Arg Ala Gln<br>            300                            305                    310 | | 1324 |
| gcc tct gac tcc gaa cga tgc aaa cag aga aga gga cag tgt ctc tac<br>Ala Ser Asp Ser Glu Arg Cys Lys Gln Arg Arg Gly Gln Cys Leu Tyr<br>                     315                            320                    325 | | 1372 |
| agt ctc tct gag cga gac ccc aac tca gac tcg tcg gca tgc gct gaa<br>Ser Leu Ser Glu Arg Asp Pro Asn Ser Asp Ser Ser Ala Cys Ala Glu<br>            330                            335                    340 | | 1420 |
| ggc tat acg tta agc cga gac cgg aag tac tgc gaa gat gtc aat gag<br>Gly Tyr Thr Leu Ser Arg Asp Arg Lys Tyr Cys Glu Asp Val Asn Glu<br>345                            350                            355                    360 | | 1468 |
| tgt gcc ttg cag aat cac ggc tgt act ctt ggg tgt gaa aac atc cct<br>Cys Ala Leu Gln Asn His Gly Cys Thr Leu Gly Cys Glu Asn Ile Pro<br>                     365                            370                    375 | | 1516 |
| gga tcc tat tac tgc aca tgc cct aca ggc ttt gtt ctg ctt cct gat<br>Gly Ser Tyr Tyr Cys Thr Cys Pro Thr Gly Phe Val Leu Leu Pro Asp<br>                     380                            385                    390 | | 1564 |
| ggg aaa cga tgt cac gaa ctt gtt gcc tgt cca ggc aac aga tca gag<br>Gly Lys Arg Cys His Glu Leu Val Ala Cys Pro Gly Asn Arg Ser Glu<br>                     395                            400                    405 | | 1612 |
| tgt agc cat gat tgc atc ctg aca tca gat ggt cct ctg tgc atc tgt<br>Cys Ser His Asp Cys Ile Leu Thr Ser Asp Gly Pro Leu Cys Ile Cys<br>            410                            415                    420 | | 1660 |
| cca gca ggt tca gtg ctc gga aaa gat ggg aag aca tgc act ggt tgt<br>Pro Ala Gly Ser Val Leu Gly Lys Asp Gly Lys Thr Cys Thr Gly Cys<br>425                            430                            435                    440 | | 1708 |

| | | |
|---|---|---|
| tcc ttc tcc gat aat ggt gga tgc agc cag atc tgc ctt cct ctc agc<br>Ser Phe Ser Asp Asn Gly Gly Cys Ser Gln Ile Cys Leu Pro Leu Ser<br>445 450 455 | | 1756 |
| cta gca tcc tgg gaa tgt gat tgc ttt cct ggg tac gac cta caa ttg<br>Leu Ala Ser Trp Glu Cys Asp Cys Phe Pro Gly Tyr Asp Leu Gln Leu<br>460 465 470 | | 1804 |
| gac cga aag agc tgt gca gct tcc atg gga ccg cag cca ttt tta ctg<br>Asp Arg Lys Ser Cys Ala Ala Ser Met Gly Pro Gln Pro Phe Leu Leu<br>475 480 485 | | 1852 |
| ttt gca aat tcc cag gac ata cga cac atg cat ttt gat gga aca gac<br>Phe Ala Asn Ser Gln Asp Ile Arg His Met His Phe Asp Gly Thr Asp<br>490 495 500 | | 1900 |
| tac aaa act ctg ctc agc cgg cag atg gga atg gtt ttt gcc ttg gat<br>Tyr Lys Thr Leu Leu Ser Arg Gln Met Gly Met Val Phe Ala Leu Asp<br>505 510 515 520 | | 1948 |
| tat gac ccc gtg gaa agc aag ata tat ttt gca cag aca gcc ctg aag<br>Tyr Asp Pro Val Glu Ser Lys Ile Tyr Phe Ala Gln Thr Ala Leu Lys<br>525 530 535 | | 1996 |
| tgg ata gag agg gct aat ctg gat ggc tcc cag cga gaa aga cgg atc<br>Trp Ile Glu Arg Ala Asn Leu Asp Gly Ser Gln Arg Glu Arg Arg Ile<br>540 545 550 | | 2044 |
| acg gaa gga gta gac acg cca gaa ggt ctt gcc gtg gac tgg att ggc<br>Thr Glu Gly Val Asp Thr Pro Glu Gly Leu Ala Val Asp Trp Ile Gly<br>555 560 565 | | 2092 |
| cgg aga atc tac tgg acg gac agt ggg aag tct gtc att gaa ggg agt<br>Arg Arg Ile Tyr Trp Thr Asp Ser Gly Lys Ser Val Ile Glu Gly Ser<br>570 575 580 | | 2140 |
| gat ttg agc ggg aag cat cat caa ata atc atc aaa gag agc atc tca<br>Asp Leu Ser Gly Lys His His Gln Ile Ile Ile Lys Glu Ser Ile Ser<br>585 590 595 600 | | 2188 |
| agg cca cga gga ata gct gtg cat cca aag gcc agg aga cta ttc tgg<br>Arg Pro Arg Gly Ile Ala Val His Pro Lys Ala Arg Arg Leu Phe Trp<br>605 610 615 | | 2236 |
| acg gac acg ggg atg tct ccg cgg att gaa agc tct tcc ctt caa ggt<br>Thr Asp Thr Gly Met Ser Pro Arg Ile Glu Ser Ser Ser Leu Gln Gly<br>620 625 630 | | 2284 |
| tct gac cgg acg ctg ata gcc agc tct aat cta ctg gaa ccc agt gga<br>Ser Asp Arg Thr Leu Ile Ala Ser Ser Asn Leu Leu Glu Pro Ser Gly<br>635 640 645 | | 2332 |
| atc gcg att gac tac tta aca gac act ttg tac tgg tgt gac acc aag<br>Ile Ala Ile Asp Tyr Leu Thr Asp Thr Leu Tyr Trp Cys Asp Thr Lys<br>650 655 660 | | 2380 |
| ctg tct gtg att gaa atg gcc gat cta gat ggt tcc aaa cgc gcc aga<br>Leu Ser Val Ile Glu Met Ala Asp Leu Asp Gly Ser Lys Arg Arg Arg<br>665 670 675 680 | | 2428 |
| ctt acc cag aac gat gta ggt cac cca ttc tct cta gct gtg ttt gag<br>Leu Thr Gln Asn Asp Val Gly His Pro Phe Ser Leu Ala Val Phe Glu<br>685 690 695 | | 2476 |
| gat cac gtg tgg ttc tcg gat tgg gct atc cca tcg gta ata agg gtg<br>Asp His Val Trp Phe Ser Asp Trp Ala Ile Pro Ser Val Ile Arg Val<br>700 705 710 | | 2524 |
| aac aag agg act ggt caa aac agg gta cgt ctc cga ggc agc atg ctg<br>Asn Lys Arg Thr Gly Gln Asn Arg Val Arg Leu Arg Gly Ser Met Leu<br>715 720 725 | | 2572 |
| aag ccc tcg tca ctg gtt gtg gtc cac cca ttg gca aaa cca ggt gca<br>Lys Pro Ser Ser Leu Val Val Val His Pro Leu Ala Lys Pro Gly Ala<br>730 735 740 | | 2620 |
| gac ccc tgc tta cac agg aat gga ggc tgt gaa cac atc tgc caa gag<br>Asp Pro Cys Leu His Arg Asn Gly Gly Cys Glu His Ile Cys Gln Glu | | 2668 |

-continued

| | | |
|---|---|---|
| agc ctg ggc acg gct cag tgt ctg tgt cgg gaa gga ttc gtg aag gcc<br>Ser Leu Gly Thr Ala Gln Cys Leu Cys Arg Glu Gly Phe Val Lys Ala<br>745                      750                      755                    760 | 2716 | |

```
                   745                 750                 755                 760 agc ctg ggc acg gct cag tgt ctg tgt cgg gaa gga ttc gtg aag gcc      2716
           Ser Leu Gly Thr Ala Gln Cys Leu Cys Arg Glu Gly Phe Val Lys Ala
                           765                 770                 775 cca gat ggg aaa atg tgt ctc act cgg aag gat gat cag ata ctg gcc      2764
           Pro Asp Gly Lys Met Cys Leu Thr Arg Lys Asp Asp Gln Ile Leu Ala
                       780                 785                 790 ggt gac aat gct gat ctt agt aaa gag gtg gca tcg ttg gac aac tcc      2812
           Gly Asp Asn Ala Asp Leu Ser Lys Glu Val Ala Ser Leu Asp Asn Ser
                   795                 800                 805 cct aag gct tat gta cca gac gat gat agg aca gag tcc tcc aca cta      2860
           Pro Lys Ala Tyr Val Pro Asp Asp Asp Arg Thr Glu Ser Ser Thr Leu
               810                 815                 820 gtg gct gag atc atg gtg tca ggg ctg aac tat gaa gat gac tgc ggc      2908
           Val Ala Glu Ile Met Val Ser Gly Leu Asn Tyr Glu Asp Asp Cys Gly
           825                 830                 835                 840 cct ggt ggg tgt ggc agc cat gcc cac tgt att tca gag gga gag gca      2956
           Pro Gly Gly Cys Gly Ser His Ala His Cys Ile Ser Glu Gly Glu Ala
                           845                 850                 855 gct gtg tgt cag tgt ttg aaa gga ttt gct ggc gat gga aac ctg tgt      3004
           Ala Val Cys Gln Cys Leu Lys Gly Phe Ala Gly Asp Gly Asn Leu Cys
                       860                 865                 870 tct gat ata gac gaa tgt gag ctg ggt agc tca gac tgt cct ccc acc      3052
           Ser Asp Ile Asp Glu Cys Glu Leu Gly Ser Ser Asp Cys Pro Pro Thr
                   875                 880                 885 tcg tcc agg tgc atc aac acc gaa ggt ggc tat gtc tgc caa tgc tca      3100
           Ser Ser Arg Cys Ile Asn Thr Glu Gly Gly Tyr Val Cys Gln Cys Ser
               890                 895                 900 gaa ggc tac gag gga gat ggg atc tac tgt ctc gac gtt gat gag tgc      3148
           Glu Gly Tyr Glu Gly Asp Gly Ile Tyr Cys Leu Asp Val Asp Glu Cys
           905                 910                 915                 920 cag cag ggg tcg cac ggc tgc agc gag aat gcc acc tgc acc aac acg      3196
           Gln Gln Gly Ser His Gly Cys Ser Glu Asn Ala Thr Cys Thr Asn Thr
                           925                 930                 935 gag gga ggc tac aac tgc acc tgt gca ggc tgc cca tca gca cct gga      3244
           Glu Gly Gly Tyr Asn Cys Thr Cys Ala Gly Cys Pro Ser Ala Pro Gly
                       940                 945                 950 ctg cct tgc cct gac tct acc tca ccc tct ctc ctt gga aaa gat ggc      3292
           Leu Pro Cys Pro Asp Ser Thr Ser Pro Ser Leu Leu Gly Lys Asp Gly
                   955                 960                 965 tgc cac tgg gtc cga aac agt aac aca gga tgc ccg ccg tcg tac gat      3340
           Cys His Trp Val Arg Asn Ser Asn Thr Gly Cys Pro Pro Ser Tyr Asp
               970                 975                 980 ggg tac tgc ctc aat ggt ggc gtg tgc atg tat gtt gaa tcc gtg gac      3388
           Gly Tyr Cys Leu Asn Gly Gly Val Cys Met Tyr Val Glu Ser Val Asp
           985                 990                 995                 1000 cgc tac gtg tgc aac tgt gtc att ggc tat att gga gaa cga tgt          3433
           Arg Tyr Val Cys Asn Cys Val Ile Gly Tyr Ile Gly Glu Arg Cys
                           1005                1010                1015 cag cac cga gac tta cgt tgg tgg aag ctg cgc cat gct gac tac          3478
           Gln His Arg Asp Leu Arg Trp Trp Lys Leu Arg His Ala Asp Tyr
                       1020                1025                1030 ggg cag agg cac gac atc act gtg gtg tct gtc tgt gtg gtg gcg          3523
           Gly Gln Arg His Asp Ile Thr Val Val Ser Val Cys Val Val Ala
                   1035                1040                1045 ctg gcc ctg ctg ctc ctc tta ggg atg tgg ggg act tac tac tac          3568
           Leu Ala Leu Leu Leu Leu Leu Gly Met Trp Gly Thr Tyr Tyr Tyr
               1050                1055                1060 agg act cgg aag cag cta tca gag agc tca aag aag cct tcc gaa          3613
```

| | | | | | | | | | | | | |
|---|---|---|---|---|---|---|---|---|---|---|---|---|
|Arg|Thr|Arg|Lys|Gln|Leu|Ser|Glu|Ser|Ser|Lys|Lys|Pro|Ser|Glu|
| | | |1065| | | |1070| | | |1075| | | |

```
gag tca agc agc aac gtg agc agt aac ggg cct gac agc agc ggg      3658
Glu Ser Ser Ser Asn Val Ser Ser Asn Gly Pro Asp Ser Ser Gly
            1080                1085                1090 gct ggg gtg tct tct ggt ccc caa cct tgg ttt gtg gtc cta gag      3703
Ala Gly Val Ser Ser Gly Pro Gln Pro Trp Phe Val Val Leu Glu
            1095                1100                1105 gaa cac caa cag ccc aag aat ggg cgt ctg cct gcc gct ggc acg      3748
Glu His Gln Gln Pro Lys Asn Gly Arg Leu Pro Ala Ala Gly Thr
            1110                1115                1120 aac ggc gca gta gta gag gct ggc ctg tct tcc tcc ctg taactcgggc   3797
Asn Gly Ala Val Val Glu Ala Gly Leu Ser Ser Ser Leu
            1125                1130 cagtgcacct gacttcctgg agacagaagc cccgaatata tgagatgggc acagagcaaa  3857
gctgctggat tccaccatca aatgacaaag daccccagga aatggagggg aaccccccact  3917
taccctccta cagggaatgg cctctagctg tgtgggctga aagaagctg cattctctcc   3977
agtcagctaa tggatcgagt caacaagggg cctcagacct gccccagcaa acagagccag   4037
ttctgtagaa actgggagca gacagaaggt accgaaagtg aaatagcaaa ccaggctgaa   4097
gggtggtaga gcggcagatc tggtactcct gtctccacgg ctaatcactg ctcagggtcc   4157
tgaagataac tgcatagctg catagctgat agccgcgact tctgcttctt gcttcaagca   4217
gtcccgttga agacgatcaa aagagaagtg gagaaaaatc atcagaaacc gaagtcaaga   4277
cggttcacgt gtgtaagctg tgtccttcct acccctggac tgttgggctc ttttccttgt   4337
tgtctcagaa gaaatgggtt aaagcaggcg atcacatgct ttgttgattg cacagtagat   4397
gatatgatct acatagatct tagctcactc tcacggaaag gctggaacat tatagatgct   4457
gcaagataca ctgcaagtgt ggcccctgct cataattttg ccttctgaat tgtgattagt   4517
gaaaataatt gtaacttaga gtccgattta ttcagaatca gagcattatt tttatactat   4577
gaaaatcttt gaatgaagat atttaacttt aaaaacattt cctaagagac aacagtgttt   4637
cttaatcatt gtcttttctt cttgcagtct ttcccagtga aaacggtaaa ttctgctgtt   4697
tgcatagaat ctttaactta ttttaagat atgagattgt aaacaaattg cttgatttat   4757
ttcaatcaat ttattctaat tatttaaata aaatcaccccc taag                  4801
```

<210> SEQ ID NO 4
<211> LENGTH: 1133
<212> TYPE: PRT
<213> ORGANISM: Rattus norvegicus

<400> SEQUENCE: 4

Met Leu Phe Ser Leu Thr Phe Leu Ser Val Phe Leu Lys Ile Thr Val
1               5                   10                  15

Leu Ser Val Thr Ala Gln Gln Thr Arg Asn Cys Gln Ser Gly Pro Leu
            20                  25                  30

Glu Arg Ser Gly Thr Thr Thr Tyr Ala Ala Ala Gly Pro Pro Arg Phe
        35                  40                  45

Leu Ile Phe Leu Gln Gly Asn Ser Ile Phe Arg Ile Asn Thr Asp Gly
    50                  55                  60

Thr Asn His Gln Gln Leu Val Val Asp Ala Gly Val Ser Val Val Met
65                  70                  75                  80

Asp Phe His Tyr Lys Glu Glu Arg Leu Tyr Trp Val Asp Leu Glu Arg
                85                  90                  95

```
Gln Leu Leu Gln Arg Val Phe Phe Asn Gly Ser Gly Gln Glu Thr Val
            100                 105                 110

Cys Lys Val Asp Lys Asn Val Ser Gly Leu Ala Ile Asn Trp Ile Asp
        115                 120                 125

Gly Glu Ile Leu Arg Thr Asp Arg Trp Lys Gly Val Ile Thr Val Thr
    130                 135                 140

Asp Met Asn Gly Asn Asn Ser Arg Val Leu Leu Ser Ser Leu Lys Arg
145                 150                 155                 160

Pro Ala Asn Ile Leu Val Asp Pro Thr Glu Arg Leu Ile Phe Trp Ser
                165                 170                 175

Ser Val Val Thr Gly Asn Leu His Arg Ala Asp Leu Gly Gly Met Asp
            180                 185                 190

Val Lys Thr Leu Leu Glu Ala Pro Glu Arg Ile Ser Val Leu Ile Leu
        195                 200                 205

Asp Ile Leu Asp Lys Arg Leu Phe Trp Ala Gln Asp Gly Arg Glu Gly
    210                 215                 220

Ser His Gly Tyr Ile His Ser Cys Asp Tyr Asn Gly Gly Ser Ile His
225                 230                 235                 240

His Ile Arg His Gln Ala Arg His Asp Leu Leu Thr Met Ala Ile Phe
                245                 250                 255

Gly Asp Lys Ile Leu Tyr Ser Ala Leu Lys Glu Lys Ala Ile Trp Ile
            260                 265                 270

Ala Asp Lys His Thr Gly Lys Asn Val Val Arg Val Asn Leu Asp Pro
        275                 280                 285

Ala Ser Val Pro Pro Arg Glu Leu Arg Val Val His Leu His Ala Gln
    290                 295                 300

Pro Gly Thr Glu Asn Arg Ala Gln Ala Ser Asp Ser Glu Arg Cys Lys
305                 310                 315                 320

Gln Arg Arg Gly Gln Cys Leu Tyr Ser Leu Ser Glu Arg Asp Pro Asn
                325                 330                 335

Ser Asp Ser Ser Ala Cys Ala Glu Gly Tyr Thr Leu Ser Arg Asp Arg
            340                 345                 350

Lys Tyr Cys Glu Asp Val Asn Glu Cys Ala Leu Gln Asn His Gly Cys
        355                 360                 365

Thr Leu Gly Cys Glu Asn Ile Pro Gly Ser Tyr Tyr Cys Thr Cys Pro
    370                 375                 380

Thr Gly Phe Val Leu Leu Pro Asp Gly Lys Arg Cys His Glu Leu Val
385                 390                 395                 400

Ala Cys Pro Gly Asn Arg Ser Glu Cys Ser His Asp Cys Ile Leu Thr
                405                 410                 415

Ser Asp Gly Pro Leu Cys Ile Cys Pro Ala Gly Ser Val Leu Gly Lys
            420                 425                 430

Asp Gly Lys Thr Cys Thr Gly Cys Ser Phe Ser Asp Asn Gly Gly Cys
        435                 440                 445

Ser Gln Ile Cys Leu Pro Leu Ser Leu Ala Ser Trp Glu Cys Asp Cys
    450                 455                 460

Phe Pro Gly Tyr Asp Leu Gln Leu Asp Arg Lys Ser Cys Ala Ala Ser
465                 470                 475                 480

Met Gly Pro Gln Pro Phe Leu Leu Phe Ala Asn Ser Gln Asp Ile Arg
                485                 490                 495

His Met His Phe Asp Gly Thr Asp Tyr Lys Thr Leu Leu Ser Arg Gln
            500                 505                 510

Met Gly Met Val Phe Ala Leu Asp Tyr Asp Pro Val Glu Ser Lys Ile
```

```
            515                 520                 525
Tyr Phe Ala Gln Thr Ala Leu Lys Trp Ile Glu Arg Ala Asn Leu Asp
        530                 535                 540

Gly Ser Gln Arg Glu Arg Ile Thr Glu Gly Val Asp Thr Pro Glu
545                 550                 555                 560

Gly Leu Ala Val Asp Trp Ile Gly Arg Ile Tyr Trp Thr Asp Ser
                565                 570                 575

Gly Lys Ser Val Ile Glu Gly Ser Asp Leu Ser Gly Lys His His Gln
            580                 585                 590

Ile Ile Ile Lys Glu Ser Ile Ser Arg Pro Arg Gly Ile Ala Val His
            595                 600                 605

Pro Lys Ala Arg Arg Leu Phe Trp Thr Asp Thr Gly Met Ser Pro Arg
610                 615                 620

Ile Glu Ser Ser Ser Leu Gln Gly Ser Asp Arg Thr Leu Ile Ala Ser
625                 630                 635                 640

Ser Asn Leu Leu Glu Pro Ser Gly Ile Ala Ile Asp Tyr Leu Thr Asp
                645                 650                 655

Thr Leu Tyr Trp Cys Asp Thr Lys Leu Ser Val Ile Glu Met Ala Asp
                660                 665                 670

Leu Asp Gly Ser Lys Arg Arg Leu Thr Gln Asn Asp Val Gly His
            675                 680                 685

Pro Phe Ser Leu Ala Val Phe Glu Asp His Val Trp Phe Ser Asp Trp
690                 695                 700

Ala Ile Pro Ser Val Ile Arg Val Asn Lys Arg Thr Gly Gln Asn Arg
705                 710                 715                 720

Val Arg Leu Arg Gly Ser Met Leu Lys Pro Ser Ser Leu Val Val Val
                725                 730                 735

His Pro Leu Ala Lys Pro Gly Ala Asp Pro Cys Leu His Arg Asn Gly
                740                 745                 750

Gly Cys Glu His Ile Cys Gln Glu Ser Leu Gly Thr Ala Gln Cys Leu
            755                 760                 765

Cys Arg Glu Gly Phe Val Lys Ala Pro Asp Gly Lys Met Cys Leu Thr
770                 775                 780

Arg Lys Asp Asp Gln Ile Leu Ala Gly Asp Asn Ala Asp Leu Ser Lys
785                 790                 795                 800

Glu Val Ala Ser Leu Asp Asn Ser Pro Lys Ala Tyr Val Pro Asp Asp
                805                 810                 815

Asp Arg Thr Glu Ser Ser Thr Leu Val Ala Glu Ile Met Val Ser Gly
                820                 825                 830

Leu Asn Tyr Glu Asp Asp Cys Gly Pro Gly Gly Cys Gly Ser His Ala
            835                 840                 845

His Cys Ile Ser Glu Gly Glu Ala Ala Val Cys Gln Cys Leu Lys Gly
            850                 855                 860

Phe Ala Gly Asp Gly Asn Leu Cys Ser Asp Ile Asp Glu Cys Glu Leu
865                 870                 875                 880

Gly Ser Ser Asp Cys Pro Pro Thr Ser Arg Cys Ile Asn Thr Glu
                885                 890                 895

Gly Gly Tyr Val Cys Gln Cys Ser Glu Gly Tyr Glu Gly Asp Gly Ile
                900                 905                 910

Tyr Cys Leu Asp Val Asp Glu Cys Gln Gln Gly Ser His Gly Cys Ser
            915                 920                 925

Glu Asn Ala Thr Cys Thr Asn Thr Glu Gly Gly Tyr Asn Cys Thr Cys
930                 935                 940
```

```
Ala Gly Cys Pro Ser Ala Pro Gly Leu Pro Cys Pro Asp Ser Thr Ser
945                 950                 955                 960

Pro Ser Leu Leu Gly Lys Asp Gly Cys His Trp Val Arg Asn Ser Asn
            965                 970                 975

Thr Gly Cys Pro Pro Ser Tyr Asp Gly Tyr Cys Leu Asn Gly Gly Val
        980                 985                 990

Cys Met Tyr Val Glu Ser Val Asp Arg Tyr Val Cys Asn Cys Val Ile
            995                1000                1005

Gly Tyr Ile Gly Glu Arg Cys Gln His Arg Asp Leu Arg Trp Trp
        1010                1015                1020

Lys Leu Arg His Ala Asp Tyr Gly Gln Arg His Asp Ile Thr Val
    1025                1030                1035

Val Ser Val Cys Val Val Ala Leu Ala Leu Leu Leu Leu Leu Gly
    1040                1045                1050

Met Trp Gly Thr Tyr Tyr Tyr Arg Thr Arg Lys Gln Leu Ser Glu
    1055                1060                1065

Ser Ser Lys Lys Pro Ser Glu Glu Ser Ser Asn Val Ser Ser
    1070                1075                1080

Asn Gly Pro Asp Ser Ser Gly Ala Gly Val Ser Gly Pro Gln
    1085                1090                1095

Pro Trp Phe Val Val Leu Glu His Gln Gln Pro Lys Asn Gly
    1100                1105                1110

Arg Leu Pro Ala Ala Gly Thr Asn Gly Ala Val Val Glu Ala Gly
    1115                1120                1125

Leu Ser Ser Ser Leu
    1130

<210> SEQ ID NO 5
<211> LENGTH: 141
<212> TYPE: DNA
<213> ORGANISM: Rattus norvegicus
<220> FEATURE:
<221> NAME/KEY: CDS
<222> LOCATION: (1)..(141)

<400> SEQUENCE: 5 aac agt aac aca gga tgc ccg ccg tcg tac gat ggg tac tgc ctc aat      48
Asn Ser Asn Thr Gly Cys Pro Pro Ser Tyr Asp Gly Tyr Cys Leu Asn
1               5                   10                  15 ggt ggc gtg tgc atg tat gtt gaa tcc gtg gac cgc tac gtg tgc aac      96
Gly Gly Val Cys Met Tyr Val Glu Ser Val Asp Arg Tyr Val Cys Asn
            20                  25                  30 tgt gtc att ggc tat att gga gaa cga tgt cag cac cga gac tta          141
Cys Val Ile Gly Tyr Ile Gly Glu Arg Cys Gln His Arg Asp Leu
        35                  40                  45

<210> SEQ ID NO 6
<211> LENGTH: 491
<212> TYPE: PRT
<213> ORGANISM: Artificial sequence
<220> FEATURE:
<223> OTHER INFORMATION: Plasmid

<400> SEQUENCE: 6

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30
```

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
 130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
 210                 215                 220

Gly Ser Asn Ser Asn Thr Gly Cys Pro Ser Tyr Asp Gly Tyr Cys
225                 230                 235                 240

Leu Asn Gly Gly Val Cys Met Tyr Val Glu Ser Val Asp Arg Tyr Val
                245                 250                 255

Cys Asn Cys Val Ile Gly Tyr Ile Gly Glu Arg Cys Gln His Arg Asp
            260                 265                 270

Leu Gly Ile Pro Glu Ile Lys Asp Leu Ser Glu Asn Lys Leu Pro Val
        275                 280                 285

Ile Tyr Met His Val Pro Lys Ser Gly Ala Leu Asn Gln Lys Val Val
 290                 295                 300

Phe Tyr Gly Lys Gly Thr Tyr Asp Pro Asp Gly Ser Ile Ala Gly Tyr
305                 310                 315                 320

Gln Trp Asp Phe Gly Asp Gly Ser Asp Phe Ser Ser Glu Gln Asn Pro
                325                 330                 335

Ser His Val Tyr Thr Lys Lys Gly Glu Tyr Thr Val Thr Leu Arg Val
            340                 345                 350

Met Asp Ser Ser Gly Gln Met Ser Glu Lys Thr Met Lys Ile Lys Ile
        355                 360                 365

Thr Asp Pro Val Tyr Pro Ile Gly Thr Glu Lys Glu Pro Asn Asn Ser
 370                 375                 380

Lys Glu Thr Ala Ser Gly Pro Ile Val Pro Gly Ile Pro Val Ser Gly
385                 390                 395                 400

Thr Ile Glu Asn Thr Ser Asp Gln Asp Tyr Phe Tyr Phe Asp Val Ile
                405                 410                 415

Thr Pro Gly Glu Val Lys Ile Asp Ile Asn Lys Leu Gly Tyr Gly Gly
            420                 425                 430

Ala Thr Trp Val Val Tyr Asp Glu Asn Asn Asn Ala Val Ser Tyr Ala
        435                 440                 445

Thr Asp Asp Gly Gln Asn Leu Ser Gly Lys Phe Lys Ala Asp Lys Pro

```
                    450                 455                 460
Gly Arg Tyr Tyr Ile His Leu Tyr Met Phe Asn Gly Ser Tyr Met Pro
465                 470                 475                 480

Tyr Arg Ile Asn Ile Glu Gly Ser Val Gly Arg
                485                 490

<210> SEQ ID NO 7
<211> LENGTH: 1476
<212> TYPE: DNA
<213> ORGANISM: Artificial sequence
<220> FEATURE:
<223> OTHER INFORMATION: Plasmid
<220> FEATURE:
<221> NAME/KEY: CDS
<222> LOCATION: (1)..(1476)

<400> SEQUENCE: 7 atg tcc cct ata cta ggt tat tgg aaa att aag ggc ctt gtg caa ccc        48
Met Ser Pro Ile Leu Gly Tyr Trp Lys Ile Lys Gly Leu Val Gln Pro
1               5                   10                  15 act cga ctt ctt ttg gaa tat ctt gaa gaa aaa tat gaa gag cat ttg        96
Thr Arg Leu Leu Leu Glu Tyr Leu Glu Glu Lys Tyr Glu Glu His Leu
                20                  25                  30 tat gag cgc gat gaa ggt gat aaa tgg cga aac aaa aag ttt gaa ttg       144
Tyr Glu Arg Asp Glu Gly Asp Lys Trp Arg Asn Lys Lys Phe Glu Leu
            35                  40                  45 ggt ttg gag ttt ccc aat ctt cct tat tat att gat ggt gat gtt aaa       192
Gly Leu Glu Phe Pro Asn Leu Pro Tyr Tyr Ile Asp Gly Asp Val Lys
        50                  55                  60 tta aca cag tct atg gcc atc ata cgt tat ata gct gac aag cac aac       240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa       288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt       336
Gly Ala Val Leu Asp Ile Arg Tyr Gly Val Ser Arg Ile Ala Tyr Ser
                100                 105                 110 aaa gac ttt gaa act ctc aaa gtt gat ttt ctt agc aag cta cct gaa       384
Lys Asp Phe Glu Thr Leu Lys Val Asp Phe Leu Ser Lys Leu Pro Glu
            115                 120                 125 atg ctg aaa atg ttc gaa gat cgt tta tgt cat aaa aca tat tta aat       432
Met Leu Lys Met Phe Glu Asp Arg Leu Cys His Lys Thr Tyr Leu Asn
        130                 135                 140 ggt gat cat gta acc cat cct gac ttc atg ttg tat gac gct ctt gat       480
Gly Asp His Val Thr His Pro Asp Phe Met Leu Tyr Asp Ala Leu Asp
145                 150                 155                 160 gtt gtt tta tac atg gac cca atg tgc ctg gat gcg ttc cca aaa tta       528
Val Val Leu Tyr Met Asp Pro Met Cys Leu Asp Ala Phe Pro Lys Leu
                165                 170                 175 gtt tgt ttt aaa aaa cgt att gaa gct atc cca caa att gat aag tac       576
Val Cys Phe Lys Lys Arg Ile Glu Ala Ile Pro Gln Ile Asp Lys Tyr
            180                 185                 190 ttg aaa tcc agc aag tat ata gca tgg cct ttg cag ggc tgg caa gcc       624
Leu Lys Ser Ser Lys Tyr Ile Ala Trp Pro Leu Gln Gly Trp Gln Ala
        195                 200                 205 acg ttt ggt ggt ggc gac cat cct cca aaa tcg gat ctg gtt ccg cgt       672
Thr Phe Gly Gly Gly Asp His Pro Pro Lys Ser Asp Leu Val Pro Arg
    210                 215                 220 gga tcc aac agt aac aca gga tgc ccg ccg tcg tac gat ggg tac tgc       720
Gly Ser Asn Ser Asn Thr Gly Cys Pro Pro Ser Tyr Asp Gly Tyr Cys
```

```
                    225                 230                 235                 240
ctc aat ggt ggc gtg tgc atg tat gtt gaa tcc gtg gac cgc tac gtg       768
Leu Asn Gly Gly Val Cys Met Tyr Val Glu Ser Val Asp Arg Tyr Val
                245                 250                 255 tgc aac tgt gtc att ggc tat att gga gaa cga tgt cag cac cga gac       816
Cys Asn Cys Val Ile Gly Tyr Ile Gly Glu Arg Cys Gln His Arg Asp
                260                 265                 270 tta gga att ccc gaa ata aag gat ctt tca gaa aat aaa ctt cca gtt       864
Leu Gly Ile Pro Glu Ile Lys Asp Leu Ser Glu Asn Lys Leu Pro Val
                275                 280                 285 ata tat atg cat gta cct aaa tcc gga gcc tta aat caa aaa gtt gtt       912
Ile Tyr Met His Val Pro Lys Ser Gly Ala Leu Asn Gln Lys Val Val
                290                 295                 300 ttc tat gga aaa gga aca tat gac cca gat gga tct atc gca gga tat       960
Phe Tyr Gly Lys Gly Thr Tyr Asp Pro Asp Gly Ser Ile Ala Gly Tyr
305                 310                 315                 320 caa tgg gac ttt ggt gat gga agt gat ttt agc agt gaa caa aac cca      1008
Gln Trp Asp Phe Gly Asp Gly Ser Asp Phe Ser Ser Glu Gln Asn Pro
                325                 330                 335 agc cat gta tat act aaa aaa ggt gaa tat act gta aca tta aga gta      1056
Ser His Val Tyr Thr Lys Lys Gly Glu Tyr Thr Val Thr Leu Arg Val
                340                 345                 350 atg gat agt agt gga caa atg agt gaa aaa act atg aag att aag att      1104
Met Asp Ser Ser Gly Gln Met Ser Glu Lys Thr Met Lys Ile Lys Ile
                355                 360                 365 aca gat ccg gta tat cca ata ggc act gaa aaa gaa cca aat aac agt      1152
Thr Asp Pro Val Tyr Pro Ile Gly Thr Glu Lys Glu Pro Asn Asn Ser
                370                 375                 380 aaa gaa act gca agt ggt cca ata gta cca ggt ata cct gtt agt gga      1200
Lys Glu Thr Ala Ser Gly Pro Ile Val Pro Gly Ile Pro Val Ser Gly
385                 390                 395                 400 acc ata gaa aat aca agt gat caa gat tat ttc tat ttt gat gtt ata      1248
Thr Ile Glu Asn Thr Ser Asp Gln Asp Tyr Phe Tyr Phe Asp Val Ile
                405                 410                 415 aca cca gga gaa gta aaa ata gat ata aat aaa tta ggg tac gga gga      1296
Thr Pro Gly Glu Val Lys Ile Asp Ile Asn Lys Leu Gly Tyr Gly Gly
                420                 425                 430 gct act tgg gta gta tat gat gaa aat aat aat gca gta tct tat gcc      1344
Ala Thr Trp Val Val Tyr Asp Glu Asn Asn Asn Ala Val Ser Tyr Ala
                435                 440                 445 act gat gat ggg caa aat tta agt gga aag ttt aag gca gat aaa cca      1392
Thr Asp Asp Gly Gln Asn Leu Ser Gly Lys Phe Lys Ala Asp Lys Pro
450                 455                 460 ggt aga tat tac atc cat ctt tac atg ttt aat ggt agt tat atg cca      1440
Gly Arg Tyr Tyr Ile His Leu Tyr Met Phe Asn Gly Ser Tyr Met Pro
465                 470                 475                 480 tat aga att aat ata gaa ggt tca gta gga aga taa                      1476
Tyr Arg Ile Asn Ile Glu Gly Ser Val Gly Arg
                485                 490

<210> SEQ ID NO 8
<211> LENGTH: 599
<212> TYPE: PRT
<213> ORGANISM: Artificial sequence
<220> FEATURE:
<223> OTHER INFORMATION: GST-bFGF-CBD

<400> SEQUENCE: 8

Met Ser Pro Ile Leu Gly Tyr Trp Lys Ile Lys Gly Leu Val Gln Pro
1               5                   10                  15
```

-continued

Thr Arg Leu Leu Leu Glu Tyr Leu Glu Lys Tyr Glu Glu His Leu
        20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Leu Val Pro Arg
 210                 215                 220

Gly Ser Met Ala Ala Gly Ser Ile Thr Thr Leu Pro Ala Leu Pro Glu
225                 230                 235                 240

Asp Gly Gly Ser Gly Ala Phe Pro Pro Gly His Phe Lys Asp Pro Lys
                245                 250                 255

Arg Leu Tyr Cys Lys Asn Gly Gly Phe Phe Leu Arg Ile His Pro Asp
            260                 265                 270

Gly Arg Val Asp Gly Val Arg Glu Lys Ser Asp Pro His Ile Lys Leu
            275                 280                 285

Gln Leu Gln Ala Glu Glu Arg Gly Val Val Ser Ile Lys Gly Val Cys
 290                 295                 300

Ala Asn Arg Tyr Leu Ala Met Lys Glu Asp Gly Arg Leu Leu Ala Ser
305                 310                 315                 320

Lys Cys Val Thr Asp Glu Cys Phe Phe Phe Glu Arg Leu Glu Ser Asn
                325                 330                 335

Asn Tyr Asn Thr Tyr Arg Ser Arg Lys Tyr Thr Ser Trp Tyr Val Ala
            340                 345                 350

Leu Lys Arg Thr Gly Gln Tyr Lys Leu Gly Ser Lys Thr Gly Pro Gly
            355                 360                 365

Gln Lys Ala Ile Leu Phe Leu Pro Met Ser Ala Lys Ser Gly Ile Pro
 370                 375                 380

Glu Ile Lys Asp Leu Ser Glu Asn Lys Leu Pro Val Ile Tyr Met His
385                 390                 395                 400

Val Pro Lys Ser Gly Ala Leu Asn Gln Lys Val Val Phe Tyr Gly Lys
                405                 410                 415

Gly Thr Tyr Asp Pro Asp Gly Ser Ile Ala Gly Tyr Gln Trp Asp Phe
            420                 425                 430

Gly Asp Gly Ser Asp Phe Ser Ser Glu Gln Asn Pro Ser His Val Tyr

```
                  435                 440                 445
Thr Lys Lys Gly Glu Tyr Thr Val Thr Leu Arg Val Met Asp Ser Ser
    450                 455                 460

Gly Gln Met Ser Glu Lys Thr Met Lys Ile Lys Ile Thr Asp Pro Val
465                 470                 475                 480

Tyr Pro Ile Gly Thr Glu Lys Glu Pro Asn Asn Ser Lys Glu Thr Ala
                485                 490                 495

Ser Gly Pro Ile Val Pro Gly Ile Pro Val Ser Gly Thr Ile Glu Asn
            500                 505                 510

Thr Ser Asp Gln Asp Tyr Phe Tyr Phe Asp Val Ile Thr Pro Gly Glu
        515                 520                 525

Val Lys Ile Asp Ile Asn Lys Leu Gly Tyr Gly Gly Ala Thr Trp Val
    530                 535                 540

Val Tyr Asp Glu Asn Asn Asn Ala Val Ser Tyr Ala Thr Asp Asp Gly
545                 550                 555                 560

Gln Asn Leu Ser Gly Lys Phe Lys Ala Asp Lys Pro Gly Arg Tyr Tyr
                565                 570                 575

Ile His Leu Tyr Met Phe Asn Gly Ser Tyr Met Pro Tyr Arg Ile Asn
            580                 585                 590

Ile Glu Gly Ser Val Gly Arg
        595
```

<210> SEQ ID NO 9
<211> LENGTH: 1800
<212> TYPE: DNA
<213> ORGANISM: Artificial sequence
<220> FEATURE:
<223> OTHER INFORMATION: Plasmid
<220> FEATURE:
<221> NAME/KEY: CDS
<222> LOCATION: (1)..(1800)

<400> SEQUENCE: 9

```
atg tcc cct ata cta ggt tat tgg aaa att aag ggc ctt gtg caa ccc      48
Met Ser Pro Ile Leu Gly Tyr Trp Lys Ile Lys Gly Leu Val Gln Pro
1               5                  10                  15 act cga ctt ctt ttg gaa tat ctt gaa gaa aaa tat gaa gag cat ttg      96
Thr Arg Leu Leu Leu Glu Tyr Leu Glu Glu Lys Tyr Glu Glu His Leu
            20                  25                  30 tat gag cgc gat gaa ggt gat aaa tgg cga aac aaa aag ttt gaa ttg     144
Tyr Glu Arg Asp Glu Gly Asp Lys Trp Arg Asn Lys Lys Phe Glu Leu
        35                  40                  45 ggt ttg gag ttt ccc aat ctt cct tat tat att gat ggt gat gtt aaa     192
Gly Leu Glu Phe Pro Asn Leu Pro Tyr Tyr Ile Asp Gly Asp Val Lys
    50                  55                  60 tta aca cag tct atg gcc atc ata cgt tat ata gct gac aag cac aac     240
Leu Thr Gln Ser Met Ala Ile Ile Arg Tyr Ile Ala Asp Lys His Asn
65                  70                  75                  80 atg ttg ggt ggt tgt cca aaa gag cgt gca gag att tca atg ctt gaa     288
Met Leu Gly Gly Cys Pro Lys Glu Arg Ala Glu Ile Ser Met Leu Glu
                85                  90                  95 gga gcg gtt ttg gat att aga tac ggt gtt tcg aga att gca tat agt     336
Gly Ala Val Leu Asp Ile Arg Tyr Gly Val Ser Arg Ile Ala Tyr Ser
            100                 105                 110 aaa gac ttt gaa act ctc aaa gtt gat ttt ctt agc aag cta cct gaa     384
Lys Asp Phe Glu Thr Leu Lys Val Asp Phe Leu Ser Lys Leu Pro Glu
        115                 120                 125 atg ctg aaa atg ttc gaa gat cgt tta tgt cat aaa aca tat tta aat     432
Met Leu Lys Met Phe Glu Asp Arg Leu Cys His Lys Thr Tyr Leu Asn
```

-continued

| | | | |
|---|---|---|---|
| | 130 | 135 | 140 |
| ggt gat cat gta acc cat cct gac ttc atg ttg tat gac gct ctt gat<br>Gly Asp His Val Thr His Pro Asp Phe Met Leu Tyr Asp Ala Leu Asp<br>145                              150                             155                             160 | | 480 |
| gtt gtt tta tac atg gac cca atg tgc ctg gat gcg ttc cca aaa tta<br>Val Val Leu Tyr Met Asp Pro Met Cys Leu Asp Ala Phe Pro Lys Leu<br>                              165                             170                             175 | | 528 |
| gtt tgt ttt aaa aaa cgt att gaa gct atc cca caa att gat aag tac<br>Val Cys Phe Lys Lys Arg Ile Glu Ala Ile Pro Gln Ile Asp Lys Tyr<br>                 180                           185                             190 | | 576 |
| ttg aaa tcc agc aag tat ata gca tgg cct ttg cag ggc tgg caa gcc<br>Leu Lys Ser Ser Lys Tyr Ile Ala Trp Pro Leu Gln Gly Trp Gln Ala<br>                     195                           200                          205 | | 624 |
| acg ttt ggt ggt ggc gac cat cct cca aaa tcg gat ctg gtt ccg cgt<br>Thr Phe Gly Gly Gly Asp His Pro Pro Lys Ser Asp Leu Val Pro Arg<br>210                              215                             220 | | 672 |
| gga tct atg gca gcc ggg agc atc acc acg ctg ccc gcc ttg ccc gag<br>Gly Ser Met Ala Ala Gly Ser Ile Thr Thr Leu Pro Ala Leu Pro Glu<br>225                              230                             235                          240 | | 720 |
| gat ggc ggc agc ggc gcc ttc ccg ccc ggc cac ttc aag gac ccc aag<br>Asp Gly Gly Ser Gly Ala Phe Pro Pro Gly His Phe Lys Asp Pro Lys<br>                              245                             250                          255 | | 768 |
| cgg ctg tac tgc aaa aac ggg ggc ttc ttc ctg cgc atc cac ccc gac<br>Arg Leu Tyr Cys Lys Asn Gly Gly Phe Phe Leu Arg Ile His Pro Asp<br>                 260                           265                             270 | | 816 |
| ggc cga gtt gac ggg gtc cgg gag aag agc gac cct cac atc aag cta<br>Gly Arg Val Asp Gly Val Arg Glu Lys Ser Asp Pro His Ile Lys Leu<br>            275                             280                          285 | | 864 |
| caa ctt caa gca gaa gag aga gga gtt gtg tct atc aaa gga gtg tgt<br>Gln Leu Gln Ala Glu Glu Arg Gly Val Val Ser Ile Lys Gly Val Cys<br>               290                           295                          300 | | 912 |
| gct aac cgt tac ctg gct atg aag gaa gat gga aga tta ctg gct tct<br>Ala Asn Arg Tyr Leu Ala Met Lys Glu Asp Gly Arg Leu Leu Ala Ser<br>305                              310                             315                          320 | | 960 |
| aaa tgt gtt acg gat gag tgt ttc ttt ttt gaa cga ttg gaa tct aat<br>Lys Cys Val Thr Asp Glu Cys Phe Phe Phe Glu Arg Leu Glu Ser Asn<br>                             325                             330                          335 | | 1008 |
| aac tac aat act tac cgg tca agg aaa tac acc agt tgg tat gtg gca<br>Asn Tyr Asn Thr Tyr Arg Ser Arg Lys Tyr Thr Ser Trp Tyr Val Ala<br>                 340                           345                             350 | | 1056 |
| ctg aaa cga act ggg cag tat aaa ctt gga tcc aaa aca gga cct ggg<br>Leu Lys Arg Thr Gly Gln Tyr Lys Leu Gly Ser Lys Thr Gly Pro Gly<br>            355                             360                          365 | | 1104 |
| cag aaa gct ata ctt ttt ctt cca atg tct gct aag agc gga att ccc<br>Gln Lys Ala Ile Leu Phe Leu Pro Met Ser Ala Lys Ser Gly Ile Pro<br>          370                             375                             380 | | 1152 |
| gaa ata aag gat ctt tca gaa aat aaa ctt cca gtt ata tat atg cat<br>Glu Ile Lys Asp Leu Ser Glu Asn Lys Leu Pro Val Ile Tyr Met His<br>385                              390                             395                          400 | | 1200 |
| gta cct aaa tcc gga gcc tta aat caa aaa gtt gtt ttc tat gga aaa<br>Val Pro Lys Ser Gly Ala Leu Asn Gln Lys Val Val Phe Tyr Gly Lys<br>                              405                             410                          415 | | 1248 |
| gga aca tat gac cca gat gga tct atc gca gga tat caa tgg gac ttt<br>Gly Thr Tyr Asp Pro Asp Gly Ser Ile Ala Gly Tyr Gln Trp Asp Phe<br>                 420                           425                             430 | | 1296 |
| ggt gat gga agt gat ttt agc agt gaa caa aac cca agc cat gta tat<br>Gly Asp Gly Ser Asp Phe Ser Ser Glu Gln Asn Pro Ser His Val Tyr<br>            435                             440                          445 | | 1344 |
| act aaa aaa ggt gaa tat act gta aca tta aga gta atg gat agt agt | | 1392 |

```
Thr Lys Lys Gly Glu Tyr Thr Val Thr Leu Arg Val Met Asp Ser Ser
    450                 455                 460 gga caa atg agt gaa aaa act atg aag att aag att aca gat ccg gta      1440
Gly Gln Met Ser Glu Lys Thr Met Lys Ile Lys Ile Thr Asp Pro Val
465                 470                 475                 480 tat cca ata ggc act gaa aaa gaa cca aat aac agt aaa gaa act gca      1488
Tyr Pro Ile Gly Thr Glu Lys Glu Pro Asn Asn Ser Lys Glu Thr Ala
                485                 490                 495 agt ggt cca ata gta cca ggt ata cct gtt agt gga acc ata gaa aat      1536
Ser Gly Pro Ile Val Pro Gly Ile Pro Val Ser Gly Thr Ile Glu Asn
            500                 505                 510 aca agt gat caa gat tat ttc tat ttt gat gtt ata aca cca gga gaa      1584
Thr Ser Asp Gln Asp Tyr Phe Tyr Phe Asp Val Ile Thr Pro Gly Glu
        515                 520                 525 gta aaa ata gat ata aat aaa tta ggg tac gga gga gct act tgg gta      1632
Val Lys Ile Asp Ile Asn Lys Leu Gly Tyr Gly Gly Ala Thr Trp Val
    530                 535                 540 gta tat gat gaa aat aat aat gca gta tct tat gcc act gat gat ggg      1680
Val Tyr Asp Glu Asn Asn Asn Ala Val Ser Tyr Ala Thr Asp Asp Gly
545                 550                 555                 560 caa aat tta agt gga aag ttt aag gca gat aaa cca ggt aga tat tac      1728
Gln Asn Leu Ser Gly Lys Phe Lys Ala Asp Lys Pro Gly Arg Tyr Tyr
                565                 570                 575 atc cat ctt tac atg ttt aat ggt agt tat atg cca tat aga att aat      1776
Ile His Leu Tyr Met Phe Asn Gly Ser Tyr Met Pro Tyr Arg Ile Asn
            580                 585                 590 ata gaa ggt tca gta gga aga taa                                      1800
Ile Glu Gly Ser Val Gly Arg
        595

<210> SEQ ID NO 10
<211> LENGTH: 375
<212> TYPE: PRT
<213> ORGANISM: Artificial sequence
<220> FEATURE:
<223> OTHER INFORMATION: bFGF-CBD

<400> SEQUENCE: 10

Gly Ser Met Ala Ala Gly Ser Ile Thr Thr Leu Pro Ala Leu Pro Glu
1               5                   10                  15

Asp Gly Gly Ser Gly Ala Phe Pro Pro Gly His Phe Lys Asp Pro Lys
                20                  25                  30

Arg Leu Tyr Cys Lys Asn Gly Gly Phe Phe Leu Arg Ile His Pro Asp
            35                  40                  45

Gly Arg Val Asp Gly Val Arg Glu Lys Ser Asp Pro His Ile Lys Leu
        50                  55                  60

Gln Leu Gln Ala Glu Glu Arg Gly Val Val Ser Ile Lys Gly Val Cys
65                  70                  75                  80

Ala Asn Arg Tyr Leu Ala Met Lys Glu Asp Gly Arg Leu Leu Ala Ser
                85                  90                  95

Lys Cys Val Thr Asp Glu Cys Phe Phe Phe Glu Arg Leu Glu Ser Asn
            100                 105                 110

Asn Tyr Asn Thr Tyr Arg Ser Arg Lys Tyr Thr Ser Trp Tyr Val Ala
        115                 120                 125

Leu Lys Arg Thr Gly Gln Tyr Lys Leu Gly Ser Lys Thr Gly Pro Gly
    130                 135                 140

Gln Lys Ala Ile Leu Phe Leu Pro Met Ser Ala Lys Ser Gly Ile Pro
145                 150                 155                 160
```

```
Glu Ile Lys Asp Leu Ser Glu Asn Lys Leu Pro Val Ile Tyr Met His
            165                 170                 175

Val Pro Lys Ser Gly Ala Leu Asn Gln Lys Val Val Phe Tyr Gly Lys
        180                 185                 190

Gly Thr Tyr Asp Pro Asp Gly Ser Ile Ala Gly Tyr Gln Trp Asp Phe
        195                 200                 205

Gly Asp Gly Ser Asp Phe Ser Ser Glu Gln Asn Pro Ser His Val Tyr
    210                 215                 220

Thr Lys Lys Gly Glu Tyr Thr Val Thr Leu Arg Val Met Asp Ser Ser
225                 230                 235                 240

Gly Gln Met Ser Glu Lys Thr Met Lys Ile Lys Ile Thr Asp Pro Val
            245                 250                 255

Tyr Pro Ile Gly Thr Glu Lys Glu Pro Asn Asn Ser Lys Glu Thr Ala
        260                 265                 270

Ser Gly Pro Ile Val Pro Gly Ile Pro Val Ser Gly Thr Ile Glu Asn
    275                 280                 285

Thr Ser Asp Gln Asp Tyr Phe Tyr Phe Asp Val Ile Thr Pro Gly Glu
290                 295                 300

Val Lys Ile Asp Ile Asn Lys Leu Gly Tyr Gly Gly Ala Thr Trp Val
305                 310                 315                 320

Val Tyr Asp Glu Asn Asn Asn Ala Val Ser Tyr Ala Thr Asp Asp Gly
            325                 330                 335

Gln Asn Leu Ser Gly Lys Phe Lys Ala Asp Lys Pro Gly Arg Tyr Tyr
        340                 345                 350

Ile His Leu Tyr Met Phe Asn Gly Ser Tyr Met Pro Tyr Arg Ile Asn
    355                 360                 365

Ile Glu Gly Ser Val Gly Arg
370                 375

<210> SEQ ID NO 11
<211> LENGTH: 1128
<212> TYPE: DNA
<213> ORGANISM: Artificial sequence
<220> FEATURE:
<223> OTHER INFORMATION: bFGF-PKD-CBD(II)
<220> FEATURE:
<221> NAME/KEY: CDS
<222> LOCATION: (1)..(1128)

<400> SEQUENCE: 11 gga tct atg gca gcc ggg agc atc acc acg ctg ccc gcc ttg ccc gag      48
Gly Ser Met Ala Ala Gly Ser Ile Thr Thr Leu Pro Ala Leu Pro Glu
1               5                   10                  15 gat ggc ggc agc ggc gcc ttc ccg ccc ggc cac ttc aag gac ccc aag      96
Asp Gly Gly Ser Gly Ala Phe Pro Pro Gly His Phe Lys Asp Pro Lys
            20                  25                  30 cgg ctg tac tgc aaa aac ggg ggc ttc ttc ctg cgc atc cac ccc gac     144
Arg Leu Tyr Cys Lys Asn Gly Gly Phe Phe Leu Arg Ile His Pro Asp
        35                  40                  45 ggc cga gtt gac ggg gtc cgg gag aag agc gac cct cac atc aag cta     192
Gly Arg Val Asp Gly Val Arg Glu Lys Ser Asp Pro His Ile Lys Leu
    50                  55                  60 caa ctt caa gca gaa gag aga gga gtt gtg tct atc aaa gga gtg tgt     240
Gln Leu Gln Ala Glu Glu Arg Gly Val Val Ser Ile Lys Gly Val Cys
65                  70                  75                  80 gct aac cgt tac ctg gct atg aag gaa gat gga aga tta ctg gct tct     288
Ala Asn Arg Tyr Leu Ala Met Lys Glu Asp Gly Arg Leu Leu Ala Ser
                85                  90                  95
```

| | | |
|---|---|---|
| aaa tgt gtt acg gat gag tgt ttc ttt ttt gaa cga ttg gaa tct aat<br>Lys Cys Val Thr Asp Glu Cys Phe Phe Phe Glu Arg Leu Glu Ser Asn<br>100 105 110 | | 336 |
| aac tac aat act tac cgg tca agg aaa tac acc agt tgg tat gtg gca<br>Asn Tyr Asn Thr Tyr Arg Ser Arg Lys Tyr Thr Ser Trp Tyr Val Ala<br>115 120 125 | | 384 |
| ctg aaa cga act ggg cag tat aaa ctt gga tcc aaa aca gga cct ggg<br>Leu Lys Arg Thr Gly Gln Tyr Lys Leu Gly Ser Lys Thr Gly Pro Gly<br>130 135 140 | | 432 |
| cag aaa gct ata ctt ttt ctt cca atg tct gct aag agc gga att ccc<br>Gln Lys Ala Ile Leu Phe Leu Pro Met Ser Ala Lys Ser Gly Ile Pro<br>145 150 155 160 | | 480 |
| gaa ata aag gat ctt tca gaa aat aaa ctt cca gtt ata tat atg cat<br>Glu Ile Lys Asp Leu Ser Glu Asn Lys Leu Pro Val Ile Tyr Met His<br>165 170 175 | | 528 |
| gta cct aaa tcc gga gcc tta aat caa aaa gtt gtt ttc tat gga aaa<br>Val Pro Lys Ser Gly Ala Leu Asn Gln Lys Val Val Phe Tyr Gly Lys<br>180 185 190 | | 576 |
| gga aca tat gac cca gat gga tct atc gca gga tat caa tgg gac ttt<br>Gly Thr Tyr Asp Pro Asp Gly Ser Ile Ala Gly Tyr Gln Trp Asp Phe<br>195 200 205 | | 624 |
| ggt gat gga agt gat ttt agc agt gaa caa aac cca agc cat gta tat<br>Gly Asp Gly Ser Asp Phe Ser Ser Glu Gln Asn Pro Ser His Val Tyr<br>210 215 220 | | 672 |
| act aaa aaa ggt gaa tat act gta aca tta aga gta atg gat agt agt<br>Thr Lys Lys Gly Glu Tyr Thr Val Thr Leu Arg Val Met Asp Ser Ser<br>225 230 235 240 | | 720 |
| gga caa atg agt gaa aaa act atg aag att aag att aca gat ccg gta<br>Gly Gln Met Ser Glu Lys Thr Met Lys Ile Lys Ile Thr Asp Pro Val<br>245 250 255 | | 768 |
| tat cca ata ggc act gaa aaa gaa cca aat aac agt aaa gaa act gca<br>Tyr Pro Ile Gly Thr Glu Lys Glu Pro Asn Asn Ser Lys Glu Thr Ala<br>260 265 270 | | 816 |
| agt ggt cca ata gta cca ggt ata cct gtt agt gga acc ata gaa aat<br>Ser Gly Pro Ile Val Pro Gly Ile Pro Val Ser Gly Thr Ile Glu Asn<br>275 280 285 | | 864 |
| aca agt gat caa gat tat ttc tat ttt gat gtt ata aca cca gga gaa<br>Thr Ser Asp Gln Asp Tyr Phe Tyr Phe Asp Val Ile Thr Pro Gly Glu<br>290 295 300 | | 912 |
| gta aaa ata gat ata aat aaa tta ggg tac gga gga gct act tgg gta<br>Val Lys Ile Asp Ile Asn Lys Leu Gly Tyr Gly Gly Ala Thr Trp Val<br>305 310 315 320 | | 960 |
| gta tat gat gaa aat aat aat gca gta tct tat gcc act gat gat ggg<br>Val Tyr Asp Glu Asn Asn Asn Ala Val Ser Tyr Ala Thr Asp Asp Gly<br>325 330 335 | | 1008 |
| caa aat tta agt gga aag ttt aag gca gat aaa cca ggt aga tat tac<br>Gln Asn Leu Ser Gly Lys Phe Lys Ala Asp Lys Pro Gly Arg Tyr Tyr<br>340 345 350 | | 1056 |
| atc cat ctt tac atg ttt aat ggt agt tat atg cca tat aga att aat<br>Ile His Leu Tyr Met Phe Asn Gly Ser Tyr Met Pro Tyr Arg Ile Asn<br>355 360 365 | | 1104 |
| ata gaa ggt tca gta gga aga taa<br>Ile Glu Gly Ser Val Gly Arg<br>370 375 | | 1128 |

<210> SEQ ID NO 12
<211> LENGTH: 5914
<212> TYPE: DNA
<213> ORGANISM: Clostridium histolyticum class I
<220> FEATURE:
<221> NAME/KEY: CDS

<222> LOCATION: (1002)..(4355)

<400> SEQUENCE: 12

```
aagcttttat aattctcact atactctcta gatggtataa taagagccca aaatacgaag      60
aatataataa aatataattt aaaaaggatg atttcaatgc gaaaaagagt ttttttgaat     120 atattttta ttttatgttc ctcaattttt tttatgtcct gcacaggaaa atttcaggtt     180
atagatcggg gtgatggggg agatgaaatt tatttaaaca acaagatgg tgtgagtttt      240 gagattccta aagtgtggga taaaaattat aagattatca cttctagaga taaaagatat     300
ggcaaaaagt taacttttaa aaaaaggat aagaaatgca acgttatact tttagaaata     360
tggattttga atgaggaata ttggagtgaa tttaaagatg ttaggaagtt taaacttata     420
ggtaaaagcg aaaaaggcgt agtagtttat tcaagaggta aattagatag catattagaa     480
aataatggat tggacattat gcatcataaa gaagagaaaa agaaagatat agaaaaaatg     540
tacattaaag atgaagaaat tagcgataga atcaaaataa ttagaaatta ataaaaaaat     600
gaaaatagaa aaattcattt tactaaaaat ttatgtttac tttctataac aatctttgta     660
aactgtaaat actaatgtag tattttttag aaaataataa tctgttaaaa agtatattta     720
ggaactaaaa atgaataaat ttataaaaac tatttacaat atctaaaata atgtatataa     780
tttttattaa atagattatt ttggtattaa gggggtgatt gaaagaataa acagaaaatt     840
gatataattc aataaataaa atctaaagag aaatatctaa gtaatacaca aatctaatat     900
taaaaccatt ttaatattaa gaatattttg ttaataggta aaggttaaaa ggcattctat     960
tattaaggtt aaaaggtatt aattattaag ggggattatc t atg aaa aaa aat att    1016
                                              Met Lys Lys Asn Ile
                                               1               5 tta aag att ctt atg gat agt tat tct aaa gaa tct aaa att caa act    1064
Leu Lys Ile Leu Met Asp Ser Tyr Ser Lys Glu Ser Lys Ile Gln Thr
             10                  15                  20 gta cgt agg gtt acg agt gta tca ctt tta gcg gta tat ctt act atg    1112
Val Arg Arg Val Thr Ser Val Ser Leu Leu Ala Val Tyr Leu Thr Met
         25                  30                  35 aat act tca agt tta gtt tta gca aaa cca ata gaa aat act aat gat    1160
Asn Thr Ser Ser Leu Val Leu Ala Lys Pro Ile Glu Asn Thr Asn Asp
     40                  45                  50 act agt ata aaa aat gtg gag aaa tta aga aat gct cca aat gaa gag    1208
Thr Ser Ile Lys Asn Val Glu Lys Leu Arg Asn Ala Pro Asn Glu Glu
 55                  60                  65 aat agt aaa aag gta gaa gat agt aaa aat gat aag gta gaa cat gtg    1256
Asn Ser Lys Lys Val Glu Asp Ser Lys Asn Asp Lys Val Glu His Val
 70                  75                  80                  85 aaa aat ata gaa gag gca aag gtt gag caa gtt gca ccc gaa gta aaa    1304
Lys Asn Ile Glu Glu Ala Lys Val Glu Gln Val Ala Pro Glu Val Lys
                 90                  95                 100 tct aaa tca act tta aga agt gct tct ata gcg aat act aat tct gag    1352
Ser Lys Ser Thr Leu Arg Ser Ala Ser Ile Ala Asn Thr Asn Ser Glu
             105                 110                 115 aaa tat gat ttt gag tat tta aat ggt ttg agc tat act gaa ctt aca    1400
Lys Tyr Asp Phe Glu Tyr Leu Asn Gly Leu Ser Tyr Thr Glu Leu Thr
         120                 125                 130 aat tta att aaa aat ata aag tgg aat caa att aat ggt tta ttt aat    1448
Asn Leu Ile Lys Asn Ile Lys Trp Asn Gln Ile Asn Gly Leu Phe Asn
 135                 140                 145 tat agt aca ggt tct caa aag ttc ttt gga gat aaa aat cgt gta caa    1496
Tyr Ser Thr Gly Ser Gln Lys Phe Phe Gly Asp Lys Asn Arg Val Gln
150                 155                 160                 165
```

-continued

| | |
|---|---|
| gct ata att aat gct tta caa gaa agt gga aga act tac act gca aat<br>Ala Ile Ile Asn Ala Leu Gln Glu Ser Gly Arg Thr Tyr Thr Ala Asn<br>170                        175                       180 | 1544 |
| gat atg aag ggt ata gaa act ttc act gag gtt tta aga gct ggt ttt<br>Asp Met Lys Gly Ile Glu Thr Phe Thr Glu Val Leu Arg Ala Gly Phe<br>          185                      190                     195 | 1592 |
| tat tta ggg tac tat aat gat ggt tta tct tat tta aat gat aga aac<br>Tyr Leu Gly Tyr Tyr Asn Asp Gly Leu Ser Tyr Leu Asn Asp Arg Asn<br>              200                      205                     210 | 1640 |
| ttc caa gat aaa tgt ata cct gca atg att gca att caa aaa aat cct<br>Phe Gln Asp Lys Cys Ile Pro Ala Met Ile Ala Ile Gln Lys Asn Pro<br>215                        220                       225 | 1688 |
| aac ttt aag cta gga act gca gtt caa gat gaa gtt ata act tct tta<br>Asn Phe Lys Leu Gly Thr Ala Val Gln Asp Glu Val Ile Thr Ser Leu<br>230                      235                   240                   245 | 1736 |
| gga aaa cta ata gga aat gct tct gct aat gct gaa gta gtt aat aat<br>Gly Lys Leu Ile Gly Asn Ala Ser Ala Asn Ala Glu Val Val Asn Asn<br>              250                      255                     260 | 1784 |
| tgt gta cca gtt cta aaa caa ttt aga gaa aac tta aat caa tat gct<br>Cys Val Pro Val Leu Lys Gln Phe Arg Glu Asn Leu Asn Gln Tyr Ala<br>                265                      270                     275 | 1832 |
| cct gat tac gtt aaa gga aca gct gta aat gaa tta att aaa ggt att<br>Pro Asp Tyr Val Lys Gly Thr Ala Val Asn Glu Leu Ile Lys Gly Ile<br>280                        285                       290 | 1880 |
| gaa ttc gat ttt tct ggt gct gca tat gaa aaa gat gtt aag aca atg<br>Glu Phe Asp Phe Ser Gly Ala Ala Tyr Glu Lys Asp Val Lys Thr Met<br>295                        300                       305 | 1928 |
| cct tgg tat gga aaa att gat cca ttt ata aat gaa ctt aag gcc tta<br>Pro Trp Tyr Gly Lys Ile Asp Pro Phe Ile Asn Glu Leu Lys Ala Leu<br>310                        315                       320                   325 | 1976 |
| ggt cta tat gga aat ata aca agt gca act gag tgg gca tct gat gtt<br>Gly Leu Tyr Gly Asn Ile Thr Ser Ala Thr Glu Trp Ala Ser Asp Val<br>              330                      335                     340 | 2024 |
| gga ata tac tat tta agt aaa ttc ggt ctt tac tca act aac cga aat<br>Gly Ile Tyr Tyr Leu Ser Lys Phe Gly Leu Tyr Ser Thr Asn Arg Asn<br>          345                      350                     355 | 2072 |
| gac ata gta cag tca ctt gaa aag gct gta gat atg tat aag tat ggt<br>Asp Ile Val Gln Ser Leu Glu Lys Ala Val Asp Met Tyr Lys Tyr Gly<br>360                      365                      370 | 2120 |
| aaa ata gcc ttt gta gca atg gag aga ata act tgg gat tat gat ggg<br>Lys Ile Ala Phe Val Ala Met Glu Arg Ile Thr Trp Asp Tyr Asp Gly<br>375                        380                      385 | 2168 |
| att ggt tct aat ggt aaa aag gtg gat cac gat aag ttc tta gat gat<br>Ile Gly Ser Asn Gly Lys Lys Val Asp His Asp Lys Phe Leu Asp Asp<br>390                       395                   400                   405 | 2216 |
| gct gaa aaa cat tat ctg cca aag aca tat act ttt gat aat gga acc<br>Ala Glu Lys His Tyr Leu Pro Lys Thr Tyr Thr Phe Asp Asn Gly Thr<br>              410                      415                     420 | 2264 |
| ttt att ata aga gca ggg gat aag gta tcc gaa gaa aaa ata aaa agg<br>Phe Ile Ile Arg Ala Gly Asp Lys Val Ser Glu Glu Lys Ile Lys Arg<br>          425                      430                     435 | 2312 |
| cta tat tgg gca tca aga gaa gtg aag tct caa ttc cat aga gta gtt<br>Leu Tyr Trp Ala Ser Arg Glu Val Lys Ser Gln Phe His Arg Val Val<br>440                        445                       450 | 2360 |
| ggc aat gat aaa gct tta gag gtg gga aat gcc gat gat gtt tta act<br>Gly Asn Asp Lys Ala Leu Glu Val Gly Asn Ala Asp Asp Val Leu Thr<br>455                        460                       465 | 2408 |
| atg aaa ata ttt aat agc cca gaa gaa tat aaa ttt aat acc aat ata<br>Met Lys Ile Phe Asn Ser Pro Glu Glu Tyr Lys Phe Asn Thr Asn Ile | 2456 |

```
                 470               475               480               485
aat ggt gta agc act gat aat ggt ggt cta tat ata gaa cca aga ggg        2504
Asn Gly Val Ser Thr Asp Asn Gly Gly Leu Tyr Ile Glu Pro Arg Gly
                    490               495               500 act ttc tac act tat gag aga aca cct caa caa agt ata ttt agt ctt        2552
Thr Phe Tyr Thr Tyr Glu Arg Thr Pro Gln Gln Ser Ile Phe Ser Leu
                505               510               515 gaa gaa ttg ttt aga cat gaa tat act cac tat tta caa gcg aga tat        2600
Glu Glu Leu Phe Arg His Glu Tyr Thr His Tyr Leu Gln Ala Arg Tyr
            520               525               530 ctt gta gat ggt tta tgg ggg caa ggt cca ttt tat gaa aaa aat aga        2648
Leu Val Asp Gly Leu Trp Gly Gln Gly Pro Phe Tyr Glu Lys Asn Arg
        535               540               545 tta act tgg ttt gat gaa ggt aca gct gaa ttc ttt gca gga tct acc        2696
Leu Thr Trp Phe Asp Glu Gly Thr Ala Glu Phe Phe Ala Gly Ser Thr
550               555               560               565 cgt aca tct ggt gtt tta cca aga aaa tca ata tta gga tat ttg gct        2744
Arg Thr Ser Gly Val Leu Pro Arg Lys Ser Ile Leu Gly Tyr Leu Ala
                570               575               580 aag gat aaa gta gat cat aga tac tca tta aag aag act ctt aat tca        2792
Lys Asp Lys Val Asp His Arg Tyr Ser Leu Lys Lys Thr Leu Asn Ser
                585               590               595 ggg tat gat gac agt gat tgg atg ttc tat aat tat gga ttt gca gtt        2840
Gly Tyr Asp Asp Ser Asp Trp Met Phe Tyr Asn Tyr Gly Phe Ala Val
            600               605               610 gca cat tac cta tat gaa aaa gat atg cct aca ttt att aag atg aat        2888
Ala His Tyr Leu Tyr Glu Lys Asp Met Pro Thr Phe Ile Lys Met Asn
        615               620               625 aaa gct ata ttg aat aca gat gtg aaa tct tat gat gaa ata ata aaa        2936
Lys Ala Ile Leu Asn Thr Asp Val Lys Ser Tyr Asp Glu Ile Ile Lys
630               635               640               645 aaa tta agt gat gat gca aat aaa aat aca gaa tat caa aac cat att        2984
Lys Leu Ser Asp Asp Ala Asn Lys Asn Thr Glu Tyr Gln Asn His Ile
                650               655               660 caa gag tta gca gat aaa tat caa gga gca ggc ata cct cta gta tca        3032
Gln Glu Leu Ala Asp Lys Tyr Gln Gly Ala Gly Ile Pro Leu Val Ser
                665               670               675 gat gat tac tta aaa gat cat gga tat aag aaa gca tct gaa gta tat        3080
Asp Asp Tyr Leu Lys Asp His Gly Tyr Lys Lys Ala Ser Glu Val Tyr
            680               685               690 tct gaa att tca aaa gct gct tct ctt aca aac act agt gta aca gca        3128
Ser Glu Ile Ser Lys Ala Ala Ser Leu Thr Asn Thr Ser Val Thr Ala
        695               700               705 gaa aaa tct caa tat ttt aac aca ttc act tta aga gga act tat aca        3176
Glu Lys Ser Gln Tyr Phe Asn Thr Phe Thr Leu Arg Gly Thr Tyr Thr
710               715               720               725 ggt gaa act tct aaa ggt gaa ttt aaa gat tgg gat gaa atg agt aaa        3224
Gly Glu Thr Ser Lys Gly Glu Phe Lys Asp Trp Asp Glu Met Ser Lys
                730               735               740 aaa tta gat gga act ttg gag tcc ctt gct aaa aat tct tgg agt gga        3272
Lys Leu Asp Gly Thr Leu Glu Ser Leu Ala Lys Asn Ser Trp Ser Gly
                745               750               755 tac aaa act tta aca gca tac ttt acg aat tat aga gtt aca agc gat        3320
Tyr Lys Thr Leu Thr Ala Tyr Phe Thr Asn Tyr Arg Val Thr Ser Asp
            760               765               770 aat aaa gtt caa tat gat gta gtt ttc cat ggg gtt tta aca gat aat        3368
Asn Lys Val Gln Tyr Asp Val Val Phe His Gly Val Leu Thr Asp Asn
        775               780               785 gcg gat att agt aac aat aag gct cca ata gca aag gta act gga cca        3416
```

```
Ala Asp Ile Ser Asn Asn Lys Ala Pro Ile Ala Lys Val Thr Gly Pro
790             795                 800                 805 agc act ggt gct gta gga aga aat att gaa ttt agt gga aaa gat agt        3464
Ser Thr Gly Ala Val Gly Arg Asn Ile Glu Phe Ser Gly Lys Asp Ser
                    810                 815                 820 aaa gat gaa gat ggt aaa ata gta tca tat gat tgg gat ttt ggc gat        3512
Lys Asp Glu Asp Gly Lys Ile Val Ser Tyr Asp Trp Asp Phe Gly Asp
                825                 830                 835 ggt gca act agt aga ggc aaa aat tca gta cat gct tac aaa aaa gca        3560
Gly Ala Thr Ser Arg Gly Lys Asn Ser Val His Ala Tyr Lys Lys Ala
            840                 845                 850 gga aca tat aat gtt aca tta aaa gta act gac gat aag ggt gca aca        3608
Gly Thr Tyr Asn Val Thr Leu Lys Val Thr Asp Asp Lys Gly Ala Thr
        855                 860                 865 gct aca gaa agc ttt act ata gaa ata aag aac gaa gat aca aca aca        3656
Ala Thr Glu Ser Phe Thr Ile Glu Ile Lys Asn Glu Asp Thr Thr Thr
870                 875                 880                 885 cct ata act aaa gaa atg gaa cct aat gat gat ata aaa gag gct aat        3704
Pro Ile Thr Lys Glu Met Glu Pro Asn Asp Asp Ile Lys Glu Ala Asn
                890                 895                 900 ggt cca ata gtt gaa ggt gtt act gta aaa ggt gat tta aat ggt tct        3752
Gly Pro Ile Val Glu Gly Val Thr Val Lys Gly Asp Leu Asn Gly Ser
                905                 910                 915 gat gat gct gat acc ttc tat ttt gat gta aaa gaa gat ggt gat gtt        3800
Asp Asp Ala Asp Thr Phe Tyr Phe Asp Val Lys Glu Asp Gly Asp Val
            920                 925                 930 aca att gaa ctt cct tat tca ggg tca tct aat ttc aca tgg tta gtt        3848
Thr Ile Glu Leu Pro Tyr Ser Gly Ser Ser Asn Phe Thr Trp Leu Val
        935                 940                 945 tat aaa gag gga gac gat caa aac cat att gca agt ggt ata gat aag        3896
Tyr Lys Glu Gly Asp Asp Gln Asn His Ile Ala Ser Gly Ile Asp Lys
950                 955                 960                 965 aat aac tca aaa gtt gga aca ttt aaa tct aca aaa gga aga cat tat        3944
Asn Asn Ser Lys Val Gly Thr Phe Lys Ser Thr Lys Gly Arg His Tyr
                970                 975                 980 gtg ttt ata tat aaa cac gat tct gct tca aat ata tcc tat tct tta        3992
Val Phe Ile Tyr Lys His Asp Ser Ala Ser Asn Ile Ser Tyr Ser Leu
            985                 990                 995 aac ata aaa gga tta ggt aac gag aaa ttg aag gaa aaa gaa aat            4037
Asn Ile Lys Gly Leu Gly Asn Glu Lys Leu Lys Glu Lys Glu Asn
                1000                1005                1010 aat gat tct tct gat aaa gct aca gtt ata cca aat ttc aat acc            4082
Asn Asp Ser Ser Asp Lys Ala Thr Val Ile Pro Asn Phe Asn Thr
        1015                1020                1025 act atg caa ggt tca ctt tta ggt gat gat tca aga gat tat tat            4127
Thr Met Gln Gly Ser Leu Leu Gly Asp Asp Ser Arg Asp Tyr Tyr
    1030                1035                1040 tct ttt gag gtt aag gaa gaa ggc gaa gtt aat ata gaa cta gat            4172
Ser Phe Glu Val Lys Glu Glu Gly Glu Val Asn Ile Glu Leu Asp
    1045                1050                1055 aaa aag gat gaa ttt ggt gta aca tgg aca cta cat cca gag tca            4217
Lys Lys Asp Glu Phe Gly Val Thr Trp Thr Leu His Pro Glu Ser
    1060                1065                1070 aat att aat gac aga ata act tac gga caa gtt gat ggt aat aag            4262
Asn Ile Asn Asp Arg Ile Thr Tyr Gly Gln Val Asp Gly Asn Lys
    1075                1080                1085 gta tct aat aaa gtt aaa tta aga cca gga aaa tat tat cta ctt            4307
Val Ser Asn Lys Val Lys Leu Arg Pro Gly Lys Tyr Tyr Leu Leu
    1090                1095                1100
```

| | | | | | | | | | | | | | | |
|---|---|---|---|---|---|---|---|---|---|---|---|---|---|---|
| gtt | tat | aaa | tac | tca | gga | tca | gga | aac | tat | gag | tta | agg | gta | aat | 4352 |
| Val | Tyr | Lys | Tyr | Ser | Gly | Ser | Gly | Asn | Tyr | Glu | Leu | Arg | Val | Asn | |
| | | 1105 | | | | | 1110 | | | | | 1115 | | | | aaa taatttatct tataaaaaag agtgtgccta atacatggca cactcttttt    4405
Lys atttattttt ttcttttaaa agatctctga tttcaccaag taactcttct tctcttgaaa    4465
tttcaggaat cttagcttct tcaactgctt cttcttttct tttaaatctg tttattagtc    4525
ttataaatag gaatattgaa aaagaaatta ttaagaagtc aatatatttt tgtataaatt    4585
gaccataatt aagagtcaaa ggttttctg aatttaatcc atgaagtgta agttttgcgc    4645
tagtaaaatt aattccacct aagataagtc ctagaatagg cattataaca tcatttacta    4705
aagatgttac aatctttccg aaggcaccac ctatgataac acctacagca agatcgacta    4765
cattaccttt catggcaaat tccttaaaat cttttccacat aaaaatcctc ctaaagtatt    4825
taatattaat tattaaataa caagtataat cttatattta aatttaacat taattatact    4885 aaaatatcaat atgaaattat taaaagttttt acatttatt gatataaata atattggtat    4945
ttaatattat caggttgatt gttctttgtg ttctttaaat ttcaaaaaat atgatataat    5005
ataagagata gtatcgttgt ttgatatatc tatttaaaaa aaattactta gttttgttaa    5065
gaggtgtttt aaatgaagat tatgtttata tctgatattc atggttcttt atatttttta    5125
aataaagcat tagaaagatt tgaagaggaa aaagcagatt atataggag tttaggagat    5185 gtattatatc atggacctag aaatgattta ccaaaagaat ataatccaaa ggatgttgca    5245
aaaatcctaa ataggtataa aaataaaata atagccgtaa ggggaaattg tgatagtgaa    5305
gtagatcaaa tgcttataga ctatccaatg cttagtgatt atagtataat ttttttttaat    5365 aacaagaaaa tattttttaac tcacggacat attttttaata aagataatat gcctcatttt    5425
aatataggag atattatgat aagtggtcat actcatattc caagtataga acatatagac    5485
ggggtaactt ttataaatcc tggttctata tctataccta aaggtggaag tgaaaattct    5545 tatggtatttt taaatgagga tggattctca attaaaaatt taaatggaaa ggttatatta    5605
actttaaata tataatagac taaggagga ataagaatga atacaataga aatggtttta    5665
aatagtttaa aagaggcagg ggaaccgcta aaggctggag agatagcaga aaagactggt    5725
attgacaaaa agaagtgga taaagctata aaaaaattaa aagccgaaga aaagataact    5785
tctcctaaga ggtgttatta tactattgca taatattatc tcacatgata atattaaaat    5845
atattaaaaa ataataaaat gtaatgttta ggttctatt gtagattaat agggaaagtg    5905
gttgaattc    5914

<210> SEQ ID NO 13
<211> LENGTH: 1503
<212> TYPE: DNA
<213> ORGANISM: Artificial Sequence
<220> FEATURE:
<223> OTHER INFORMATION: GST-hbFGF-VBD(I)
<220> FEATURE:
<221> NAME/KEY: CDS
<222> LOCATION: (1)..(1503)

<400> SEQUENCE: 13

| | | | | | | | | | | | | | | | |
|---|---|---|---|---|---|---|---|---|---|---|---|---|---|---|---|
| atg | tcc | cct | ata | cta | ggt | tat | tgg | aaa | att | aag | ggc | ctt | gtg | caa | ccc | 48 |
| Met | Ser | Pro | Ile | Leu | Gly | Tyr | Trp | Lys | Ile | Lys | Gly | Leu | Val | Gln | Pro | |
| 1 | | | | 5 | | | | | 10 | | | | | 15 | | |

| | | | | | | | | | | | | | | | |
|---|---|---|---|---|---|---|---|---|---|---|---|---|---|---|---|
| act | cga | ctt | ctt | ttg | gaa | tat | ctt | gaa | gaa | aaa | tat | gaa | gag | cat | ttg | 96 |
| Thr | Arg | Leu | Leu | Leu | Glu | Tyr | Leu | Glu | Glu | Lys | Tyr | Glu | Glu | His | Leu | |
| | | 20 | | | | | 25 | | | | | 30 | | | | |

| | | |
|---|---|---|
| tat gag cgc gat gaa ggt gat aaa tgg cga aac aaa aag ttt gaa ttg<br>Tyr Glu Arg Asp Glu Gly Asp Lys Trp Arg Asn Lys Lys Phe Glu Leu<br>35 40 45 | 144 | |
| ggt ttg gag ttt ccc aat ctt cct tat tat att gat ggt gat gtt aaa<br>Gly Leu Glu Phe Pro Asn Leu Pro Tyr Tyr Ile Asp Gly Asp Val Lys<br>50 55 60 | 192 | |
| tta aca cag tct atg gcc atc ata cgt tat ata gct gac aag cac aac<br>Leu Thr Gln Ser Met Ala Ile Ile Arg Tyr Ile Ala Asp Lys His Asn<br>65 70 75 80 | 240 | |
| atg ttg ggt ggt tgt cca aaa gag cgt gca gag att tca atg ctt gaa<br>Met Leu Gly Gly Cys Pro Lys Glu Arg Ala Glu Ile Ser Met Leu Glu<br>85 90 95 | 288 | |
| gga gcg gtt ttg gat att aga tac ggt gtt tcg aga att gca tat agt<br>Gly Ala Val Leu Asp Ile Arg Tyr Gly Val Ser Arg Ile Ala Tyr Ser<br>100 105 110 | 336 | |
| aaa gac ttt gaa act ctc aaa gtt gat ttt ctt agc aag cta cct gaa<br>Lys Asp Phe Glu Thr Leu Lys Val Asp Phe Leu Ser Lys Leu Pro Glu<br>115 120 125 | 384 | |
| atg ctg aaa atg ttc gaa gat cgt tta tgt cat aaa aca tat tta aat<br>Met Leu Lys Met Phe Glu Asp Arg Leu Cys His Lys Thr Tyr Leu Asn<br>130 135 140 | 432 | |
| ggt gat cat gta acc cat cct gac ttc atg ttg tat gac gct ctt gat<br>Gly Asp His Val Thr His Pro Asp Phe Met Leu Tyr Asp Ala Leu Asp<br>145 150 155 160 | 480 | |
| gtt gtt tta tac atg gac cca atg tgc ctg gat gcg ttc cca aaa tta<br>Val Val Leu Tyr Met Asp Pro Met Cys Leu Asp Ala Phe Pro Lys Leu<br>165 170 175 | 528 | |
| gtt tgt ttt aaa aaa cgt att gaa gct atc cca caa att gat aag tac<br>Val Cys Phe Lys Lys Arg Ile Glu Ala Ile Pro Gln Ile Asp Lys Tyr<br>180 185 190 | 576 | |
| ttg aaa tcc agc aag tat ata gca tgg cct ttg cag ggc tgg caa gcc<br>Leu Lys Ser Ser Lys Tyr Ile Ala Trp Pro Leu Gln Gly Trp Gln Ala<br>195 200 205 | 624 | |
| acg ttt ggt ggt ggc gac cat cct cca aaa tcg gat ctg gtt ccg cgt<br>Thr Phe Gly Gly Gly Asp His Pro Pro Lys Ser Asp Leu Val Pro Arg<br>210 215 220 | 672 | |
| gga tct atg gca gcc ggg agc atc acc acg ctg ccc gcc ttg ccc gag<br>Gly Ser Met Ala Ala Gly Ser Ile Thr Thr Leu Pro Ala Leu Pro Glu<br>225 230 235 240 | 720 | |
| gat ggc ggc agc ggc gcc ttc ccg ccc ggc cac ttc aag gac ccc aag<br>Asp Gly Gly Ser Gly Ala Phe Pro Pro Gly His Phe Lys Asp Pro Lys<br>245 250 255 | 768 | |
| cgg ctg tac tgc aaa aac ggg ggc ttc ttc ctg cgc atc cac ccc gac<br>Arg Leu Tyr Cys Lys Asn Gly Gly Phe Phe Leu Arg Ile His Pro Asp<br>260 265 270 | 816 | |
| ggc cga gtt gac ggg gtc cgg gag aag agc gac cct cac atc aag cta<br>Gly Arg Val Asp Gly Val Arg Glu Lys Ser Asp Pro His Ile Lys Leu<br>275 280 285 | 864 | |
| caa ctt caa gca gaa gag aga gga gtt gtg tct atc aaa gga gtg tgt<br>Gln Leu Gln Ala Glu Glu Arg Gly Val Val Ser Ile Lys Gly Val Cys<br>290 295 300 | 912 | |
| gct aac cgt tac ctg gct atg aag gaa gat gga aga tta ctg gct tct<br>Ala Asn Arg Tyr Leu Ala Met Lys Glu Asp Gly Arg Leu Leu Ala Ser<br>305 310 315 320 | 960 | |
| aaa tgt gtt acg gat gag tgt ttc ttt ttt gaa cga ttg gaa tct aat<br>Lys Cys Val Thr Asp Glu Cys Phe Phe Phe Glu Arg Leu Glu Ser Asn<br>325 330 335 | 1008 | |
| aac tac aat act tac cgg tca agg aaa tac acc agt tgg tat gtg gca<br>Asn Tyr Asn Thr Tyr Arg Ser Arg Lys Tyr Thr Ser Trp Tyr Val Ala | 1056 | |

-continued

```
                340                      345                      350
ctg aaa cga act ggg cag tat aaa ctt gga tcc aaa aca gga cct ggg    1104
Leu Lys Arg Thr Gly Gln Tyr Lys Leu Gly Ser Lys Thr Gly Pro Gly
        355                      360                      365 cag aaa gct ata ctt ttt ctt cca atg tct gct aag agc gga att ccc    1152
Gln Lys Ala Ile Leu Phe Leu Pro Met Ser Ala Lys Ser Gly Ile Pro
    370                      375                      380 ggg aac gag aaa ttg aag gaa aaa gaa aat aat gat tct tct gat aaa    1200
Gly Asn Glu Lys Leu Lys Glu Lys Glu Asn Asn Asp Ser Ser Asp Lys
385                      390                      395                      400 gct aca gtt ata cca aat ttc aat acc act atg caa ggt tca ctt tta    1248
Ala Thr Val Ile Pro Asn Phe Asn Thr Thr Met Gln Gly Ser Leu Leu
                405                      410                      415 ggt gat gat tca aga gat tat tat tct ttt gag gtt aag gaa gaa ggc    1296
Gly Asp Asp Ser Arg Asp Tyr Tyr Ser Phe Glu Val Lys Glu Glu Gly
            420                      425                      430 gaa gtt aat ata gaa cta gat aaa aag gat gaa ttt ggt gta aca tgg    1344
Glu Val Asn Ile Glu Leu Asp Lys Lys Asp Glu Phe Gly Val Thr Trp
                435                      440                      445 aca cta cat cca gag tca aat att aat gac aga ata act tac gga caa    1392
Thr Leu His Pro Glu Ser Asn Ile Asn Asp Arg Ile Thr Tyr Gly Gln
        450                      455                      460 gtt gat ggt aat aag gta tct aat aaa gtt aaa tta aga cca gga aaa    1440
Val Asp Gly Asn Lys Val Ser Asn Lys Val Lys Leu Arg Pro Gly Lys
465                      470                      475                      480 tat tat cta ctt gtt tat aaa tac tca gga tca gga aac tat gag tta    1488
Tyr Tyr Leu Leu Val Tyr Lys Tyr Ser Gly Ser Gly Asn Tyr Glu Leu
                485                      490                      495 agg gta aat aaa taa                                                1503
Arg Val Asn Lys
        500
```